US008008273B2

(12) United States Patent
Kerr et al.

(10) Patent No.: US 8,008,273 B2
(45) Date of Patent: **\*Aug. 30, 2011**

(54) SHIP-DEFICIENCY TO INCREASE MEGAKARYOCYTE PROGENITOR PRODUCTION

(75) Inventors: William G. Kerr, Syracuse, NY (US); Caroline Desponts, La Jolla, CA (US); Lia Elena Perez, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/819,711

(22) Filed: Jun. 21, 2010

(65) Prior Publication Data

US 2010/0260730 A1    Oct. 14, 2010

Related U.S. Application Data

(60) Division of application No. 11/451,004, filed on Jun. 12, 2006, now Pat. No. 7,763,592, which is a continuation-in-part of application No. 10/904,667, filed on Nov. 22, 2004, now Pat. No. 7,807,646.

(60) Provisional application No. 60/481,677, filed on Nov. 20, 2003.

(51) Int. Cl.
*A61K 48/00* (2006.01)

(52) U.S. Cl. .......................... 514/44; 536/24.5; 536/24.1

(58) Field of Classification Search ........................ None
See application file for complete search history.

(56) References Cited

U.S. PATENT DOCUMENTS

| | | | |
|---|---|---|---|
| 4,603,112 A | 7/1986 | Paoletti et al. |
| 4,769,330 A | 9/1988 | Paoletti et al. |
| 4,777,127 A | 10/1988 | Suni et al. |
| 5,017,487 A | 5/1991 | Stunnenberg et al. |
| 5,166,057 A | 11/1992 | Palese et al. |
| 5,804,412 A | 9/1998 | Gill et al. |
| 6,025,198 A | 2/2000 | Bennett et al. |
| 6,090,621 A | 7/2000 | Kavanaugh et al. |
| 6,117,850 A | 9/2000 | Patchen et al. |
| 6,200,807 B1 | 3/2001 | Bennett et al. |
| 6,506,559 B1 | 1/2003 | Fire et al. |
| 6,703,215 B2 | 3/2004 | Erneux et al. |
| 7,691,821 B2 | 4/2010 | Desponts et al. |
| 7,713,945 B2 | 5/2010 | Kerr |
| 7,763,592 B1 | 7/2010 | Kerr et al. |
| 7,807,646 B1 | 10/2010 | Kerr et al. |
| 2002/0137711 A1 | 9/2002 | Kerr |
| 2002/0165192 A1 | 11/2002 | Kerr et al. |
| 2003/0114401 A1 | 6/2003 | Bennett et al. |
| 2003/0143732 A1 | 7/2003 | Fosnaugh et al. |
| 2003/0166282 A1 | 9/2003 | Brown et al. |
| 2004/0072298 A1 | 4/2004 | Sauvageau et al. |
| 2004/0235765 A1 | 11/2004 | Kerr et al. |
| 2004/0259247 A1 | 12/2004 | Tuschl et al. |
| 2005/0054103 A1 | 3/2005 | Peled et al. |
| 2006/0223749 A1 | 10/2006 | Desponts et al. |
| 2007/0224124 A1 | 9/2007 | Kerr et al. |
| 2008/0076731 A1 | 3/2008 | Kerr |
| 2010/0136026 A1 | 6/2010 | Kerr et al. |
| 2010/0144841 A1 | 6/2010 | Kerr |

FOREIGN PATENT DOCUMENTS

| | | |
|---|---|---|
| EP | 0 345 242 A2 | 12/1989 |
| EP | 0 440 219 A1 | 8/1991 |
| GB | 2 200 651 A | 8/1988 |
| WO | WO 89/01973 A2 | 3/1989 |
| WO | WO 91/02805 A2 | 3/1991 |
| WO | WO 92/06693 A1 | 4/1992 |
| WO | WO 97/10252 A1 | 3/1997 |
| WO | WO 97/12039 A2 | 4/1997 |
| WO | WO 99/32619 A1 | 7/1999 |
| WO | WO 02/24233 A2 | 3/2002 |
| WO | WO 02/44321 A2 | 6/2002 |
| WO | WO 02/078614 A3 | 10/2002 |
| WO | WO 2008/022468 A1 | 2/2008 |
| WO | WO 2009/042910 A2 | 4/2009 |

OTHER PUBLICATIONS

Crooke, S.T. "Progress in Antisense Technology" *Ann Rev Medicine*, 2004, 55:61-95.
Jang, J.H. et al. "Gene delivery from polymer scaffolds for tissue engineering" *Expert Rev. Medical Devices*, 2004, 1(1):127-138.
Office Action mailed Dec. 29, 2005 in U.S. Appl. No. 09/955,174, filed Sep. 19, 2001.
Office Action mailed Aug. 9, 2005 in U.S. Appl. No. 10/605,452, filed Sep. 30, 2003.
Office Action mailed Apr. 12, 2006 in U.S. Appl. No. 10/605,542, filed Sep. 30, 2003.
Office Action mailed Sep. 28, 2009 in U.S. Appl. No. 11/451,004, filed Jun. 12, 2006.
Office Action mailed Apr. 7, 2009 in U.S. Appl. No. 11/451,004, filed Jun. 12, 2006.
Office Action mailed Aug. 5, 2008 in U.S. Appl. No. 11/451,004, filed Jun. 12, 2006.
Notice of Allowance mailed Oct. 7, 2009 in U.S. Appl. No. 11/787,064, filed Apr. 13, 2007.
U.S. Appl. No. 10/605,452, Kerr et al.
U.S. Appl. No. 10/709,801, Desponts et al.
U.S. Appl. No. 10/904,667, Kerr et al. U.S. Appl. No. 12/670,360, Kerr et al.
U.S. Appl. No. 12/689,167, Desponts et al.
U.S. Appl. No. 12/651,809, Kerr.
Adams, A. "RNA Therapeutics Enter Clinical Trials" *The Scientist*, Jan. 17, 2005, 19(1):1-4.
Agrawal, S. "Antisense oligonucleotides: towards clinical trials" *Tibtech*, Oct. 1996, 14:376-387.
Agrawal, S. et al. "Antisense therapeutics: is it as simple as complementary base recognition" *Molecular Medicine Today*, Feb. 2000, 6:72-81.

(Continued)

*Primary Examiner* — Kimberly Chong
(74) *Attorney, Agent, or Firm* — Saliwanchik, Lloyd & Eisenschenk

(57) ABSTRACT

The invention concerns a method for increasing megakaryocyte and megakaryocyte progenitor numbers in vitro or in vivo by suppressing SH2-containing inositol-5-phosphatase (SHIP) function in megakaryocytes or megakaryocyte progenitors expressing the SHIP gene. SHIP function can be suppressed by administering an interfering RNA, or other SHIP inhibitor, to the megakaryocytes or megakaryocyte progenitors in vitro or in vivo.

13 Claims, 13 Drawing Sheets

OTHER PUBLICATIONS

Agrawal, N. et al. "RNA Interference: Biology, Mechanism, and Applications" *Microbiology and Molecular Biology*, Dec. 2003, 67(4):657-685.

Ahmed, N. et al. "Cytokine-Induced Expansion of Human CD34+ Stem/Progenitor and CD34+CD41+ Early Megakaryocytic Marrow Cells Cultured on Normal Osteoblasts" *Stem Cells*, 1999, 17:92-99.

Akagi, K. et al. "Cre-mediated somatic site-specific recombination in mice" *Nucleic Acids Research*, 1997, 25(9):1766-1773.

Bender, M.A. et al. "Description and Targeted Deletion of 5' Hypersensitive Site 5 and 6 of the Mouse β-Globin Locus Control Region" *Blood*, Dec. 1998, 92(11):4394-4403.

Bjorklund, L.M. et al. "Embryonic stem cells develop into functional dopaminergic neurons after transplantation in a Parkinson rat model" PNAS, Feb. 19, 2003, 99(4):2344-2349.

Bolland, S. et al. "SHIP Modulates Immune Receptor Responses by Regulating Membrane Association of Btk" *Immunity*, Apr. 1998, 8:509-516.

Bonetta, L. "RNAi: Silencing never sounded better" *Nature Methods*, Oct. 2004, 1(1):79-86.

Braasch, D.A. et al. "Novel Antisense and Peptide Nucleic Acid Strategies for Controlling Gene Expression" *Biochemistry*, Apr. 9, 2002 41(14):4503-4510.

Branch, A.D. "A good antisense molecule is hard to find" *TIBS*, Feb. 1998, 23:45-50.

Cantley, L.C. et al. "Oncogenes and Signal Transduction" *Cell*, Jan. 25, 1991, 64:281-302.

Caplen, N.J. et al. "Specific inhibition of gene expression by small double-stranded RNAs in invertebrate and vertebrate systems" *PNAS*, Aug. 14, 2001, 98(17):9742-9747.

Caplen, N.J. "RNAi as a gene therapy approach" *Expert Opinion Biol Ther.*, 2003, 3(4):575-586.

Chirila, T.V. et al. "The use of synthetic polymers for delivery of therapeutic antisense oligodeoxynucleotides" *Biomaterials*, 2002, 23:321-342.

Crooke, S.T. "Basic principles of antisense therapeutics" in Antisense Research and Application, Chapter 1, pp. 1-50, S. Crooke, Editor, Springer-Verlag, 1999.

Damen, J.E. et al. "The 145-kDa protein induced to associate with Shc by multiple cytokines is an inositol tetraphosphate and phosphatidylinositol 3,4,5-trisphosphate 5-phosphatase" *Proc Natl Acad Sci USA*, Feb. 1996, 93:1689-1693.

Desponts, C. et al. "MHC Class I inhibitory receptors on natural killer cells recruit SHIP in an attempt to control cell survival" *FASEB Journal*, Mar. 20, 2002, 16(4):A707, abstract.

De Souza, A.T. et al, "Transcriptional and phenotypic comparisons of Ppara knockout and siRNA knockdown mice" *Nucleic Acids Research*, 2006, 34(16):4486-4494.

Elbashir, S.M. et al. "RNA interference is mediated by 21-and 22-nucleotide RNAs" *Genes & Development*, 2001, 15:188-200.

Elbashir, S.M. et al. "Duplexes of 21-nucleotide RNAs mediate RNA interference in cultured mammalian cells" *Nature*, May 2001, 411:494-498.

Evans, D.J. et al. "An engineered poliovirus chimaera elicits broadly reactive HIV-1 neutralizing antibodies" *Nature*, Jun. 1989, 339:385-388.

Examination Report in European Application No. 01973144.7, dated Nov. 11, 2006.

Fire, A. et al. "Potent and specific genetic interference by double-stranded RNA in Caenorhabditis elegans" *Nature*, Feb. 1998, 391:806-811.

Fisher-Hoch, S.P. et al. "Protection of rhesus monkeys from fatal Lassa fever by vaccination with a recombinant vaccinia virus containing the Lassa virus glycoprotein gene" *Proc Natl Acad Sci USA*, Jan. 1989, 86:317-321.

Geier, S.J. et al. "The Human SHIP Gene Is Differentially Expressed in Cell Lineages of the Bone Marrow and Blood" *Blood*, 1997, 89:1876-1885.

Gewirtz, A.M. et al. "Facilitating oligonucleotide delivery: Helping antisense deliver on its promise" *Proc Natl Acad Sci USA*, Apr. 1996, 93:3161-3163.

Ghansah, T. et al. "A role for the SH2-containing Inositol phosphatase in the biology of natural killer cells and stem cells" in Activating and inhibitory immunoglobulin-like Receptors, 2001, pp. 129-140.

Ghansah, T. et al. "Target disruption of Src homology 2-containing 5' inositol phosphatase murine natural killer cells" *FASEB Journal*, Mar. 20, 2002, 16(4):A706, abstract.

Ghansah, T. et al. "The Src homology 2 containing inositol phosphatase is vital for the function and homeostasis of Natural Killer cells" *FASEB Journal*, Mar. 7, 2001, 15(4):A655, abstract.

Ghansah, T. et al. "Expansion of Myeloid Suppressor Cells in SHIP-Deficient Mice Represses Allogeneic T Cell Responses" *The Journal of Immunology*, 2004, 173:7324-7330.

Guzman, R.J. et al. "Efficient and Selective Adenovirus-Mediated Gene Transfer Into Vascular Neointima" *Circulation*, Dec. 1993, 88(6):2838-2848.

Hannon, G.J. et al. "Unlocking the potential of the human genome with RNA interference" *Nature*, Sep. 16, 2004, 431:371-378.

Harborth, J. et al. "Identification of essential genes in cultured mammalian cells using small interfering RNAs" *Journal of Cell Science*, 114(24):4557-4565, 2001.

Hawkins, P.T. et al. "Platelet-derived growth factor stimulates synthesis of PtdIns(3,4,5)P$_3$ by activating a PtdIns(4,5)P$_2$ 3-OH kinase" *Nature*, Jul. 1992, 358(6382):157-159.

Held, W. et al. "Transgenic Expression of the Ly49A Natural Killer Cell Receptor Confers Class I Major Histocompatibility Complex (MHC)-specific Inhibition and Prevents Bone Marrow Allograft Rejection" *J Exp Med*, Nov. 1996, 184:2037-2041.

Helgason, C.D. et al. "Targeted disruption of SHIP leads to homopoietic perturbations, lung pathology, and a shortened life span" *Genes & Development*, 1998, 12:1610-1620.

Helgason, C.D. et al. "Homeostasis and regeneration of the hematopoietic stem cell pool are altered in *SHIP*-deficient mice" *Blood*, 2003, 102(10):3541-3547.

Hemann, M.T. et al. "An epi-allelic series of p53 hypomorphs created by stable RNAi produces distinct tumor phenotypes in vivo" *Nature Genetics*, Mar. 2003, 33:396-400.

Hemmati-Brivanlou, A. et al. "Vertebrate Embryonic Cells Will Become Nerve Cells Unless Told Otherwise" *Cell*, Jan. 10, 1997, 88:13-17.

Huber, M. et al. "The src homology 2-containing inositol phosphatase (SHIP0 is the gatekeeper of mast cell degranulation" *Proc Natl Acad Sci USA*, Sep. 1998, 95:11330-11335.

Huber, M. et al. "The role of SHIP in growth factor induced signalling" *Progress in Biophysics & Molecular Biology*, 1999, 71:423-434.

Jefferson, A.B. et al. "Properties of Type II Inositol Polyphosphate 5-Phosphatase" *The Journal of Biological Chemistry*, Apr. 1995, 270(16):9370-9377.

Jen, K.Y. et al. "Suppression of Gene Expression by Targeted Disruption of Messenger RNA: Available Options and Current Strategies" *Stem Cells*, 2000, 18:307-319.

Jolly, D. "Viral vector systems for gene therapy" *Cancer Gene Therapy*, 1994, 1(1):51-64.

Kass-Eisler, A. et al. "Quantitative determination of adenovirus-mediated gene delivery to rat cardiac myocytes in vitro and in vivo" *Proc Natl Acad Sci USA*, Dec. 1993, 90:11498-11502.

Kawasaki, H. et al. "Induction of Midbrain Dopaminergic Neurotechnique Neurons from ES Cells by Stromal Cell-Derived Inducing Activity" *Neuron*, Oct. 2000, 28:31-40.

Kerr, W.G., "The SH2 Containing Inositol Phosphatase (SHIP) is a Crucial Regulator of NK Cell Repertoire and Function" Abstract #34, presented at Core Research for Evolutional Science and Technology (CREST) International Symposium on Immunoglobulin-like Receptors, held Sep. 19-20, 2000, at the Sendai International Center, Sendai City, Japan.

Kerr, W.G. et al. "Critical role for SHIP in engraftment of histoincompatible stem cells" *Oncology Research*, 2001, 12:285.

Kim, J.H. et al. "Dopamine neurons derived from embryonic stem cells function in an animal model of Parkinson's disease" *Nature*, Jun. 20, 2002, pp. 1-7, doi.1038/nature00900, advance online publication.

Klippel, A. et al. "Membrane Localization of Phosphatidylinositol 3-Kinase Is Sufficient to Activate Multiple Signal-Transducing Kinase Pathways" *Molecular and Cellular Biology*, Aug. 1996, 16(8):4117-4127.

Koh, C.Y. et al. "Augmentation of antitumor effects by NK cell inhibitory receptor blockade in vitro and in vivo" *Blood*, 2001, 97(10):3132-3137.

Kolls, J. et al. "Prolonged and effective blockade of tumor necrosis factor activity through adenovirus-mediated gene transfer" *Proc Natl Acad Sci. USA*, Jan. 1994, 91:215-219.

Krystal, G. et al. "Molecules in focus: SHIPs ahoy" *The International Journal of Biochemistry & Cell Biology*, 1999, 31:1007-1010.

Lanier, L.L. "NK Cell Receptors" *Annu Rev Immunol*, 1998, 16:359-393.

Lewis, D.L. et al. "Efficient delivery of siRNA for inhibition of gene expression in postnatal mice" *Nature Genetics*, Sep. 2002, 32:107-108.

Liu, L. et al. "The Src Homology 2 (SH2) Domain of SH2-containing Inositol Phosphatase (SHIP) Is Essential for Tyrosine Phosphorylation of SHIP, Its Association with Shc, and Its Induction of Apoptosis" *The Journal of Biological Chemistry*, Apr. 4, 1997, 272(14):8983-8988.

Liu, Q. et al. "Molecular Cloning and Chromosomal Localization in Human and Mouse of the SH2-Contianing Inositol Phosphatase, INPP5D (SHIP)" *Genomics*, 1997, 39:109-112.

Liu, Q. et al. "The Inositol Polyphosphate 5-Phosphatase Ship Is a Crucial Negative Regulator of B Cell Antigen Receptor Signaling" *J Exp Med*, Oct. 5, 1998, 188(7):1333-1342.

Liu, Q. et al. "SHIP is a negative regulator of growth factor receptor-mediated PKB/Akt activation and myeloid cell survival" *Genes & Development*, 1999, 13(7):786-791.

Lotzova, E. et al. "Prevention of Rejection of Allogeneic Bone Marrow Transplants by NK-1.1 Anti Serum" *Transplantation*, 1983, 35(5):490-494, abstract.

Lucas, D.M. et al. "A Novel Spliced Form of SH2-Containing Inositol Phosphatase is Expressed During Myeloid Development" *Blood*, Mar. 15, 1999, 93:6):1922-1933.

Muraille, E. et al. "Distribution of the Src-homology-2-domain-containing inositol 5-phosphatase SHIP-2 in both non-haemopoietic and haemopoietic cells and possible involvement of SHIP-2 in negative signaling of B-cells" *Biochem J*, 1999, 342:697-705.

Montgomery, M.K. et al. "RNA as a target of double-stranded RNA-mediated genetic interference in *Caenorhabditis elegans*" *Proc Natl Acad Sci USA*, Dec. 1998, 95:15502-15507.

Moody, J.L. et al. "Anemia, thrombocytopenia, leukocytosis, extramedullary hematopoiesis, and impaired progenitor function in $Pten^{+/-}SHIP^{-/-}$ mice: a novel model of myelodysplasia" *Blood*, 2004, 103:4503-4510.

Novina, C.D. et al. "The RNAi revolution" *Nature*, Jul. 8, 2004, 430:161-164.

Okada, H. et al. "Cutting Edge: Role of the Inositol Phosphatase SHIP in B Cell Receptor-Induced Ca2+ Oscillatory Response" *The Journal of Immunology*, 1998, 161:5129-5132.

Opalinska, J.B. et al."Nucleic-Acid Therapeutics: Basic Principles and Recent Applications" *Nature Reviews: Drug Discovery*, Jul. 2002, 1:503-514.

Odorico, J.S. et al. "Multilineage Differentiation from Human Embryonic Stem Cell Lines" *Stem Cells*, 2001, 19:193-204.

Overbaugh, J. et al. "Molecular Cloning of a Feline Leukemia Virus That Induces Fatal Immunodeficiency Disease in Cats" *Science*, 1988, 239:906-910.

Palu, G. et al. "In pursuit of new developments for gene therapy of human diseases" *Journal of Biotechnology*, 1999, 68:1-13.

Paroo, Z. et al. "Challenges for RNAi in vivo" *TRENDS in Biotechnology*, Aug. 2004, 22(8):390-394.

Pasquet, J.M. et al. "Phosphatidylinositol 3,4,5-trisphosphate regulates Ca2+ entry via Btk in platelets and megakaryocytes without increasing phospholipase C activity" *EMBO Journal*, Jun. 15, 2000, 19(12):2793-2802.

Pera, M.F. et al. "Commentary: Human embryonic stem cells" *Journal of Cell Science*, 2000, 113:5-10.

Peracchi, A. "Prospects for antiviral ribozymes and deoxyribozymes" *Reviews in Medical Virology*, 2004, 14:47-64,.

Perez, L.E. et al. "SH$_2$-Inositol Phosphatase 1 Negatively Influences Early Megakaryocyte Progenitors" *PLOS One*, Oct. 2008, 3(10):e3565, pp. 1-8.

Pesesse, X. et al. "The SH2 domain containing inositol 5-phosphatase SHIP2 displays phosphatidylinositol 3,4,5-trisphosphate and inositol 1,3,4,5-tetrakisphosphate 5-phosphatase activity" *FEBS Letters*, 1998, 437:301-303.

Pihl-Carey, K. "Disease Drug fails in Phase III" *BioWorld Today*, Dec. 16, 1999, 10:1-2.

Poznansky, M. et al. "Gene Transfer into Human Lymphocytes by a Defective Human Immunodeficiency Virus Type 1 Vector" *Journal of Virology*, Jan. 1991, 65(1):532-536.

Program and Abstracts for CREST International Symposium on Immunoglobulin-like Receptors, held Sep. 19-20, 2000.

Puente, X.S. et al. "Human and Mouse Proteases: A Comparative Genomic Approach" *Nature Reviews: Genetics*, Jul. 2003, 4:544-558.

Rauh, M.J. et al. "The role of SHIP1 in macrophage programming and activation" *Biochemical Society Transactions*, 2004, 32(5):785-788.

Rehli, M. et al. "The Membrane-Bound Ectopeptidase CPM as a Marker of Macrophage Maturation In Vitro and In Vivo" *Cellular Peptidases in Immune Functions and Diseases 2*, 2000, pp. 205-216, eds. Lagner and Ansorge, Kluwer Academic/Plenum Publishers.

Rohrschneider, L.R. et al. "Structure, function, and biology of SHIP proteins" *Genes & Development*, 2000, 14:505-520.

Ruggeri, L. et al. "Role of Natural Killer Cell Alloreactivity in HLA-Mismatched Hematopoietic Stem Cell Transplantation" *Blood*, Jul. 1, 1999, 94(1):333-339.

Sabin, A.B. et al. "History of Sabin attenuated poliovirus oral live vaccine strains" *Journal of Biological Standardization*, 1973, 1:115-118.

Samulski, R.J. et al. "Helper-Free Stocks of Recombinant Adeno-Associated Viruses: Normal Integration Does Not Require Viral Gene Expression" *Journal of Virology*, Sep. 1989, 63(9):3822-3828.

Statement of Dr. Toshiyuki Takai dated Apr. 10, 2007, an organizer of the CREST International Symposium on Immunoglobulin-like Receptors, held Sep. 19-20, 2000, 1 page.

Sauer, B. "Inducible Gene Targeting in Mice Using the Cre/lox System" *Methods: A Companion to Methods in Enzymology*, 1998, 14:381-392.

Sawyers, C.L. "Chronic Myeloid Leukemia" *The New England Journal of Medicine*, Apr. 29, 1999, 340(17):1330-1340.

Sly, L.M. et al. "SHIP, SHIP2, and PTEN activities are regulated in vivo by modulation of their protein levels: SHIP is up-regulated in macrophages and mast cells by lipopolysaccharide" *Experimental Hematology*, 2003, 31:1170-1181.

Stephens, L.R. et al. "Agonist-stimulated synthesis of phosphatidylinositol(3,4,5)-trisphosphate: a new intracellular signalling system?" *Biochimica et Biophysica Acta*, 1993, 1179:27-75.

Svoboda, P. et al. "Selective reduction of dormant maternal mRNAs in mouse oocytes by RNA interference" *Development*, 2000, 127:4147-4156.

Tamm, I. et al. "Antisense therapy in oncology: new hope for an old Idea?" *Lancet*, 2001, 358:489-497.

Tu, Z. et al. "Embryonic and hematopoietic stem cells express a novel SH2-containing inositol 5'-phosphatase isoform that partners with the Grb2 adapter protein" *Blood*, 2001, 98:2028-2038.

Tuschl, T. et al. "Targeted mRNA degradation by double-stranded RNA in vitro" *Genes & Development*, 13:3191-3197, 1999.

Tuschl, T. "RNA Interference and Small Interfering RNAs" *ChemBioChem*, 2001, 2:239-245.

Verfaillie, C.M. et al. "Hematopoietic stem cells for transplantation" *Nature Immunology*, 2002, 3(4):314-317.

Wang, C.Y. et al. "pH-sensitive immunoliposomes mediate target-cell-specific delivery and controlled expression of a foreign gene in mouse" *Proc Natl Acad Sci USA*, Nov. 1987, 84:7851-7855.

Wang, J.W. et al. "Influence of SHIP on the NK Repertoire and Allogeneic Bone Marrow Transplantation" *Science*, Mar. 15, 2002, 295:2094-2097.

Wang, J.W. et al. Identification of a Novel Lipopolysaccharide-Inducible Gene with Key Features of Both a Kinase Anchor Proteins and chs1/beige Proteins, *The Journal of Immunology*, 2001, 166:4586-4595.

Ware, M.D. et al. "Cloning and Characterization of Human SHIP, the 145-kD Inositol 5-Phosphatase That Associates With SHC After Cytokine Stimulation" *Blood*, Oct. 15, 1996, 88(8):2833-2840.

Wisniewski, D. et al. "Neoplasia: A Novel SH2-Containing Phosphatidylinositol 3,4,5-Trisphosphate 5-Phosphatase (SHIP2) Is Constitutively Tyrosine Phosphorylated and Associated With src Homologous and Collagen Gene (SHC) in Chronic Myelogenous Leukemia Progenitor Cells" *Blood*, Apr. 1999, 93(8):2707-2720.

Wolf, I. et al. "Cloning of the Genomic Locus of Mouse SH2 Containing Inositol 5-Phosphatase (SHIP) and a Novel 110-kDA Splice Isoform, SHIPδ" *Genomics*, 2000, 69:104-112.

Yokoyama, W.M. et al. "Natural killer cell receptors" *Current Opinion in Immunology*, 1998, 10:298-305.

Zamore, P.D. et al. "RNAi:Double-Stranded RNA Directs the ATP-Dependent Cleavage of mRNa at 21 to 23 Nucleotide Intervals" *Cell*, Mar. 31, 2000, 101:25-33.

Zandstra, P.W. et al. "Leukemia Inhibitory Factor (LIF) Concentration Modulates Embryonic Stem Cell Self-Renewal and Differentiation Independently of Proliferation" *Biotechnol Bioeng*, 2000, 69:607-617.

Zwaka, T.P. et al. "Homologous recombination in human embryonic stem cells" *Nature Biotechnology*, Feb. 10, 2003, pp. 1-3, doi: 10.1038/nbt788, advance online publication.

Office Action mailed Jan. 14, 2009 in U.S. Appl. No. 09/955,174, filed Sep. 19, 2001.

Office Action mailed Feb. 10, 2006 in U.S. Appl. No. 10/097,101, filed Feb. 14, 2002.

Office Action mailed Oct. 17, 2006 in U.S. Appl. No. 10/605,452, filed Sep. 30, 2003.

Office Action mailed Apr. 28, 2009 in U.S. Appl. No. 10/709,801, filed May 28, 2004.

Office Action mailed Sep. 22, 2008 in U.S. Appl. No. 10/709,801, filed May 28, 2004.

Office Action mailed Jan. 7, 2009 in U.S. Appl. No. 10/904,667, filed Nov. 22, 2004.

Office Action mailed Jul. 22, 2009 in U.S. Appl. No. 10/904,667, filed Nov. 22, 2004.

Office Action mailed Jun. 5, 2009 in U.S. Appl. No. 11/787,064, filed Apr. 13, 2007.

Office Action mailed Dec. 16, 2008 in U.S. Appl. No. 11/787,064, filed Apr. 13, 2007.

FIG. 2

```
   1 aaacaggaag tcagtcagtt aagctggtgg cagcagccga ggccaccaag aggcaacggg
  61 cggcaggttg cagtggaggg gcctccgctc cctcggtgg tgtgtgggtc ctgggggtgc
 121 ctgccggccc ggccgaggag gcccacgccc accatggtcc cctgctggaa ccatggcaac
 181 atcacccgct ccaaggcgga ggagctgctt tccaggacag gcaaggacgg gagcttcctc
 241 gtgcgtgcca gcgagtccat ctcccgggca tacgcgctct gcgtgctgta tcggaattgc
 301 gtttacactt acagaattct gcccaatgaa gatgataaat tcactgttca ggcatccgaa
 361 ggcgtctcca tgaggttctt caccaagctg gaccagctca tcgagtttta caagaaggaa
 421 aacatggggc tggtgaccca tctgcaatac cctgtgccgc tggaggaaga ggacacaggc
 481 gacgaccctg aggaggacac agaaagtgtc gtgtctccac ccgagctgcc ccaagaaac
 541 atcccgctga ctgccagctc ctgtgaggcc aaggaggttc cttttcaaa cgagaatccc
 601 cgagcgaccg agaccagccg gccgagcctc tccgagacat tgttccagcg actgcaaagc
 661 atggacacca gtgggcttcc agaagagcat cttaaggcca tccaagatta tttaagcact
 721 cagctcgccc aggactctga atttgtgaag acagggtcca gcagtcttcc tcacctgaag
 781 aaactgacca cactgctctg caaggagctc tatggagaag tcatccggac cctcccatcc
 841 ctggagtctc tgcagaggtt atttgaccag cagctctccc cgggcctccg tccacgtcct
 901 caggttcctg gtgaggccaa tcccatcaac atggtgtcca agctcagcca actgacaagc
 961 ctgttgtcat ccattgaaga caaggtcaag gccttgctgc acgagggtcc tgagtctccg
1021 caccggccct cccttatccc tccagtcacc tttgaggtga aggcagagtc tctgggatt
1081 cctcagaaaa tgcagctcaa agtcgacgtt gagtctggga aactgatcat taagaagtcc
1141 aaggatggtt ctgaggacaa gttctacagc cacaagaaaa tcctgcagct cattaagtca
1201 cagaaatttc tgaataagtt ggtgatcttg gtggaaacag agaaggagaa gatcctgcgg
1261 aaggaatatg ttttgctga ctccaaaaag agagaaggct tctgccagct cctgcagcag
1321 atgaagaaca agcactcaga gcagccggag cccgacatga tcaccatctt catcggcacc
1381 tggaacatgg gtaacgcccc cctcccaag aagatcacgt cctggtttct ctccaagggg
1441 cagggaaaga cgcgggacga ctctgcggac tacatccccc atgacattta cgtgatcggc
1501 acccaagagg accccctgag tgagaaggag tggctggaga tcctcaaaca ctccctgcaa
1561 gaaatcacca gtgtgacttt taaaacagtc gccatccaca cgctctggaa catccgcatc
1621 gtggtgctgg ccaagcctga gcacgagaac cggatcagcc acatctgtac tgacaacgtg
1681 aagacaggca ttgcaaacac actggggaac aagggagccg tggggtgtc gttcatgttc
1741 aatggaacct ccttagggtt cgtcaacagc cacttgactt caggaagtga aaagaaactc
1801 aggcgaaacc aaaactatat caacattctc cggttcctgg ccctgggcga caagaagctg
1861 agtccctta acatcactca ccgcttcacg cacctcttct ggtttgggga tcttaactac
1921 cgtgtggatc tgcctacctg ggaggcagaa accatcatcc agaaaatcaa gcagcagcag
1981 tacgcagacc tcctgtccca cgaccagctg ctcacagaga ggagggagca gaaggtcttc
2041 ctacacttcg aggaggaaga aatcacgttt gccccaacct accgttttga gagactgact
2101 cggacaaat acgcctacac caagcagaaa gcgacaggga tgaagtacaa cttgccttcc
2161 tggtgtgacc gagtcctctg gaagtcttat cccctggtgc acgtggtgtg tcagtcttat
2221 ggcagtacca gcgacatcat gacgagtgac cacagccctg tctttgccac atttgaggca
2281 ggagtcactt cccagtttgt ctccaagaac ggtcccggga ctgttgacag ccaaggacag
2341 attgagtttc tcaggtgcta tgccacattg aagaccaagt cccagaccaa attctacctg
2401 gagttccact cgagctgctt ggagagtttt gtcaagagtc aggaaggaga aaatgaagaa
2461 ggaagtgagg gggagctggt ggtgaagttt ggtgagactc ttccaaagct gaagcccatt
2521 atctctgacc ctgagtacct gctagaccag cacatcctca tcagcatcaa gtcctctgac
2581 agcgacgaat cctatgcga gggctgcatt gcccttcggt tagaggccac agaaacgcag
2641 ctgcccatct acacgcctct cacccaccat ggggagttga caggccactt ccaggggag
2701 atcaagctgc agacctctca gggcaagacg agggagaagc tctatgactt tgtgaagacg
2761 gagcgtgatg aatccagtgg gccaaagacc ctgaagagcc tcaccagcca cgaccccatg
2821 aagcagtggg aagtcactag caggggcct ccgtgcagtg gctccagcat cactgaaatc
2881 atcaaccca actacatggg agtggggccc tttgggccac caatgcccct gcacgtgaag
2941 cagaccttgt cccctgacca gcagcccaca gcctggagct acgaccagcc gcccaaggac
3001 tccccgctgg ggccctgcag gggagaaagt cctccgacac ctcccggcca gccgcccata
3061 tcacccaaga agttttacc ctcaacagca aaccggggtc tccctcccag gacacaggag
3121 tcaaggccca gtgacctggg aagaacgca ggggacacgc tgcctcagga ggacctgccg
3181 ctgacgaagc ccgagatgtt tgagaacccc tgtatgggg ccctgagttc cttccctaag
3241 cctgctccca ggaaggacca ggaatccccc aaaatgccgc ggaaggaacc ccgccctgc
3301 ccggaacccg gcatcttgtc gcccagcatc gtgctcacca agcccagga ggctgatcgc
```

FIG. 2-continued

```
3361 ggcgaggggc cggcaagca ggtgcccgcg ccccggctgc gctccttcac gtgctcatcc
3421 tctgccgagg gcagggcggc cggcggggac aagagccaag ggaagcccaa gaccccggtc
3481 agctcccagg ccccggtgcc ggccaagagg cccatcaagc cttccagatc ggaaatcaac
3541 cagcagaccc cgcccacccc gacgccgcgg ccgccgctgc cagtcaagag cccggcggtg
3601 ctgcacctcc agcactccaa gggccgcgac taccgcgaca acaccgagct cccgcatcac
3661 ggcaagcacc ggccggagga ggggccacca gggcctctag gcaggactgc catgcagtga
3721 agccctcagt gagctgccac tgagtcggga gcccagagga acggcgtgaa gccactggac
3781 cctctcccgg gacctcctgc tggctcctcc tgcccagctt cctatgcaag gctttgtgtt
3841 ttcaggaaag ggcctagctt ctgtgtggcc cacagagttc actgcctgtg agacttagca
3901 ccaagtgctg aggctggaag aaaaacgcac accagacggg caacaaacag tctgggtccc
3961 cagctcgctc ttggtacttg ggacccagt gcctcgttga gggcgccatt ctgaagaaag
4021 gaactgcagc gccgatttga gggtggagat atagataata ataatattaa taataataat
4081 ggccacatgg atcgaacact catgatgtgc caagtgctgt gctaagtgct ttacgaacat
4141 tcgtcatatc aggatgacct cgagagctga ggctctagcc acctaaaacc acgtgcccaa
4201 acccaccagt ttaaaacggt gtgtgttcgg aggggtgaaa gcattaagaa gcccagtgcc
4261 ctcctggagt gagacaaggg ctcggcctta aggagctgaa gagtctgggt agcttgttta
4321 gggtacaaga agcctgttct gtccagcttc agtgacacaa gctgctttag ctaaagtccc
4381 gcgggttccg gcatggctag gctgagagca gggatctacc tggcttctca gttctttggt
4441 tggaaggagc aggaaatcag ctcctattct ccagtggaga gatctggcct cagcttgggc
4501 tagagatgcc aaggcctgtg ccaggttccc tgtgccctcc tcgaggtggg cagccatcac
4561 cagccacagt taagccaagc ccccaacat gtattccatc gtgctggtag aagagtcttt
4621 gctgttgctc ccgaaagccg tgctctccag cctggctgcc agggagggtg ggcctcttgg
4681 ttccaggctc ttgaaatagt gcagcctttt cttcctatct ctgtggcttt cagctctgct
4741 tccttggtta ttaggagaat agatgggtga tgtctttcct tatgttgctt tttcaacata
4801 gcagaattaa tgtagggagc taaatccagt ggtgtgtgtg aatgcagaag ggaatgcacc
4861 ccacattccc atgatggaag tctgcgtaac caataaattg tgcctttctc actcaaaaaa
4921 aaaaa
```

FIG. 3A

MPAMVPGWNHGNITRSKAEELLSRAGKDGSFLVRASESIPRAYA

LCVLFRNCVYTYRILPNEDDKFTVQASEGVPMRFFTKLDQLIDFYKKENMGLVTHLQY

PVPLEEEDAIDEAEEDTVESVMSPPELPPRNIPMSAGPSEAKDLPLATENPRAPEVTR

LSLSETLFQRLQSMDTSGLPEEHLKAIQDYLSTQLLLDSDFLKTGSSNLPHLKKLMSL

LCKELHGEVIRTLPSLESLQRLFDQQLSPGLRPRPQVPGEASPITMVAKLSQLTSLLS

SIEDKVKSLLHEGSESTNRRSLIPPVTFEVKSESLGIPQKMHLKVDVESGKLIVKKSK

DGSEDKFYSHKKILQLIKSQKFLNKLVILVETEKEKILRKEYVFADSKKREGFCQLLQ

QMKNKHSEQPEPDMITIFIGTWNMGNAPPPKKITSWFLSKGQGKTRDDSADYIPHDIY

VIGTQEDPLGEKEWLELLRHSLQEVTSMTFKTVAIHTLWNIRIVVLAKPEHENRISHI

CTDNVKTGIANTLGNKGAAGVSFMFIGTSLGFVNSHLTSGSEKKLRRNQNYMNILRFL

ALGDKKLSPFNITHRFTHLFWLGDLNYRVELPTWEAEAIIQKIKQQQYSDLLAHDQLL

LERKDQKVFLHFEEEEITFAPTYRFERLTRDKYAYTKQKATGMKYNLPSWCDRVLWKS

YPLVHVVCQSYGSTSDIMTSDHSPVFATFEAGVTSQFVSKNGPGTVDSQGQIEFLACY

ATLKTKSQTKFYLEFHSSCLESFVKSQEGENEEGSEGELVVRFGETLPKLKPIISDPE

YLLDQHILISIKSSDSDESYGEGCIALRLETTEAQHPIYTPLTHHGEMTGHFRGEIKL

QTSQGKMREKLYDFVKTERDESSGMKCLKNLTSHDPMRQWEPSGRVPACGVSSLNEMI

NPNYIGMGPFGQPLHGKSTLSPDQQLTAWSYDQLPKDSSLGPGRGEGPPTPPSQPPLS

PKKFSSSTANRGPCPRVQEARPGDLGKVEALLQEDLLLTKPEMFENPLYGSVSSFPKL

VPRKEQESPKMLRKEPPPCPDPGISSPSIVLPKAQEVESVKGTSKQAPVPVLGPTPRI

RSFTCSSSAEGRMTSGDKSQGKPKASASSQAPVPVKRPVKPSRSEMSQQTTPIPAPRP

PLPVKSPAVLQLQHSKGRDYRDNTELPHHGKHRQEEGLLGRTAMQ

FIG. 3B

```
      ggcaatttct gagaggcaac aggcggcagg tctcagccta gagagggccc tgaactactt
  61  tgctggagtg tccgtcctgg gagtggctgc tgacccagtc caggagaccc atgcctgcca
 121  tggtccctgg gtggaaccat ggcaacatca cccgctccaa ggcagaggag ctactttcca
 181  gagccggcaa ggacgggagc ttccttgtgc gtgccagcga gtccatcccc cgggcctacg
 241  cactctgcgt gctgttccgg aattgtgttt acacttacag gattctgccc aatgaggacg
 301  ataaattcac tgttcaggca tccgaaggtg tccccatgag gttcttcacg aagctggacc
 361  agctcatcga cttttacaag aaggaaaaca tggggctggt gacccacctg cagtaccccg
 421  tgcccctgga ggaggaggat gctattgatg aggctgagga ggacactgta gaaagtgtca
 481  tgtcaccacc tgagctgcct cccagaaaca ttcctatgtc tgccgggccc agcgaggcca
 541  aggaccttcc tcttgcaaca gagaaccccc gagcccctga ggtcacccgg ctgagtctct
 601  ccgagacact gtttcagcgt ctacagagca tggataccag tgggcttccc gaggagcacc
 661  tgaaagccat ccaggattat ctgagcactc agctcctcct ggattccgac tttttgaaga
 721  cgggctccag caacctccct cacctgaaga agctgatgtc actgctctgc aaggagctcc
 781  atggggaagt catcaggact ctgccatccc tggagtctct gcagaggttg tttgaccaac
 841  agctctcccc aggccttcgc cacgacctca ggtgcccgg agaggccagt cccatcacca
 901  tggttgccaa actcagccaa ttgacaagtc tgctgtcttc cattgaagat aaggtcaagt
 961  ccttgctgca cgagggctca gaatctacca acaggcgttc ccttatccct ccggtcacct
1021  ttgaggtgaa gtcagagtcc ctgggcattc ctcagaaaat gcatctcaaa gtggacgttg
1081  agtctgggaa actgatcgtt aagaagtcca aggatggttc tgaggacaag ttctacagcc
1141  acaaaaaaat cctgcagctc attaagtccc agaagtttct aaacaagttg gtgattttgg
1201  tggagacgga gaaggagaaa atcctgagga aggaatatgt ttttgctgac tctaagaaaa
1261  gagaaggctt ctgtcaactc ctgcagcaga tgaagaacaa gcattcggag cagccagagc
1321  ctgacatgat caccatcttc attggcactt ggaacatggg taatgcaccc cctcccaaga
1381  agatcacgtc ctggtttctc tccaaggggc agggaaagac acgggacgac tctgctgact
1441  acatccccca tgacatctat gtgattggca cccaggagga tccccttgga gagaaggagt
1501  ggctggagct actcaggcac tccctgcaag aagtcaccag catgacattt aaaacagttg
1561  ccatccacac cctctggaac attcgcatag tggtgcttgc caagccagag catgagaatc
1621  ggatcagcca tatctgcact gacaacgtga agacaggcat cgccaacacc tgggaaaaca
1681  agggagcagc gggagtgtcc ttcatgttca ttggaacctc cttggggttc gtcaacagcc
1741  acttgacttc tggaagtgaa aaaagctca ggagaaatca aaactatatg aacatcctgc
1801  ggttcctggc cctgggagac aagaagctaa gcccatttaa catcacccac cgcttcaccc
1861  acctcttctg gcttggggat ctcaactacc gcgtggagct gcccacttgg gaggcagagg
1921  ccatcatcca gaagatcaag caacagcagt attcagacct tctgcccac gaccaactgc
1981  tcctggagag gaaggaccag aaggtcttcc tgcactttga ggaggaagag atcaccttcg
2041  cccccaccta tcgatttgaa agactgaccc gggacaagta tgcatacacg aagcagaaag
2101  caacagggat gaagtacaac ttgccgtcct ggtgcgaccg agtcctctgg aagtcttacc
2161  cgctggtgca tgtggtctgt cagtcctatg cagtaccag tgacatcatg acgagtgacc
2221  acagccctgt ctttgccacg tttgaagcag gagtcacatc tcaattcgtc tccaagaatg
2281  gtcctggcac tgtagatagc caagggcaga tcgagtttct tgcatgctac gccacactga
2341  agaccaagtc ccagactaag ttctacttgg agttccactc aagctgctta gagagttttg
2401  tcaagagtca ggaaggagag aatgaagagg gaagtgaagg agagctggtg gtacggtttg
2461  gagagactct tcccaagcta aagcccatta tctctgaccc cgagtactta ctggaccagc
2521  atatcctgat cagcattaaa tcctctgaca gtgacgagtc ctatggtgaa ggctgcattg
2581  cccttcgctt ggagaccaca gaggctcagc atcctatcta cacgcctctc acccaccatg
2641  gggagatgac tggccacttc aggggagaga ttaagctgca gacctcccag gcaagatga
2701  gggagaagct ctatgacttt gtgaagacag agcgggatga atccagtgga atgaaatgct
2761  tgaagaacct caccagccat gacccctatga ggcaatggga gccttctggc agggtccctg
2821  catgtggtgt ctccagcctc aatgagatga tcaatccaaa ctacattggt atggggcctt
2881  ttggacagcc cctgcatggg aaatcaaccc tgtccccaga tcagcaactc acagcttgga
2941  gttatgacca gctacccaaa gactctcccc tggggcctgg gagggggag ggtcctccaa
3001  cccctccctc ccaaccacct ctgtcgccaa agaagttttc atcttccaca gccaaccgag
3061  gtccctgccc caggtgcaa gaggcaagac ctgggatcc tgggaaggtg gaagctctgc
3121  tccaggagga cctgctgctg acgaagcccg agatgtttga gaacccactg tatggatccg
3181  tgagttcctt ccctaagctg gtgcccagga aagagcagga gtctcccaag atgctgcgga
```

FIG. 3B-continued

```
3241 aggagccccc gccctgtcca gacccaggaa tctcatcacc cagcatcgtg ctccccaaag
3301 cccaagaggt ggagagtgtc aaggggacaa gcaaacaggc ccctgtgcct gtccttggcc
3361 ccacaccccg gatccgctcc tttacctgtt cttcttctgc tgagggcaga atgaccagtg
3421 gggacaagag ccaagggaag cccaaggcct cagccagttc caagcccca gtgccagtca
3481 agaggcctgt caagccttcc aggtcagaaa tgagccagca gacaacaccc atcccagctc
3541 cacggccacc cctgccagtc aagagtcctg ctgtcctgca gctgcaacat tccaaaggca
3601 gagactaccg tgacaacaca gaactccccc accatggcaa gcaccgccaa gaggaggggc
3661 tgcttggcag gactgccatg cagtgagctg ctggtgatcg gagcctggag gaacagcaca
3721 aagcagacct cgcctctct caggatgcct ctctcaggat gcctcttgga ggacctcctg
3781 ctagctcttc ttgcctagct tcaagtccca ggctgtgtat tttttttcag gaaacggcct
3841 cacttctctg tggtccaaga agtgtgctgc tggctgccac actgtgcggc agatgctaaa
3901 gctggatgac aaacgacgc catacagaca gcagacagcg gcactgggtc tcagaacttg
3961 gattcctggg ccttcttcca gtcgccgttt taaagaaagg aactaacgga gctgctcatc
4021 cgagggtgaa gatataaata ataatattat taataataat aacagtcagg tgccatgtgc
4081 tgtgttaagt gctttatgaa catttgtcgg gctggcctcc agtgctgagg tgccagtcag
4141 cctgaaccct atgcccaggc ccactaatcc caaatggtgg gtcctgagat gttttaaaa
4201 agcattaaag aaaaccatcg gtctcttaga gctaaccggc cgggctctac tgcagggacc
4261 cgaacagtct gcatggctaa gtggcacaag gagcctggcc ctgtccagct tcagagatcc
4321 aagctgcttt ttgctggggt tctgtcacag gcctgatcct cttggttttt atggggtttc
4381 aagtctgcca gagtcagaaa tcagctctaa ctcgccagtg aagagatctg gccttaactt
4441 aagccagcca cgtcaggccc ctgctgagcc tatggaccaa taaatactcc ccgtgccact
4501 ggaggtgggc agctatcacc ataccctgag ttgggccaag cccacccac ccctaccctg
4561 caacatttct gatgtwctga ggaagagtct ccaccatagt ccccaagggc tgagttctcc
4621 agcctgctat cagggaaggt gagcattggt cccagctct caaaatagtg cagcctcttc
4681 ttcccaagct ctggggtgca ccctgtgtcc ttggttacca ggagactagg gttgtgatat
4741 cttttcttgt cttgcttttt gatatatcag gattaatgta ggaaaccaga cctagattat
4801 tcaggagagt aggtatatcc cctgtgtttc ccagtctgag tgaccaataa aattgtgcct
4861 ttcta
```

```
   1 aaacaggaag tcagtcagtt aagctggtgg cagcagccga ggccaccaag aggcaacggg
  61 cggcaggttg cagtggaggg gcctccgctc ccctcggtgg tgtgtgggtc ctgggggtgc
 121 ctgccggccc ggccgaggag gccacgccc accatggtcc cctgctggaa ccatggcaac
 181 atcacccgct ccaaggcgga ggagctgctt tccaggacag gcaaggacgg gagcttcctc
 241 gtgcgtgcca gcgagtccat ctcccgggca tacgcgtctc gcgtgctgta tcggaatgc
 301 gtttacactt aca gaattct gcccaatgaa gatgataaat tcactgttca ggcatccgaa
 361 ggcgtctcca tgaggttctt caccaagctg gaccagctca tcgagtttta caagaaggaa
 421 aacatggggc tggtgaccca tctgcaatac cctgtgccgc tggaggaaga ggacacaggc
 481 gacgaccctg aggaggacac agaaagtgtc gtgtctccac cc gagctgcc cccaagaaac
 541 atcccgctga ctgccagctc ctgtgaggcc aaggaggttc cttttcaaa cgagaatccc
 601 cgagcgaccg agaccagccg gccgagcctc tccgagacat tgttccagcg actgcaaagc
 661 atggacacca gggcgtcc agaagagcat ctt aaggcca tccaagatta tttaagcact
 721 cagctcgccc aggactctga atttgtgaag acagggtcca gcagtcttcc tcacctgaag
 781 aaactgacca cactgctctg caaggagctc tatggagaag tcatccggac cctcccatcc
 841 ctggagtctc tgcagaggtt atttgaccag cagctctccc cgggcctccg tccacgtcct
 901 caggttcctg gtgaggccaa tccc atcaac atggtgtcca agctcagcca actgacaagc
 961 ctgttgtcat ccattgaaga caaggtcaag gccttgctgc acgagggtcc tgagtctccg
1021 cacggcccct cctttatccc tccagtcacc tttgaggtga aggcagagtc tctggggatt
1081 cctcagaaaa tgcagctcaa agtcgacgtt gagtctggga aactgatcat taagaagtcc
1141 aaggatggtt ctgaggacaa gttctacagc cacaagaaaa tcctgcagct cattaagtca
1201 cagaaatttc tgaataagtt ggtgatcttg gtggaaacag agaaggagaa gatcctgcgg
1261 aaggaatatg ttttttgctga ctccaaaaag agagaaggct tctgccagct cctgcagcag
1321 atgaagaaca agcactcaga gcagccggag cccgacatga tcaccatctt catcggcacc
1381 tggaacatgg gtaacgcccc ccctcccaag aagatcacgt cctggttctct ctccaagggg
1441 cagggaaaga cgcgggacga ctctgcggac tatatcccc atgacattta cgtgatcggc
1501 acccaagagg acccctgag tgagaaggag tggctggaga tcctcaaaca ctccctgcaa
1561 gaaatcacca gtgtgacttt taaaacagtc gccatccaca cgctctggaa catccgcatc
1621 gtggtgctgg ccaagcctga gcacgagaac cggatcagtc acatctgtac tgacaacgtg
1681 aagacaggca ttgcaaacac actggggaac aagggagccg tggggtgtc gttcatg ttc
1741 aatggaacct cctaggggtt cgtcaacagc cacttgactt caggaagtga aagaaactc
1801 aggcgaaacc aaaactatat gaacattctc cggttcctgg ccctgggcga caagagctg
1861 agtccttta acatcactca ccgcttcacg cacctcttct ggtttgggga tcttaactac
1921 cgtgtgatc tgcctacctg ggaggcagaa accatcatcc agaaaatcaa gcagcagcag
1981 tacgcagacc tcctgtccca cgaccagctg ctcacagaga ggagggagca gaaggtcttc
2041 ctacacttcg aggaggaaga aatcacgttt gccccaacct accgttttga gagactgact
2101 cgggacaaat acgcctacac caagcagaaa gcgacaggga tgaagtacaa cttgccttcc
2161 tggtgtgacc gagtcctctg gaagtcttat cccctggtgc acgtggtgtg tcagtcttat
2221 ggcagtacca gcgacatcat gacgagtgac cacagccctg tctttgccac attttgaggca
2281 ggagtcactt cccagtttgt ctccaagaac ggtcccggga ct gttgacag ccaaggacag
2341 attgagtttc tcagttgcta tgccacattg aagaccaagt cccagaacaa attctacctg
2401 gagttccact cgagctgctt ggagagtttt gtcaagagtc aggaaggaga aaatgaagaa
2461 ggaagtgagg gggactggtt ggtgaagttt ggtgagactc ttccaaagcct gaagcccatt
2521 atctctgacc ctgagtacct gctagaccag cacatcctca tcagcatcaa gtcctctgac
2581 agcgacgaat cctatggcga gggctgcatt gcccttcggt tagaggccac agaaacgcag
2641 ctgcccatct acacgcctct caccccaccat gggcagggaa caggccactt ccagggggag
2701 atcaagctgc agacctctca gggc aagacg agggagaagc tctatgactt tgtgaagacg
2761 gagcgtgatg aatccagtgg gccaaagacc ctgaagagcc tcaccagcca cgaccccatg
2821 aagcagtggg aagtcactac caggggcccct ccgtcgcagtg gctccagcat cactgaaatc
2881 atcaacccca actacatggg agtgggcgcc tttgggccac caatgcccct gcacgtgaag
2941 cagacccttgt ccctgacca gcagcccaca gcctggagct acgaccagcc gcccaaggac
3001 tcccgctgg ggccctgcag gggagaaagt cctccgacac ctcccggcca gcgg ccata
3061 tcacccaaga agttttacc ctcaacagca aaccgggctc tccctcccag gacacaggag
3121 tcaaggccca gtgacctggg gaagaacgca ggggacacgc tgcctcagga ggacctgccg
3181 ctgacgaagc ccgagatgtt tgagaacccc ctgtatgggt ccctgagttc cttccctaag
3241 cctgctccca ggaaggacca ggaatccccc aaaatgcctc ggaaggaacc ccggccctgc
3301 ccggaacccg gcatcttgtc gcccagcatc g tgctcacca aagcccagga ggctgatcgc
3361 ggcgaggggc ccgcaagca ggtgcccgcg cccggctgc gctccttcac gtgctcatcc
3421 tctgccgagg gcagggcggc cggcggggac aagagccaag ggaagccaa gaccccggtc
3481 agctcccagg cccggtgcc ggccaagagg cccatcaagc cttccagatc ggaaatc aac
3541 cagcagacc cgcccaccc gacgccgcgg ccgccgctgc cagtcaagag ccggcggtg
3601 ctgcacctcc agcactccaa gggccgcgac tacgcgcaca acaccggagct cccgcatcac
3661 ggcaagcacc gggcggagga ggggccacca ggggctctag gcaggactgc catgcagtga
3721 agccctcagt gagctgccac tgagtcggga gcccagagga acggcgtgaa gccactggac
3781 cctctccggg gacctcctgc tggctcttcc tgcccagctt cctatgcaag gctttgtgtt
3841 ttcaggaaag ggctagctt ctgtgtgcc cacagagttc actgcctgtg agacttagca
3901 ccaagtgctg aggctggaag aaaaacgcac acgagacggg caacaaacag tctgggctcc
3961 cagctcgctc ttggtacttg ggacccagt gcctcgttga gggcgccatt ctgaagaaag
4021 gaactgcagc gccgatttga gggtgagat atagataata ataatattaa taataataat
4081 ggccacatgg atcgaacact catgatgtgc caagtgctgt gc taagtgct ttacgaacat
4141 tcgtcatatc aggatgacct cgagagctga ggctctagcc acctaaaacc acgtgcccaa
4201 acccaccagt ttaaaacggt gtgtgttcgg aggggtgaaa gcattaagaa gcccagtgcc
4261 ctcctggagt gagacaaggg ctcggcctta aggagctgaa gagtctgggt agcttgttta
4321 gggtacaaga agcctgttct gtccagcttc agtgacacaa gctgcttag ctaaagtccc
4381 gcgggttccg gcatggctag gctgagagca gggatctacc tggcttctca gttcttggt
4441 tggaaggagc aggaaatcag ctcctattct ccagtggaga gatctggcct cagcttgggc
4501 tagagatgcc aaggcctgtg ccag gttccc tgtgccctcc tcgaggtggg cagccatcat
4561 cagccacagt taagccaagc ccccaacat gtattccatc gtgctggtag aagagtcttt
4621 gctgttgctc ccgaaagccg tgtctccag cctggctgcc agggaggtg ggcctcttgg
4691 ttccaggctc ttgaaatagt gcagccttt ctcctatct ctgtggcttt cagctctgct
4741 tccttggtta ttaggagaat agatgggtga tgtctttcct tatgttgctt ttcaacata
4801 gcagaattaa tgtagggagc taaatccagt ggtctgtgtg aatgcagaag ggaatgcacc
4861 ccacattccc atgatggaag tctgcgtaac caataaattg tgcctttctc actcaaaaaa
4921 aaaaa
```

▓ SHIP-1 shRNA 1
▓ SHIP-1 shRNA 2
▓ SHIP-1 siRNA H1
▓ SHIP-1 siRNA H2

FIG. 4

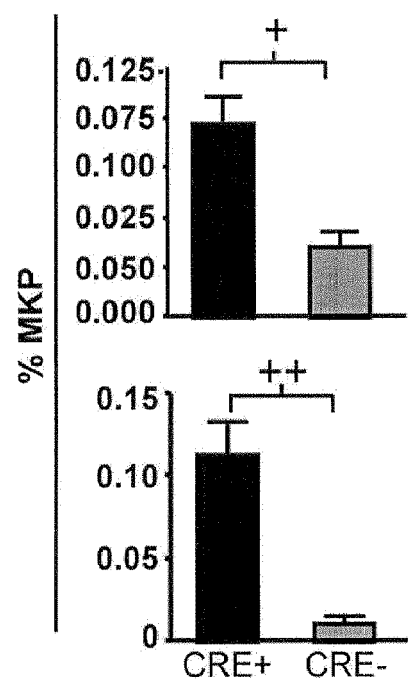
FIG. 5B-1
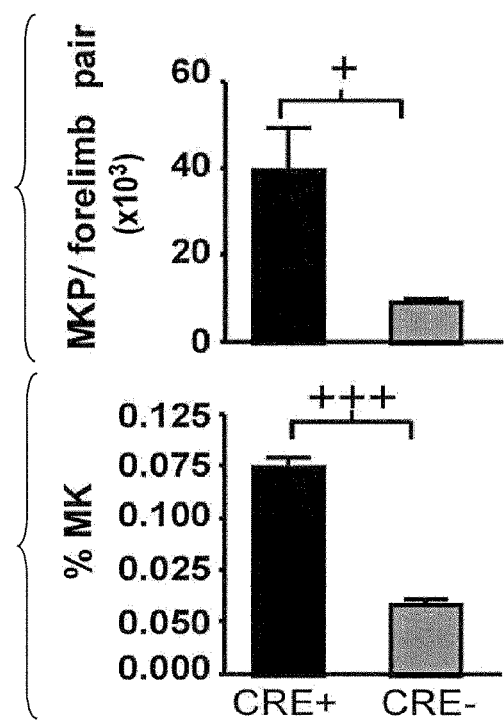
FIG. 5B-2
FIG. 5B-3

SEQUENCE LISTING

```
<160> NUMBER OF SEQ ID NOS: 21

<210> SEQ ID NO 1
<211> LENGTH: 4925
<212> TYPE: DNA
<213> ORGANISM: Homo sapiens

<400> SEQUENCE: 1
aaacaggaag tcagtcagtt aagctggtgg cagcagccga ggccaccaag aggcaacggg      60
cggcaggttg cagtggaggg gcctccgctc ccctcggtgg tgtgtgggtc ctgggggtgc     120
ctgccggccc ggccgaggag gcccacgccc accatggtcc cctgctggaa ccatggcaac     180
atcacccgct ccaaggcgga ggagctgctt tccaggacag gcaaggacgg gagcttcctc     240
gtgcgtgcca gcgagtccat ctcccgggca tacgcgctct gcgtgctgta tcggaattgc     300
gtttacactt acagaattct gcccaatgaa gatgataaat tcactgttca ggcatccgaa     360
ggcgtctcca tgaggttctt caccaagctg gaccagctca tcgagtttta caagaaggaa     420
aacatggggc tggtgaccca tctgcaatac cctgtgccgc tggaggaaga ggacacaggc     480
gacgaccctg aggaggacac agaaagtgtc gtgtctccac ccgagctgcc cccaagaaac     540
atcccgctga ctgccagctc ctgtgaggcc aaggaggttc cttttcaaa cgagaatccc     600 cgagcgaccg agaccagccg gccgagcctc tccgagacat tgttccagcg actgcaaagc     660
atggacacca gtgggcttcc agaagagcat cttaaggcca tccaagatta tttaagcact     720
cagctcgccc aggactctga atttgtgaag acagggtcca gcagtcttcc tcacctgaag     780
aaactgacca cactgctctg caaggagctc tatggagaag tcatccggac cctcccatcc     840
```

```
ctggagtctc tgcagaggtt atttgaccag cagctctccc cgggcctccg tccacgtcct    900
caggttcctg gtgaggccaa tcccatcaac atggtgtcca agctcagcca actgacaagc    960
ctgttgtcat ccattgaaga caaggtcaag gccttgctgc acgagggtcc tgagtctccg   1020
caccggccct cccttatccc tccagtcacc tttgaggtga aggcagagtc tctgggatt    1080
cctcagaaaa tgcagctcaa agtcgacgtt gagtctggga aactgatcat taagaagtcc   1140
aaggatggtt ctgaggacaa gttctacagc cacaagaaaa tcctgcagct cattaagtca   1200
cagaaatttc tgaataagtt ggtgatcttg gtggaaacag agaaggagaa gatcctgcgg   1260
aaggaatatg ttttttgctga ctccaaaaag agagaaggct tctgccagct cctgcagcag   1320
atgaagaaca agcactcaga gcagccggag cccgacatga tcaccatctt catcggcacc   1380
tggaacatgg gtaacgcccc ccctcccaag aagatcacgt cctggtttct ctccaagggg   1440
caggaaaaga cgcgggacga ctctgcggac tacatccccc atgacattta cgtgatcggc   1500
acccaagagg accccctgag tgagaaggag tggctggaga tcctcaaaca ctccctgcaa   1560
gaaatcacca gtgtgacttt taaaacagtc gccatccaca cgctctggaa catccgcatc   1620
gtggtgctgg ccaagcctga gcacgagaac cggatcagcc acatctgtac tgacaacgtg   1680
aagacaggca ttgcaaacac actggggaac aagggagccg tgggggtgtc gttcatgttc   1740
aatgaacct cctagggtt cgtcaacagc cacttgactt caggaagtga aaagaaactc   1800
aggcgaaacc aaaactatat gaacattctc cggttcctgg ccctgggcga caagaagctg   1860
agtccctta acatcactca ccgcttcacg cacctcttct ggtttgggga tcttaactac   1920
cgtgtggatc tgcctacctg ggaggcagaa accatcatcc agaaaatcaa gcagcagcag   1980
tacgcagacc tcctgtccca cgaccagctg ctcacagaga ggagggagca aaggtcttc    2040
ctacacttcg aggaggaaga aatcacgttt gccccaacct accgttttga gagactgact   2100
cgggacaaat acgcctacac caagcagaaa gcgacaggga tgaagtacaa cttgccttcc   2160
tggtgtgacc gagtcctctg gaagtcttat ccctggtgc acgtggtgtg tcagtcttat   2220
ggcagtacca gcgacatcat gacgagtgac cacagccctg tctttgccac atttgaggca   2280
ggagtcactt cccagtttgt ctccaagaac ggtcccggga ctgttgacag ccaaggacag   2340
attgagtttc tcaggtgcta tgccacattg aagaccaagt cccagaccaa attctacctg   2400
gagttccact cgagctgctt ggagagtttt gtcaagagtc aggaaggaga aaatgaagaa   2460
ggaagtgagg gggagctggt ggtgaagttt ggtgagactc ttccaaagct gaagcccatt   2520
atctctgacc ctgagtacct gctagaccag cacatcctca tcagcatcaa gtcctctgac   2580
agcgacgaat cctatggcga gggctgcatt gcccttcggt tagaggccac agaaacgcag   2640
ctgcccatct acacgcctct cacccaccat ggggagttga caggccactt ccaggggag    2700
atcaagctgc agacctctca gggcaagacg agggagaagc tctatgactt tgtgaagacg   2760
gagcgtgatg aatccagtgg gccaaagacc ctgaagagcc tcaccagcca cgaccccatg   2820
aagcagtggg aagtcactag cagggcccct ccgtgcagtg ctccagcat cactgaaatc    2880
atcaaccccca actacatggg agtggggccc tttgggccac caatgcccct gcacgtgaag   2940
cagaccttgt cccctgacca gcagcccaca gcctggagct acgaccagcc gcccaaggac   3000
tccccgctgg ggccctgcag gggagaaagt cctccgacac ctcccggcca gccgccata    3060
tcacccaaga gttttttacc ctcaacagca aaccggggtc tccctcccag gacacaggag   3120
tcaaggccca gtgacctggg gaagaacgca ggggacacgc tgcctcagga ggacctgccg   3180
ctgacgaagc ccgagatgtt tgagaacccc ctgtatgggt ccctgagttc cttccctaag   3240
```

```
cctgctccca ggaaggacca ggaatccccc aaaatgccgc ggaaggaacc cccgccctgc    3300
ccggaacccg gcatcttgtc gcccagcatc gtgctcacca agcccagga ggctgatcgc    3360 ggcgagggc  ccggcaagca ggtgcccgcg ccccggctgc gctccttcac gtgctcatcc    3420
tctgccgagg gcagggcggc cggcggggac aagagccaag ggaagcccaa gaccccggtc    3480
agctcccagg ccccggtgcc ggccaagagg cccatcaagc cttccagatc ggaaatcaac    3540
cagcagaccc cgcccacccc gacgccgcgg ccgccgctgc cagtcaagag cccggcggtg    3600
ctgcacctcc agcactccaa gggcgcgac  taccgcgaca caccgagct  cccgcatcac    3660 ggcaagcacc ggccggagga ggggccacca gggcctctag gcaggactgc catgcagtga    3720
agccctcagt gagctgccac tgagtcggga gccagagga  acggcgtgaa gccactggac    3780
cctctcccgg gacctcctgc tggctcctcc tgcccagctt cctatgcaag gctttgtgtt    3840
ttcaggaaag ggcctagctt ctgtgtggcc cacagagttc actgcctgtg agacttagca    3900
ccaagtgctg aggctggaag aaaaacgcac accagacggg caacaaacag tctgggtccc    3960
cagctcgctc ttggtacttg gaccccagt  gcctcgttga gggcgccatt ctgaagaaag    4020
gaactgcagc gccgatttga gggtggagat atagataata ataatattaa taataataat    4080
ggccacatgg atcgaacact catgatgtgc caagtgctgt gctaagtgct ttacgaacat    4140
tcgtcatatc aggatgacct cgagagctga ggctctagcc acctaaaacc acgtgcccaa    4200
acccaccagt ttaaaacggt gtgtgttcgg aggggtgaaa gcattaagaa gcccagtgcc    4260
ctcctggagt gagacaaggg ctcggcctta aggagctgaa gagtctgggt agcttgttta    4320
gggtacaaga agcctgttct gtccagcttc agtgacacaa gctgctttag ctaaagtccc    4380
gcgggttccg gcatggctag gctgagagca gggatctacc tggcttctca gttctttggt    4440
tggaaggagc aggaaatcag ctcctattct ccagtggaga gatctggcct cagcttgggc    4500
tagagatgcc aaggcctgtg ccaggttccc tgtgccctcc tcgaggtggg cagccatcac    4560
cagccacagt taagccaagc cccccaacat gtattccatc gtgctggtag aagagtcttt    4620
gctgttgctc ccgaaagccg tgctctccag cctggctgcc agggagggtg ggcctcttgg    4680
ttccaggctc ttgaaatagt gcagccttt  cttcctatct ctgtggcttt cagctctgct    4740
tccttggtta ttaggagaat agatgggtga tgtctttcct tatgttgctt tttcaacata    4800
gcagaattaa tgtagggagc taaatccagt ggtgtgtgtg aatgcagaag ggaatgcacc    4860
ccacattccc atgatggaag tctgcgtaac caataaattg tgcctttctc actcaaaaaa    4920
aaaaa                                                              4925

<210> SEQ ID NO 2
<211> LENGTH: 4865
<212> TYPE: PRT
<213> ORGANISM: Mus musculus

<400> SEQUENCE: 2

Gly Gly Cys Ala Ala Thr Thr Thr Cys Thr Gly Ala Gly Ala Gly Gly
 1               5                  10                  15

Cys Ala Ala Cys Ala Gly Gly Cys Gly Gly Cys Ala Gly Gly Thr Cys
                20                  25                  30

Thr Cys Ala Gly Cys Cys Thr Ala Gly Ala Gly Ala Gly Gly Gly Cys
            35                  40                  45

Cys Cys Thr Gly Ala Ala Cys Thr Ala Cys Thr Thr Thr Gly Cys Thr
        50                  55                  60

Gly Gly Ala Gly Thr Gly Thr Cys Cys Gly Thr Cys Cys Thr Gly Gly
```

-continued

```
65                  70                  75                  80

Gly Ala Gly Thr Gly Gly Cys Thr Gly Cys Thr Gly Ala Cys Cys Cys
                85                  90                  95

Ala Gly Thr Cys Cys Ala Gly Gly Ala Gly Ala Cys Cys Cys Ala Thr
            100                 105                 110

Gly Cys Cys Thr Gly Cys Cys Ala Thr Gly Gly Thr Cys Cys Cys Thr
        115                 120                 125

Gly Gly Gly Thr Gly Gly Ala Ala Cys Cys Ala Thr Gly Gly Cys Ala
    130                 135                 140

Ala Cys Ala Thr Cys Ala Cys Cys Cys Gly Cys Thr Cys Cys Ala Ala
145                 150                 155                 160
Gly Gly Cys Ala Gly Ala Gly Gly Ala Gly Cys Thr Ala Cys Thr Thr
                165                 170                 175

Thr Cys Cys Ala Gly Ala Gly Cys Cys Gly Gly Cys Ala Ala Gly Gly
            180                 185                 190

Ala Cys Gly Gly Gly Ala Gly Cys Thr Thr Cys Cys Thr Thr Gly Thr
        195                 200                 205

Gly Cys Gly Thr Gly Cys Cys Ala Gly Cys Gly Ala Gly Thr Cys Cys
    210                 215                 220

Ala Thr Cys Cys Cys Cys Cys Gly Gly Gly Cys Cys Thr Ala Cys Gly
225                 230                 235                 240

Cys Ala Cys Thr Cys Thr Gly Cys Gly Thr Gly Cys Thr Gly Thr Thr
                245                 250                 255

Cys Cys Gly Gly Ala Ala Thr Thr Gly Thr Gly Thr Thr Thr Ala Cys
            260                 265                 270

Ala Cys Thr Thr Ala Cys Ala Gly Gly Ala Thr Thr Cys Thr Gly Cys
        275                 280                 285

Cys Cys Ala Ala Thr Gly Ala Gly Gly Ala Cys Gly Ala Thr Ala Ala
    290                 295                 300

Ala Thr Thr Cys Ala Cys Thr Gly Thr Thr Cys Ala Gly Gly Cys Ala
305                 310                 315                 320

Thr Cys Cys Gly Ala Ala Gly Gly Thr Gly Thr Cys Cys Cys Cys Ala
                325                 330                 335

Thr Gly Ala Gly Gly Thr Thr Cys Thr Thr Cys Ala Cys Gly Ala Ala
            340                 345                 350

Gly Cys Thr Gly Gly Ala Cys Cys Ala Gly Cys Thr Cys Ala Thr Cys
        355                 360                 365

Gly Ala Cys Thr Thr Thr Thr Ala Cys Ala Ala Gly Ala Ala Gly Gly
    370                 375                 380

Ala Ala Ala Ala Cys Ala Thr Gly Gly Gly Gly Cys Thr Gly Gly Thr
385                 390                 395                 400

Gly Ala Cys Cys Cys Ala Cys Cys Thr Gly Cys Ala Gly Thr Ala Cys
                405                 410                 415

Cys Cys Cys Gly Thr Gly Cys Cys Cys Cys Thr Gly Gly Ala Gly Gly
            420                 425                 430

Ala Gly Gly Ala Gly Gly Ala Thr Gly Cys Thr Ala Thr Thr Gly Ala
        435                 440                 445

Thr Gly Ala Gly Gly Cys Thr Gly Ala Gly Gly Ala Gly Gly Ala Cys
    450                 455                 460

Ala Cys Thr Gly Thr Ala Gly Ala Ala Ala Gly Thr Gly Thr Cys Ala
465                 470                 475                 480

Thr Gly Thr Cys Ala Cys Cys Ala Cys Cys Thr Gly Ala Gly Cys Thr
                485                 490                 495
```

-continued

```
Gly Cys Cys Thr Cys Cys Cys Ala Gly Ala Ala Cys Ala Thr Thr
            500                 505                 510
Cys Cys Thr Ala Thr Gly Thr Cys Thr Gly Cys Cys Gly Gly Cys
            515                 520                 525
Cys Cys Ala Gly Cys Gly Ala Gly Gly Cys Cys Ala Ala Gly Ala
            530                 535                 540
Cys Cys Thr Thr Cys Cys Thr Cys Thr Gly Cys Ala Ala Cys Ala
545                 550                 555                 560
Gly Ala Gly Ala Ala Cys Cys Cys Cys Gly Ala Gly Cys Cys Cys
                565                 570                 575
Cys Thr Gly Ala Gly Gly Thr Cys Ala Cys Cys Gly Gly Cys Thr
            580                 585                 590
Gly Ala Gly Thr Cys Thr Cys Thr Cys Cys Gly Ala Gly Ala Cys Ala
            595                 600                 605
Cys Thr Gly Thr Thr Thr Cys Ala Gly Cys Gly Thr Cys Thr Ala Cys
    610                 615                 620
Ala Gly Ala Gly Cys Ala Thr Gly Gly Ala Thr Ala Cys Cys Ala Gly
625                 630                 635                 640
Thr Gly Gly Gly Cys Thr Thr Cys Cys Cys Gly Ala Gly Gly Ala Gly
                645                 650                 655
Cys Ala Cys Cys Thr Gly Ala Ala Ala Gly Cys Cys Ala Thr Cys Cys
            660                 665                 670
Ala Gly Gly Ala Thr Thr Ala Thr Cys Thr Gly Ala Gly Cys Ala Cys
            675                 680                 685
Thr Cys Ala Gly Cys Thr Cys Cys Thr Cys Thr Gly Gly Ala Thr
    690                 695                 700
Thr Cys Cys Gly Ala Cys Thr Thr Thr Thr Gly Ala Ala Gly Ala
705                 710                 715                 720
Cys Gly Gly Gly Cys Thr Cys Cys Ala Gly Cys Ala Ala Cys Cys Thr
                725                 730                 735
Cys Cys Cys Thr Cys Ala Cys Cys Thr Gly Ala Ala Gly Ala Ala Gly
            740                 745                 750
Cys Thr Gly Ala Thr Gly Thr Cys Ala Cys Thr Gly Cys Thr Cys Thr
    755                 760                 765
Gly Cys Ala Ala Gly Gly Ala Gly Gly Cys Thr Cys Ala Thr Gly Gly
    770                 775                 780
Gly Gly Ala Ala Gly Thr Cys Ala Thr Cys Ala Gly Gly Ala Cys Thr
785                 790                 795                 800
Cys Thr Gly Cys Cys Ala Thr Cys Cys Cys Thr Gly Gly Ala Gly Thr
            805                 810                 815
Cys Thr Cys Thr Gly Cys Ala Gly Ala Gly Gly Thr Thr Gly Thr Thr
    820                 825                 830
Thr Gly Ala Cys Cys Ala Ala Cys Ala Gly Cys Thr Cys Thr Cys Cys
            835                 840                 845
Cys Cys Ala Gly Gly Cys Cys Thr Thr Cys Gly Cys Cys Ala Cys
    850                 855                 860
Gly Ala Cys Cys Thr Cys Ala Gly Gly Thr Gly Cys Cys Cys Gly Gly
865                 870                 875                 880
Ala Gly Ala Gly Gly Cys Cys Ala Gly Thr Cys Cys Cys Ala Thr Cys
                885                 890                 895
Ala Cys Cys Ala Thr Gly Gly Thr Thr Gly Cys Cys Ala Ala Ala Cys
            900                 905                 910
Thr Cys Ala Gly Cys Cys Ala Ala Thr Thr Gly Ala Cys Ala Ala Gly
    915                 920                 925
```

-continued

```
Thr Cys Thr Gly Cys Thr Gly Thr Cys Thr Thr Cys Cys Ala Thr Thr
    930                 935                 940

Gly Ala Ala Gly Ala Thr Ala Ala Gly Gly Thr Cys Ala Ala Gly Thr
945                 950                 955                 960

Cys Cys Thr Thr Gly Cys Thr Gly Cys Ala Cys Gly Ala Gly Gly Gly
                965                 970                 975

Cys Thr Cys Ala Gly Ala Ala Thr Cys Thr Ala Cys Cys Ala Ala Cys
            980                 985                 990

Ala Gly Gly Cys Gly Thr Thr Cys  Cys Cys Thr Thr Ala  Thr Cys Cys
        995                 1000                1005

Cys Thr  Cys Cys Gly Gly Thr  Cys Ala Cys Cys Thr  Thr Thr Gly
    1010                1015                1020

Ala Gly  Gly Thr Gly Ala Ala  Gly Thr Cys Ala Gly  Ala Gly Thr
    1025                1030                1035

Cys Cys  Cys Thr Gly Gly Gly  Cys Ala Thr Thr Cys  Cys Thr Cys
    1040                1045                1050

Ala Gly  Ala Ala Ala Ala Thr  Gly Cys Ala Thr Cys  Thr Cys Ala
    1055                1060                1065

Ala Ala  Gly Thr Gly Gly Ala  Cys Gly Thr Thr Gly  Ala Gly Thr
    1070                1075                1080

Cys Thr  Gly Gly Gly Ala Ala  Ala Cys Thr Gly Ala  Thr Cys Gly
    1085                1090                1095

Thr Thr  Ala Ala Gly Ala Ala  Gly Thr Cys Cys Ala  Ala Gly Gly
    1100                1105                1110

Ala Thr  Gly Gly Thr Thr Cys  Thr Gly Ala Gly Gly  Ala Cys Ala
    1115                1120                1125

Ala Gly  Thr Thr Cys Thr Ala  Cys Ala Gly Cys Cys  Ala Cys Ala
    1130                1135                1140

Ala Ala  Ala Ala Ala Ala Thr  Cys Cys Thr Gly Cys  Ala Gly Cys
    1145                1150                1155

Thr Cys  Ala Thr Thr Ala Ala  Gly Thr Cys Cys Cys  Ala Gly Ala
    1160                1165                1170

Ala Gly  Thr Thr Thr Cys Thr  Ala Ala Ala Cys Ala  Ala Gly Thr
    1175                1180                1185

Thr Gly  Gly Thr Gly Ala Thr  Thr Thr Thr Gly Gly  Thr Gly Gly
    1190                1195                1200

Ala Gly  Ala Cys Gly Gly Ala  Gly Ala Ala Gly Gly  Ala Gly Ala
    1205                1210                1215

Ala Ala  Ala Thr Cys Cys Thr  Gly Ala Gly Gly Ala  Ala Gly Gly
    1220                1225                1230

Ala Ala  Thr Ala Thr Gly Thr  Thr Thr Thr Thr Gly  Cys Thr Gly
    1235                1240                1245

Ala Cys  Thr Cys Thr Ala Ala  Gly Ala Ala Ala Ala  Gly Ala Gly
    1250                1255                1260

Ala Ala  Gly Gly Cys Thr Thr  Cys Thr Gly Thr Cys  Ala Ala Cys
    1265                1270                1275

Thr Cys  Cys Thr Gly Cys Ala  Gly Cys Ala Gly Ala  Thr Gly Ala
    1280                1285                1290

Ala Gly  Ala Ala Cys Ala Ala  Gly Cys Ala Thr Thr  Cys Gly Gly
    1295                1300                1305

Ala Gly  Cys Ala Gly Cys Cys  Ala Gly Ala Gly Cys  Cys Thr Gly
    1310                1315                1320

Ala Cys  Ala Thr Gly Ala Thr  Cys Ala Cys Cys Ala  Thr Cys Thr
```

-continued

```
    1325                1330                1335

Thr Cys  Ala Thr Thr Gly Gly  Cys Ala Cys Thr Thr  Gly Gly Ala
    1340                1345                1350

Ala Cys  Ala Thr Gly Gly Gly  Thr Ala Ala Thr Gly  Cys Ala Cys
    1355                1360                1365

Cys Cys  Cys Cys Thr Cys Cys  Cys Ala Ala Gly Ala  Ala Gly Ala
    1370                1375                1380

Thr Cys  Ala Cys Gly Thr Cys  Cys Thr Gly Gly Thr  Thr Thr Cys
    1385                1390                1395

Thr Cys  Thr Cys Cys Ala Ala  Gly Gly Gly Gly Cys  Ala Gly Gly
    1400                1405                1410

Gly Ala  Ala Ala Gly Ala Cys  Ala Cys Gly Gly Gly  Ala Cys Gly
    1415                1420                1425

Ala Cys  Thr Cys Thr Gly Cys  Thr Gly Ala Cys Thr  Ala Cys Ala
    1430                1435                1440

Thr Cys  Cys Cys Cys Cys Ala  Thr Gly Ala Cys Ala  Thr Cys Thr
    1445                1450                1455

Ala Thr  Gly Thr Gly Ala Thr  Thr Gly Gly Cys Ala  Cys Cys Cys
    1460                1465                1470

Ala Gly  Gly Ala Gly Gly Ala  Thr Cys Cys Cys Cys  Thr Thr Gly
    1475                1480                1485

Gly Ala  Gly Ala Gly Ala Ala  Gly Gly Ala Gly Thr  Gly Gly Cys
    1490                1495                1500

Thr Gly  Gly Ala Gly Cys Thr  Ala Cys Thr Cys Ala  Gly Gly Cys
    1505                1510                1515

Ala Cys  Thr Cys Cys Cys Thr  Gly Cys Ala Ala Gly  Ala Ala Gly
    1520                1525                1530

Thr Cys  Ala Cys Cys Ala Gly  Cys Ala Thr Gly Ala  Cys Ala Thr
    1535                1540                1545

Thr Thr  Ala Ala Ala Ala Cys  Ala Gly Thr Thr Gly  Cys Cys Ala
    1550                1555                1560

Thr Cys  Cys Ala Cys Ala Cys  Cys Cys Thr Cys Thr  Gly Gly Ala
    1565                1570                1575

Ala Cys  Ala Thr Thr Cys Gly  Cys Ala Thr Ala Gly  Thr Gly Gly
    1580                1585                1590

Thr Gly  Cys Thr Thr Gly Cys  Cys Ala Ala Gly Cys  Cys Ala Gly
    1595                1600                1605

Ala Gly  Cys Ala Thr Gly Ala  Gly Ala Ala Thr Cys  Gly Gly Ala
    1610                1615                1620

Thr Cys  Ala Gly Cys Cys Ala  Thr Ala Thr Cys Thr  Gly Cys Ala
    1625                1630                1635

Cys Thr  Gly Ala Cys Ala Ala  Cys Gly Thr Gly Ala  Ala Gly Ala
    1640                1645                1650

Cys Ala  Gly Gly Cys Ala Thr  Cys Gly Cys Cys Ala  Ala Cys Ala
    1655                1660                1665

Cys Cys  Cys Thr Gly Gly Gly  Ala Ala Ala Cys Ala  Ala Gly Gly
    1670                1675                1680

Gly Ala  Gly Cys Ala Gly Cys  Gly Gly Gly Ala Gly  Thr Gly Thr
    1685                1690                1695

Cys Cys  Thr Thr Cys Ala Thr  Gly Thr Thr Cys Ala  Thr Thr Gly
    1700                1705                1710

Gly Ala  Ala Cys Cys Thr Cys  Cys Thr Thr Gly Gly  Gly Gly Thr
    1715                1720                1725
```

```
Thr Cys Gly Thr Cys Ala Ala Cys Ala Gly Cys Ala Cys Thr
1730                1735                1740

Thr Gly Ala Cys Thr Thr Cys Thr Gly Gly Ala Ala Gly Thr Gly
1745                1750                1755

Ala Ala Ala Ala Ala Ala Ala Gly Cys Thr Cys Ala Gly Gly Ala
1760                1765                1770

Gly Ala Ala Ala Thr Cys Ala Ala Ala Cys Thr Ala Thr Ala
1775                1780                1785

Thr Gly Ala Ala Cys Ala Thr Cys Cys Thr Gly Cys Gly Gly Thr
1790                1795                1800

Thr Cys Cys Thr Gly Gly Cys Cys Cys Thr Gly Gly Gly Ala Gly
1805                1810                1815

Ala Cys Ala Ala Gly Ala Ala Gly Cys Thr Ala Ala Gly Cys Cys
1820                1825                1830

Cys Ala Thr Thr Thr Ala Ala Cys Ala Thr Cys Ala Cys Cys Cys
1835                1840                1845

Ala Cys Cys Gly Cys Thr Thr Cys Ala Cys Cys Cys Ala Cys Cys
1850                1855                1860

Thr Cys Thr Thr Cys Thr Gly Gly Cys Thr Thr Gly Gly Gly Gly
1865                1870                1875

Ala Thr Cys Thr Cys Ala Ala Cys Thr Ala Cys Cys Gly Cys Gly
1880                1885                1890

Thr Gly Gly Ala Gly Cys Thr Gly Cys Cys Ala Cys Thr Thr
1895                1900                1905

Gly Gly Gly Ala Gly Gly Cys Ala Gly Ala Gly Gly Cys Cys Ala
1910                1915                1920

Thr Cys Ala Thr Cys Cys Ala Gly Ala Ala Gly Ala Thr Cys Ala
1925                1930                1935

Ala Gly Cys Ala Ala Cys Ala Gly Cys Ala Gly Thr Ala Thr Thr
1940                1945                1950

Cys Ala Gly Ala Cys Cys Thr Thr Cys Thr Gly Cys Cys Cys
1955                1960                1965

Ala Cys Gly Ala Cys Cys Ala Ala Cys Thr Gly Cys Thr Cys Cys
1970                1975                1980

Thr Gly Gly Ala Gly Ala Gly Gly Ala Ala Gly Ala Cys Cys
1985                1990                1995

Ala Gly Ala Ala Gly Gly Thr Cys Thr Thr Cys Cys Thr Gly Cys
2000                2005                2010

Ala Cys Thr Thr Thr Gly Ala Gly Gly Ala Gly Gly Ala Ala Gly
2015                2020                2025

Ala Gly Ala Thr Cys Ala Cys Cys Thr Thr Cys Gly Cys Cys Cys
2030                2035                2040

Cys Cys Ala Cys Cys Thr Ala Thr Cys Gly Ala Thr Thr Thr Gly
2045                2050                2055

Ala Ala Ala Gly Ala Cys Thr Gly Ala Cys Cys Cys Gly Gly Gly
2060                2065                2070

Ala Cys Ala Ala Gly Thr Ala Thr Gly Cys Ala Thr Ala Cys Ala
2075                2080                2085

Cys Gly Ala Ala Gly Cys Ala Gly Ala Ala Ala Gly Cys Ala Ala
2090                2095                2100

Cys Ala Gly Gly Gly Ala Thr Gly Ala Ala Gly Thr Ala Cys Ala
2105                2110                2115

Ala Cys Thr Thr Gly Cys Cys Gly Thr Cys Cys Thr Gly Gly Thr
2120                2125                2130
```

```
Gly Cys  Gly Ala Cys Cys Gly  Ala Gly Thr Cys Cys  Thr Cys Thr
    2135                 2140                 2145

Gly Gly  Ala Ala Gly Thr Cys  Thr Thr Ala Cys Cys  Cys Gly Cys
    2150                 2155                 2160

Thr Gly  Gly Thr Gly Cys Ala  Thr Gly Thr Gly Gly  Thr Cys Thr
    2165                 2170                 2175

Gly Thr  Cys Ala Gly Thr Cys  Cys Thr Ala Thr Gly  Gly Cys Ala
    2180                 2185                 2190

Gly Thr  Ala Cys Cys Ala Gly  Thr Gly Ala Cys Ala  Thr Cys Ala
    2195                 2200                 2205

Thr Gly  Ala Cys Gly Ala Gly  Thr Gly Ala Cys Cys  Ala Cys Ala
    2210                 2215                 2220

Gly Cys  Cys Cys Thr Gly Thr  Cys Thr Thr Thr Gly  Cys Cys Ala
    2225                 2230                 2235

Cys Gly  Thr Thr Thr Gly Ala  Ala Gly Cys Ala Gly  Gly Ala Gly
    2240                 2245                 2250

Thr Cys  Ala Cys Ala Thr Cys  Thr Cys Ala Ala Thr  Thr Cys Gly
    2255                 2260                 2265

Thr Cys  Thr Cys Cys Ala Ala  Gly Ala Ala Thr Gly  Gly Thr Cys
    2270                 2275                 2280

Cys Thr  Gly Gly Cys Ala Cys  Thr Gly Thr Ala Gly  Ala Thr Ala
    2285                 2290                 2295

Gly Cys  Cys Ala Ala Gly Gly  Gly Cys Ala Gly Ala  Thr Cys Gly
    2300                 2305                 2310

Ala Gly  Thr Thr Thr Cys Thr  Thr Gly Cys Ala Thr  Gly Cys Thr
    2315                 2320                 2325

Ala Cys  Gly Cys Cys Ala Cys  Ala Cys Thr Gly Ala  Ala Gly Ala
    2330                 2335                 2340

Cys Cys  Ala Ala Gly Thr Cys  Cys Cys Ala Gly Ala  Cys Thr Ala
    2345                 2350                 2355

Ala Gly  Thr Thr Cys Thr Ala  Cys Thr Thr Gly Gly  Ala Gly Thr
    2360                 2365                 2370

Thr Cys  Cys Ala Cys Thr Cys  Ala Ala Gly Cys Thr  Gly Cys Thr
    2375                 2380                 2385

Thr Ala  Gly Ala Gly Ala Gly  Thr Thr Thr Thr Gly  Thr Cys Ala
    2390                 2395                 2400

Ala Gly  Ala Gly Thr Cys Ala  Gly Gly Ala Ala Gly  Gly Ala Gly
    2405                 2410                 2415

Ala Gly  Ala Ala Thr Gly Ala  Ala Gly Ala Gly Gly  Gly Ala Ala
    2420                 2425                 2430

Gly Thr  Gly Ala Ala Gly Gly  Ala Gly Ala Gly Cys  Thr Gly Gly
    2435                 2440                 2445

Thr Gly  Gly Thr Ala Cys Gly  Gly Thr Thr Thr Gly  Gly Ala Gly
    2450                 2455                 2460

Ala Gly  Ala Cys Thr Cys Thr  Thr Cys Cys Cys Ala  Ala Gly Cys
    2465                 2470                 2475

Thr Ala  Ala Ala Gly Cys Cys  Cys Ala Thr Thr Ala  Thr Cys Thr
    2480                 2485                 2490

Cys Thr  Gly Ala Cys Cys Cys  Cys Gly Ala Gly Thr  Ala Cys Thr
    2495                 2500                 2505

Thr Ala  Cys Thr Gly Gly Ala  Cys Cys Ala Gly Cys  Ala Thr Ala
    2510                 2515                 2520

Thr Cys  Cys Thr Gly Ala Thr  Cys Ala Gly Cys Ala  Thr Thr Ala
```

-continued

```
    2525                2530                2535

Ala Ala  Thr Cys Cys Thr Cys  Thr Gly Ala Cys Ala  Gly Thr Gly
    2540                2545                2550

Ala Cys  Gly Ala Gly Thr Cys  Cys Thr Ala Thr Gly  Gly Thr Gly
    2555                2560                2565

Ala Ala  Gly Gly Cys Thr Gly  Cys Ala Thr Thr Gly  Cys Cys Cys
    2570                2575                2580

Thr Thr  Cys Gly Cys Thr Thr  Gly Gly Ala Gly Ala  Cys Cys Ala
    2585                2590                2595

Cys Ala  Gly Ala Gly Gly Cys  Thr Cys Ala Gly Cys  Ala Thr Cys
    2600                2605                2610

Cys Thr  Ala Thr Cys Thr Ala  Cys Ala Cys Gly Cys  Cys Thr Cys
    2615                2620                2625

Thr Cys  Ala Cys Cys Cys Ala  Cys Cys Ala Thr Gly  Gly Gly Gly
    2630                2635                2640

Ala Gly  Ala Thr Gly Ala Cys  Thr Gly Gly Cys Cys  Ala Cys Thr
    2645                2650                2655

Thr Cys  Ala Gly Gly Gly Gly  Ala Gly Ala Gly Ala  Thr Thr Ala
    2660                2665                2670

Ala Gly  Cys Thr Gly Cys Ala  Gly Ala Cys Cys Thr  Cys Cys Cys
    2675                2680                2685

Ala Gly  Gly Gly Cys Ala Ala  Gly Ala Thr Gly Ala  Gly Gly Gly
    2690                2695                2700

Ala Gly  Ala Ala Gly Cys Thr  Cys Thr Ala Thr Gly  Ala Cys Thr
    2705                2710                2715

Thr Thr  Gly Thr Gly Ala Ala  Gly Ala Cys Ala Gly  Ala Gly Cys
    2720                2725                2730

Gly Gly  Gly Ala Thr Gly Ala  Ala Thr Cys Cys Ala  Gly Thr Gly
    2735                2740                2745

Gly Ala  Ala Thr Gly Ala Ala  Ala Thr Gly Cys Thr  Thr Gly Ala
    2750                2755                2760

Ala Gly  Ala Ala Cys Cys Thr  Cys Ala Cys Cys Ala  Gly Cys Cys
    2765                2770                2775

Ala Thr  Gly Ala Cys Cys Cys  Thr Ala Thr Gly Ala  Gly Gly Cys
    2780                2785                2790

Ala Ala  Thr Gly Gly Gly Ala  Gly Cys Cys Thr Thr  Cys Thr Gly
    2795                2800                2805

Gly Cys  Ala Gly Gly Gly Thr  Cys Cys Cys Thr Gly  Cys Ala Thr
    2810                2815                2820

Gly Thr  Gly Gly Thr Gly Thr  Cys Thr Cys Cys Ala  Gly Cys Cys
    2825                2830                2835

Thr Cys  Ala Ala Thr Gly Ala  Gly Ala Thr Gly Ala  Thr Cys Ala
    2840                2845                2850

Ala Thr  Cys Cys Ala Ala Ala  Cys Thr Ala Cys Ala  Thr Thr Gly
    2855                2860                2865

Gly Thr  Ala Thr Gly Gly Gly  Gly Cys Cys Thr Thr  Thr Thr Gly
    2870                2875                2880

Gly Ala  Cys Ala Gly Cys Cys  Cys Cys Thr Gly Cys  Ala Thr Gly
    2885                2890                2895

Gly Gly  Ala Ala Ala Thr Cys  Ala Ala Cys Cys Cys  Thr Gly Thr
    2900                2905                2910

Cys Cys  Cys Cys Ala Gly Ala  Thr Cys Ala Gly Cys  Ala Ala Cys
    2915                2920                2925
```

-continued

```
Thr Cys Ala Cys Ala Gly Cys Thr Thr Gly Gly Ala  Gly Thr Thr
    2930                2935                2940

Ala Thr Gly Ala Cys Cys Ala Gly Cys Thr Ala Cys  Cys Cys Ala
    2945                2950                2955

Ala Ala Gly Ala Cys Thr Cys Cys Thr Cys Cys Cys  Thr Gly Gly
    2960                2965                2970

Gly Gly Cys Cys Thr Gly Gly Ala Gly Gly Gly Gly  Gly Gly Gly
    2975                2980                2985

Ala Gly Gly Gly Thr Cys Cys Thr Cys Cys Ala Ala  Cys Cys Cys
    2990                2995                3000

Cys Thr Cys Cys Cys Thr Cys Cys Cys Ala Ala Cys  Cys Ala Cys
    3005                3010                3015

Cys Thr Cys Thr Gly Thr Cys Gly Cys Cys Ala Ala  Ala Gly Ala
    3020                3025                3030

Ala Gly Thr Thr Thr Thr Cys Ala Thr Cys Thr Thr  Cys Cys Ala
    3035                3040                3045

Cys Ala Gly Cys Cys Ala Ala Cys Cys Gly Ala Gly  Gly Thr Cys
    3050                3055                3060

Cys Cys Thr Gly Cys Cys Cys Ala Gly Gly Gly Thr  Thr Gly Cys
    3065                3070                3075

Ala Ala Gly Ala Gly Gly Cys Ala Ala Gly Ala Cys  Cys Thr Gly
    3080                3085                3090

Gly Gly Gly Ala Thr Cys Thr Gly Gly Gly Ala Ala  Ala Gly Gly
    3095                3100                3105

Thr Gly Gly Ala Ala Gly Cys Thr Cys Thr Gly Cys  Thr Cys Cys
    3110                3115                3120

Ala Gly Gly Ala Gly Gly Ala Cys Cys Thr Gly Cys  Thr Gly Cys
    3125                3130                3135

Thr Gly Ala Cys Gly Ala Ala Gly Cys Cys Cys Gly  Ala Gly Ala
    3140                3145                3150

Thr Gly Thr Thr Thr Gly Ala Gly Ala Ala Cys Cys  Cys Ala Cys
    3155                3160                3165

Thr Gly Thr Ala Thr Gly Gly Ala Thr Cys Cys Gly  Thr Gly Ala
    3170                3175                3180

Gly Thr Thr Cys Cys Thr Cys Cys Cys Thr Ala Ala  Gly Cys
    3185                3190                3195

Thr Gly Gly Thr Gly Cys Cys Ala Gly Gly Ala Ala  Ala Ala Gly
    3200                3205                3210

Ala Gly Cys Ala Gly Gly Ala Gly Thr Cys Thr Cys  Cys Cys Ala
    3215                3220                3225

Ala Gly Ala Thr Gly Cys Thr Gly Cys Gly Gly Ala  Ala Gly Gly
    3230                3235                3240

Ala Gly Cys Cys Cys Cys Gly Cys Cys Cys Thr Gly  Thr Cys
    3245                3250                3255

Cys Ala Gly Ala Cys Cys Ala Gly Gly Ala Ala Thr  Cys Thr
    3260                3265                3270

Cys Ala Thr Cys Ala Cys Cys Ala Gly Cys Ala Thr  Cys Gly
    3275                3280                3285

Thr Gly Cys Thr Cys Cys Cys Ala Ala Ala Gly Cys  Cys Cys
    3290                3295                3300

Ala Ala Gly Ala Gly Gly Thr Gly Gly Ala Gly Ala  Gly Thr Gly
    3305                3310                3315

Thr Cys Ala Ala Gly Gly Gly Ala Cys Ala Ala Gly  Cys Ala
    3320                3325                3330
```

```
Ala Ala Cys Ala Gly Gly Cys Cys Cys Cys Thr Gly Thr Gly Cys
    3335                3340                3345
Cys Thr Gly Thr Cys Cys Thr Thr Gly Gly Cys Cys Cys Cys Ala
    3350                3355                3360
Cys Ala Cys Cys Cys Cys Gly Gly Ala Thr Cys Cys Gly Cys Thr
    3365                3370                3375
Cys Cys Thr Thr Thr Ala Cys Cys Thr Gly Thr Cys Thr Cys Thr
    3380                3385                3390
Cys Thr Thr Cys Thr Gly Cys Thr Gly Ala Gly Gly Gly Cys Ala
    3395                3400                3405
Gly Ala Ala Thr Gly Ala Cys Cys Ala Gly Thr Gly Gly Gly Gly
    3410                3415                3420
Ala Cys Ala Ala Gly Ala Gly Cys Cys Ala Ala Gly Gly Gly Ala
    3425                3430                3435
Ala Gly Cys Cys Cys Ala Ala Gly Gly Cys Cys Thr Cys Ala Gly
    3440                3445                3450
Cys Cys Ala Gly Thr Thr Cys Cys Cys Ala Ala Gly Cys Cys Cys
    3455                3460                3465
Cys Ala Gly Thr Gly Cys Cys Ala Gly Thr Cys Ala Ala Gly Ala
    3470                3475                3480
Gly Gly Cys Cys Thr Gly Thr Cys Ala Ala Gly Cys Cys Thr Thr
    3485                3490                3495
Cys Cys Ala Gly Gly Thr Cys Ala Gly Ala Ala Ala Thr Gly Ala
    3500                3505                3510
Gly Cys Cys Ala Gly Cys Ala Gly Ala Cys Ala Ala Cys Ala Cys
    3515                3520                3525
Cys Cys Ala Thr Cys Cys Cys Ala Gly Cys Thr Cys Cys Ala Cys
    3530                3535                3540
Gly Gly Cys Cys Ala Cys Cys Cys Thr Gly Cys Cys Ala Gly
    3545                3550                3555
Thr Cys Ala Ala Gly Ala Gly Thr Cys Cys Thr Gly Cys Thr Gly
    3560                3565                3570
Thr Cys Cys Thr Gly Cys Ala Gly Cys Thr Gly Cys Ala Ala Cys
    3575                3580                3585
Ala Thr Thr Cys Cys Ala Ala Ala Gly Gly Cys Ala Gly Ala Gly
    3590                3595                3600
Ala Cys Thr Ala Cys Cys Gly Thr Gly Ala Cys Ala Ala Cys Ala
    3605                3610                3615
Cys Ala Gly Ala Ala Cys Thr Cys Cys Cys Cys Ala Cys Cys
    3620                3625                3630
Ala Thr Gly Gly Cys Ala Ala Gly Cys Ala Cys Cys Gly Cys Cys
    3635                3640                3645
Ala Ala Gly Ala Gly Gly Ala Gly Gly Gly Gly Cys Thr Gly Cys
    3650                3655                3660
Thr Thr Gly Gly Cys Ala Gly Gly Ala Cys Thr Gly Cys Cys Ala
    3665                3670                3675
Thr Gly Cys Ala Gly Thr Gly Ala Gly Cys Thr Gly Cys Thr Gly
    3680                3685                3690
Gly Thr Gly Ala Thr Cys Gly Gly Ala Gly Cys Cys Thr Gly Gly
    3695                3700                3705
Ala Gly Gly Ala Ala Cys Ala Gly Cys Ala Cys Ala Ala Ala Gly
    3710                3715                3720
Cys Ala Gly Ala Cys Cys Thr Gly Cys Gly Cys Cys Thr Cys Thr
```

-continued

```
              3725                3730                3735
Cys Thr Cys Ala Gly Gly Ala Thr Gly Cys Cys Thr Cys Thr Cys
              3740                3745                3750
Thr Cys Ala Gly Gly Ala Thr Gly Cys Cys Thr Cys Thr Thr Gly
              3755                3760                3765
Gly Ala Gly Gly Ala Cys Cys Thr Cys Thr Gly Cys Thr Ala
              3770                3775                3780
Gly Cys Thr Cys Thr Thr Cys Thr Thr Gly Cys Cys Thr Ala Gly
              3785                3790                3795
Cys Thr Thr Cys Ala Ala Gly Thr Cys Cys Cys Ala Gly Gly Cys
              3800                3805                3810
Thr Gly Thr Gly Thr Ala Thr Thr Thr Thr Thr Thr Thr Cys
              3815                3820                3825
Ala Gly Gly Ala Ala Ala Cys Gly Gly Cys Cys Thr Cys Ala Cys
              3830                3835                3840
Thr Thr Cys Thr Cys Thr Gly Thr Gly Gly Thr Cys Cys Ala Ala
              3845                3850                3855
Gly Ala Ala Gly Thr Gly Thr Gly Cys Thr Gly Cys Thr Gly Gly
              3860                3865                3870
Cys Thr Gly Cys Cys Ala Cys Ala Cys Thr Gly Thr Gly Cys Gly
              3875                3880                3885
Gly Cys Ala Gly Ala Thr Gly Cys Thr Ala Ala Gly Cys Thr
              3890                3895                3900
Gly Gly Ala Thr Gly Ala Cys Ala Ala Ala Cys Gly Cys Ala Cys
              3905                3910                3915
Gly Cys Cys Ala Thr Ala Cys Ala Gly Ala Cys Ala Gly Cys Ala
              3920                3925                3930
Gly Ala Cys Ala Gly Cys Gly Gly Cys Ala Cys Thr Gly Gly Gly
              3935                3940                3945
Thr Cys Thr Cys Ala Gly Ala Ala Cys Thr Thr Gly Gly Ala Thr
              3950                3955                3960
Thr Cys Cys Thr Gly Gly Gly Cys Cys Thr Thr Cys Thr Thr Cys
              3965                3970                3975
Cys Ala Gly Thr Cys Gly Cys Cys Gly Thr Thr Thr Ala Ala
              3980                3985                3990
Ala Gly Ala Ala Ala Gly Gly Ala Ala Cys Thr Ala Ala Cys Gly
              3995                4000                4005
Gly Ala Gly Cys Thr Gly Cys Thr Cys Ala Thr Cys Cys Gly Ala
              4010                4015                4020
Gly Gly Gly Thr Gly Ala Ala Gly Ala Thr Ala Thr Ala Ala Ala
              4025                4030                4035
Thr Ala Ala Thr Ala Ala Thr Ala Thr Thr Ala Thr Thr Ala Ala
              4040                4045                4050
Thr Ala Ala Thr Ala Ala Thr Ala Ala Cys Ala Gly Thr Cys Ala
              4055                4060                4065
Gly Gly Thr Gly Cys Cys Ala Thr Gly Thr Gly Cys Thr Gly Thr
              4070                4075                4080
Gly Thr Thr Ala Ala Gly Thr Gly Cys Thr Thr Ala Thr Gly
              4085                4090                4095
Ala Ala Cys Ala Thr Thr Thr Gly Thr Cys Gly Gly Cys Thr
              4100                4105                4110
Gly Gly Cys Cys Thr Cys Cys Ala Gly Thr Gly Cys Thr Gly Ala
              4115                4120                4125
```

```
Gly Gly Thr Gly Cys Cys Ala Gly Thr Cys Ala Gly Cys Cys Thr
         4130                4135                4140
Gly Ala Ala Cys Cys Cys Thr Ala Thr Gly Cys Cys Cys Ala Gly
         4145                4150                4155
Gly Cys Cys Cys Ala Cys Thr Ala Ala Thr Cys Cys Cys Ala Ala
         4160                4165                4170
Ala Thr Gly Gly Thr Gly Gly Thr Cys Cys Thr Gly Ala Gly
         4175                4180                4185
Ala Thr Gly Thr Thr Thr Thr Ala Ala Ala Ala Gly Cys
         4190                4195                4200
Ala Thr Thr Ala Ala Ala Gly Ala Ala Ala Cys Cys Ala Thr
         4205                4210                4215
Cys Gly Gly Thr Cys Thr Cys Thr Thr Ala Gly Ala Gly Cys Thr
         4220                4225                4230
Ala Ala Cys Cys Gly Gly Cys Cys Gly Gly Cys Thr Cys Thr
         4235                4240                4245
Ala Cys Thr Gly Cys Ala Gly Gly Gly Ala Cys Cys Cys Gly Ala
         4250                4255                4260
Ala Cys Ala Gly Thr Cys Thr Gly Cys Ala Thr Gly Gly Cys Thr
         4265                4270                4275
Ala Ala Gly Thr Gly Gly Cys Ala Cys Ala Ala Gly Gly Ala Gly
         4280                4285                4290
Cys Cys Thr Gly Gly Cys Cys Thr Gly Thr Cys Cys Ala Gly
         4295                4300                4305
Cys Thr Thr Cys Ala Gly Ala Gly Ala Thr Cys Cys Ala Ala Gly
         4310                4315                4320
Cys Thr Gly Cys Thr Thr Thr Thr Gly Cys Thr Gly Gly Gly
         4325                4330                4335
Gly Thr Thr Cys Thr Gly Thr Cys Ala Cys Ala Gly Gly Cys Cys
         4340                4345                4350
Thr Gly Ala Thr Cys Cys Thr Cys Thr Thr Gly Gly Thr Thr Thr
         4355                4360                4365
Thr Thr Ala Thr Gly Gly Gly Thr Thr Thr Cys Ala Ala Gly
         4370                4375                4380
Thr Cys Thr Gly Cys Ala Gly Ala Gly Thr Cys Ala Gly Ala
         4385                4390                4395
Ala Ala Thr Cys Ala Gly Cys Thr Cys Thr Ala Ala Cys Thr Cys
         4400                4405                4410
Gly Cys Cys Ala Gly Thr Gly Ala Ala Gly Ala Gly Ala Thr Cys
         4415                4420                4425
Thr Gly Gly Cys Cys Thr Thr Ala Ala Cys Thr Thr Ala Ala Gly
         4430                4435                4440
Cys Cys Ala Gly Cys Cys Ala Cys Gly Thr Cys Ala Gly Gly Cys
         4445                4450                4455
Cys Cys Cys Thr Gly Cys Thr Gly Ala Gly Cys Cys Thr Ala Thr
         4460                4465                4470
Gly Gly Ala Cys Cys Ala Ala Thr Ala Ala Ala Thr Ala Cys Thr
         4475                4480                4485
Cys Cys Cys Cys Gly Thr Gly Cys Cys Ala Cys Thr Gly Gly Ala
         4490                4495                4500
Gly Gly Thr Gly Gly Gly Cys Ala Gly Cys Thr Ala Thr Cys Ala
         4505                4510                4515
Cys Cys Ala Thr Ala Cys Cys Cys Thr Gly Ala Gly Thr Thr Gly
         4520                4525                4530
```

Gly Gly Cys Cys Ala Ala Gly Cys Cys Ala Cys Cys Cys
    4535            4540            4545

Ala Cys Cys Cys Cys Thr Ala Cys Cys Cys Thr Gly Cys Ala Ala
    4550            4555            4560

Cys Ala Thr Thr Thr Cys Thr Gly Ala Thr Gly Thr Trp Cys Thr
    4565            4570            4575

Gly Ala Gly Gly Ala Ala Gly Ala Gly Thr Cys Thr Cys Cys Ala
    4580            4585            4590

Cys Cys Ala Thr Ala Gly Thr Cys Cys Cys Cys Ala Ala Gly Gly
    4595            4600            4605

Gly Cys Thr Gly Ala Gly Thr Thr Cys Thr Cys Cys Ala Gly Cys
    4610            4615            4620

Cys Thr Gly Cys Thr Ala Thr Cys Ala Gly Gly Gly Ala Ala Gly
    4625            4630            4635

Gly Thr Gly Ala Gly Cys Ala Thr Thr Gly Gly Thr Cys Cys Cys
    4640            4645            4650

Ala Gly Gly Cys Thr Cys Thr Cys Ala Ala Ala Thr Ala Gly
    4655            4660            4665

Thr Gly Cys Ala Gly Cys Cys Thr Cys Thr Thr Thr Cys Thr Thr Cys
    4670            4675            4680

Cys Cys Ala Ala Gly Cys Thr Cys Thr Gly Gly Gly Gly Thr Gly
    4685            4690            4695

Cys Ala Cys Cys Cys Thr Gly Thr Gly Thr Cys Cys Thr Thr Gly
    4700            4705            4710

Gly Thr Thr Ala Cys Cys Ala Gly Gly Ala Gly Ala Cys Thr Ala
    4715            4720            4725

Gly Gly Gly Thr Thr Gly Thr Gly Ala Thr Ala Thr Cys Thr Thr
    4730            4735            4740

Thr Thr Cys Thr Thr Gly Thr Cys Thr Thr Gly Cys Thr Thr Thr
    4745            4750            4755

Thr Thr Gly Ala Thr Ala Thr Ala Thr Cys Ala Gly Gly Ala Thr
    4760            4765            4770

Thr Ala Ala Thr Gly Thr Ala Gly Gly Ala Ala Ala Cys Cys Ala
    4775            4780            4785

Gly Ala Cys Cys Thr Ala Gly Ala Thr Thr Ala Thr Thr Cys Ala
    4790            4795            4800

Gly Gly Ala Gly Ala Gly Thr Ala Gly Gly Thr Ala Thr Ala Thr
    4805            4810            4815

Cys Cys Cys Cys Thr Gly Thr Gly Thr Thr Cys Cys Cys Ala
    4820            4825            4830

Gly Thr Cys Thr Gly Ala Gly Thr Gly Ala Cys Cys Ala Ala Thr
    4835            4840            4845

Ala Ala Ala Ala Thr Thr Gly Thr Gly Cys Cys Thr Thr Thr Cys
    4850            4855            4860

Thr Ala
    4865

<210> SEQ ID NO 3
<211> LENGTH: 19
<212> TYPE: DNA
<213> ORGANISM: Homo sapiens

<400> SEQUENCE: 3
gcctgttgtc atccattga                                         19

```
<210> SEQ ID NO 4
<211> LENGTH: 19
<212> TYPE: DNA
<213> ORGANISM: Homo sapiens

<400> SEQUENCE: 4
ataagttggt gatcttggt                                                  19

<210> SEQ ID NO 5
<211> LENGTH: 19
<212> TYPE: DNA
<213> ORGANISM: Homo sapiens

<400> SEQUENCE: 5
gccacatctg tactgacaa                                                  19

<210> SEQ ID NO 6
<211> LENGTH: 19
<212> TYPE: DNA
<213> ORGANISM: Homo sapiens

<400> SEQUENCE: 6
agacaggcat tgcaaacac                                                  19

<210> SEQ ID NO 7
<211> LENGTH: 19
<212> TYPE: DNA
<213> ORGANISM: Homo sapiens

<400> SEQUENCE: 7
acatcactca ccgcttcac                                                  19

<210> SEQ ID NO 8
<211> LENGTH: 19
<212> TYPE: DNA
<213> ORGANISM: Homo sapiens

<400> SEQUENCE: 8
tcttaactac cgtgtggat                                                  19

<210> SEQ ID NO 9
<211> LENGTH: 19
<212> TYPE: DNA
<213> ORGANISM: Homo sapiens

<400> SEQUENCE: 9
aatacgccta caccaagca                                                  19

<210> SEQ ID NO 10
<211> LENGTH: 19
<212> TYPE: DNA
<213> ORGANISM: Homo sapiens

<400> SEQUENCE: 10
gtaccagcga catcatgac                                                  19

<210> SEQ ID NO 11
<211> LENGTH: 19
<212> TYPE: DNA
<213> ORGANISM: Homo sapiens

<400> SEQUENCE: 11
gcgacatcat gacgagtga                                                  19
```

```
<210> SEQ ID NO 12
<211> LENGTH: 19
<212> TYPE: DNA
<213> ORGANISM: Homo sapiens

<400> SEQUENCE: 12
aggacagatt gagtttctc                                                    19

<210> SEQ ID NO 13
<211> LENGTH: 19
<212> TYPE: DNA
<213> ORGANISM: Homo sapiens

<400> SEQUENCE: 13
ggtgctatgc cacattgaa                                                    19

<210> SEQ ID NO 14
<211> LENGTH: 19
<212> TYPE: DNA
<213> ORGANISM: Homo sapiens

<400> SEQUENCE: 14
gtttggtgag actcttcca                                                    19

<210> SEQ ID NO 15
<211> LENGTH: 19
<212> TYPE: DNA
<213> ORGANISM: Homo sapiens

<400> SEQUENCE: 15
agacggagcg tgatgaatc                                                    19

<210> SEQ ID NO 16
<211> LENGTH: 21
<212> TYPE: RNA
<213> ORGANISM: Homo sapiens

<400> SEQUENCE: 16
aaggaauugc guuacacuu a                                                  21

<210> SEQ ID NO 17
<211> LENGTH: 21
<212> TYPE: RNA
<213> ORGANISM: Homo sapiens

<400> SEQUENCE: 17
aaaauugcgu uuacacuuac a                                                 21

<210> SEQ ID NO 18
<211> LENGTH: 97
<212> TYPE: DNA
<213> ORGANISM: Homo sapiens

<400> SEQUENCE: 18
tgctgttgac agtgagcgag gcttccagaa gagcatctta tagtgaagcc acagatgtat       60
aagatgctct tctggaagcc ctgcctactg cctcgga                                97

<210> SEQ ID NO 19
<211> LENGTH: 97
<212> TYPE: DNA
<213> ORGANISM: Homo sapiens

<400> SEQUENCE: 19
```

```
tgctgttgac agtgagcgag cccatatcac ccaagaagtt tagtgaagcc acagatgtaa     60
acttcttggg tgatatgggc gtgcctactg cctcgga                              97

<210> SEQ ID NO 20
<211> LENGTH: 21
<212> TYPE: DNA
<213> ORGANISM: Homo sapiens

<400> SEQUENCE: 20
gcttccagaa gagcatctta t                                               21

<210> SEQ ID NO 21
<211> LENGTH: 22
<212> TYPE: DNA
<213> ORGANISM: Homo sapiens

<400> SEQUENCE: 21
gcccatatca cccaagaagt tt                                              22
```

SHIP-DEFICIENCY TO INCREASE MEGAKARYOCYTE PROGENITOR PRODUCTION

CROSS-REFERENCE TO RELATED APPLICATIONS

The present application is a divisional of U.S. application Ser. No. 11/451,004, filed Jun. 12, 2006, now U.S. Pat. No. 7,763,592, which is a continuation-in-part of U.S. application Ser. No. 10/904,667, filed Nov. 22, 2004, now U.S. Pat. No. 7,807,646, which claims the benefit of U.S. Provisional Application Ser. No. 60/481,677, filed Nov. 20, 2003, each of which is hereby incorporated by reference herein in its entirety, including any figures, tables, nucleic acid sequences, amino acid sequences, and drawings.

GOVERNMENT SUPPORT

This invention was made with government support under grant numbers HL072523 and CA087989 awarded by the Leukemia and Lymphoma Society of America and the National Institutes of Health. The government has certain rights in the invention.

BACKGROUND OF THE INVENTION

Platelets are critical for blood clotting. However, in various human anemias, and in bone marrow transplant patients, platelets and the megakaryocytes they are derived from can drop below a critical threshold that is required to maintain normal clotting. This can require platelet transfusions that are very expensive and which place the patient at risk for infection by blood-borne pathogens (e.g. HIV, HepB and C).

SH2-containing-5' inositol phosphatase-1 (SHIP) can catalyze the removal of the 5' phosphate group from $PI_{(3,4,5)}P3$ (PIP3) (Damen, J. E. et al. *Proc Natl Acad Sci USA*, 1996, 93:1689-1693). In this manner, SHIP regulates survival and proliferation of various hematopoietic cell types. The numbers of myeloid cells and osteoclasts are increased in SHIP-deficient mice due to enhanced activity of the phosphatidyl inositol 3-kinase (PI3K)/Akt signaling pathway that promotes their survival (Takeshita, S. et al. *Nat Med.*, 2002, 8:943-949; Helgason, C. D. et al. *Genes Dev.*, 1998, 12:1610-1620; Liu, Q. et al. *Genes Dev.*, 1999, 13:786-791).

Furthermore, the present inventors have shown that the number of natural killer cells are increased in SHIP-deficient mice resulting in an enhancement of engraftment of allogeneic hematopoietic stem cell grafts (Wang, J. W. et al. *Science*, 2002, 295:2094-2097). SHIP is also known to influence signaling pathways downstream of receptors for chemokines and cytokines involved in megakaryocytopoiesis and thrombopoiesis, such as Stromal-cell-derived-Factor 1 (SDF-1/CXCL-12) (Wang, J. F. et al. *Blood*, 1998, 92:756-764; Hamada, T. et al. *J Exp Med.*, 1998, 188:539-548; Hattori, K. et al. *Blood*, 2001, 97:3354-3360; Avecilla, S. T. et al., *Nat Med.*, 2004, 10:64-71; Chernock, R. D. et al. *Blood*, 2001, 97:608-615), interleukin-3 (Liu, L. et al. *Mol Cell Biol.*, 1994, 14:6926-6935), and thrombopoietin (TPO) (Lok, S. et al. *Nature*, 1994, 369:565-568; Drachman, J. G. et al. *Proc Natl Acad Sci USA*, 1997, 94:2350-2355). SHIP is phosphorylated after TPO binding to its receptor, c-mpl, leading to activation of PI3K that promotes cycling of megakaryocytes (MK) (Drachman, J. G. et al. *Proc Natl Acad Sci USA*, 1997, 94:2350-2355; Drachman, J. G. et al. *Blood*, 1997, 89:483-492; Geddis, A. E. et al. *J Biol Chem.*, 2001, 276:34473-34479). TPO influences MK development by controlling their proliferation, differentiation, survival and endoduplication (Kaushansky, K. et al. *Nature*, 1994, 369:568-571). Circulating platelets sequester free TPO, and thereby limit megakaryocytopoiesis during steady-state hematopoiesis (Kaushansky, K. *N Engl J Med.*, 1998, 339:746-754). Furthermore, SDF-1/CXCL12 induces transendothelial MK migration and platelet production in vitro (Wang, J. F. et al. *Blood*, 1998, 92:756-764; Hamada, T. et al. *J Exp Med.*, 1998, 188:539-548) and in vivo (Hattori, K. et al. *Blood*, 2001, 97:3354-3360). The present inventors have also shown that it enhances human thrombocytopoiesis in xenotransplanted NOD/SCID mice (Perez, L. E. et al. *Exp Hematol.*, 2004, 32:300-307). SHIP-deficient myeloid progenitors exhibit enhanced chemotaxis towards SDF-1/CXCL-12, indicating SHIP influences signaling downstream of CXCR-4 (Kim, C. H. et al. *J Clin Invest.*, 1999, 104:1751-1759). In addition, SHIP has been shown to regulate PIP3 levels after thrombin or collagen activation of platelets (Giuriato, S. et al. *J Biol Chem.*, 1997, 272:26857-26863; Giuriato, S. et al. *Biochem J.*, 2003, 376:199-207).

Thus, the present inventors hypothesized that SHIP may also be involved in the regulation of megakaryocytopoiesis and platelet production in vivo. It has been reported that colony forming-unit megakaryocyte (CFU-Mk) are decreased in $SHIP^{-/-}$ bone marrow (BM) (Moody, J. L. et al. *Blood*, 2004, 103:4503-10).

A naturally occurring gene-silencing mechanism triggered by double-stranded RNA (dsRNA), designated as small interfering RNA (siRNA), has emerged as a very important tool to suppress or knock down gene expression in many systems. RNA interference is triggered by dsRNA that is cleaved by an RNAse-III-like enzyme, Dicer, into 21-25 nucleotide fragments with characteristic 5' and 3' termini (Provost, P. D. et al. *Embo J*, 2002, 21:5864). These siRNAs act as guides for a multi-protein complex, including a PAZ/PIWI domain containing the protein Argonaute2, that cleaves the target mRNA (Hammond, S. M. et al. *Science*, 2001, 293:1146-1150). These gene-silencing mechanisms are highly specific and potent and can potentially induce inhibition of gene expression throughout an organism. The short interference RNA (siRNA) approach has proven effective in silencing a number of genes of different viruses (Fire, A. *Trends Genet.*, 1999, 15:358-363).

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., *Nature* 391:806-11 (1998); Sharp, *Genes Dev.* 13:139-41 (1999); Elbashir et al. *Nature* 411:494-98 (2001); Harborth et al., *J. Cell Sci.* 114:4557-65 (2001)). RNAi is mediated by double-stranded polynucleotides, such as double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polynucleotides in higher eukaryotes such as mammals (including humans) have also been considered (e.g., Tuschl, 2001 *Chembiochem.* 2:239-245; Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat.*

Struct. Biol. 8:746; Matzke et al., 2001 Science 293:1080; Scadden et al., 2001 EMBO Rep. 2:1107).

According to a current non-limiting model, the RNAi pathway is initiated by ATP-dependent cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., Curr. Opin. Gen. Dev. 12:225-32 (2002); Elbashir et al., 2001; Nyknen et al., Cell 107:309-21 (2001); Zamore et al., Cell 101:25-33 (2000)). In Drosophila, an enzyme known as "Dicer" cleaves the longer double-stranded RNA into siRNAs; Dicer belongs to the RNase III family of dsRNA-specific endonucleases (WO 01/68836; Bernstein et al., Nature 409:363-66 (2001)). Further, according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In C. elegans and Drosophila, RNAi may be mediated by long double-stranded RNA polynucleotides (WO 99/32619; WO 01/75164; Fire et al., 1998; Clemens et al., Proc. Natl. Acad. Sci. USA 97:6499-6503 (2000); Kisielow et al., Biochem. J. 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, Nature 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., Genes Dev. 15:188-200 (2001)); Harborth et al., J. Cell Sci. 114:4557-65 (2001); Carthew et al., Curr. Opin. Cell Biol. 13:244-48 (2001); Mailand et al., Nature Cell Biol. Advance Online Publication (Mar. 18, 2002); Mailand et al. 2002 Nature Cell Biol. 4:317).

siRNA may offer certain advantages over other polynucleotides known to the art for use in sequence-specific alteration or modulation of gene expression to yield altered levels of an encoded polypeptide product. These advantages include lower effective siRNA polynucleotide concentrations, enhanced siRNA stability, and shorter siRNA oligonucleotide lengths relative to such other polynucleotides (e.g., antisense, ribozyme or triplex polynucleotides). By way of a brief background, "antisense" polynucleotides bind in a sequence-specific manner to target nucleic acids, such as mRNA or DNA, to prevent transcription of DNA or translation of the mRNA (see, e.g., U.S. Pat. Nos. 5,168,053; 5,190,931; 5,135,917; 5,087,617; see also, e.g., Clusel et al., 1993 Nucl. Acids Res. 21:3405-11, describing "dumbbell" antisense oligonucleotides). "Ribozyme" polynucleotides can be targeted to an RNA transcript and are capable of catalytically cleaving such transcripts, thus impairing translation of mRNA (see, e.g., U.S. Pat. Nos. 5,272,262; 5,144,019; and 5,168,053, 5,180,818, 5,116,742 and 5,093,246; U.S. Ser. No. 2002/193579). "Triplex" DNA molecules refers to single DNA strands that bind duplex DNA to form a colinear triplex molecule, thereby preventing transcription (see, e.g., U.S. Pat. No. 5,176,996, describing methods for making synthetic oligonucleotides that bind to target sites on duplex DNA). Such triple-stranded structures are unstable and form only transiently under physiological conditions. Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polynucleotides at concentrations that are several orders of magnitude lower than those required for either antisense or ribozyme polynucleotides, and do not require the use of chemically modified nucleotides.

Due to its advantages, RNAi has been applied as a target validation tool in research and as a potential strategy for in vivo target validation and therapeutic product development (Novina, C. D. and Sharp, P. A., Nature, 2004, 430:161-164). In vivo gene silencing with RNAi has been reported using viral vector delivery and high-pressure, high-volume intravenous (i.v.) injection of synthetic iRNAs (Scherr, M. et al. Oligonucleotides, 2003, 13:353-363; Song, E. et al. Nature Med., 2003, 347-351). In vivo gene silencing has been reported after local direct administration (intravitreal, intranasal, and intrathecal) of siRNAs to sequestered anatomical sites in various models of disease or injury, demonstrating the potential for delivery to organs such as the eye, lungs, and central nervous system (Reich, S. J. et al. Mol. Vis., 2003, 9:210-216; Zhang, X. et al. J. Biol. Chem., 2004, 279:10677-10684; Dorn, G. et al. Nucleic Acids Res., 2004, 32, e49). Silencing of endogenous genes by systemic administration of siRNAs has also been demonstrated (Soutschek, J. et al. Nature, 2004, 432:173-178). It has been shown that siRNAs delivered systemically in a liposomal formulation can silence the disease target apolipoprotein B (ApoB) in non-human primates (Zimmermann T. S. et al., Nature, 2006, 441:111-114).

BRIEF SUMMARY OF THE INVENTION

The unexpected observations below provide the basis for this invention, which is directed to a method of increasing the yield of megakaryocytes and megakaryocyte progenitors through the inhibition of SHIP gene function.

As indicated above, SHIP influences signals downstream of cytokine and chemokine receptors that play a role in megakaryocytopoiesis, including the receptors for thrombopoietin and Stromal-cell-derived-Factor 1/CXCL-12. Herein, the present inventors show that two separate strains of mice with different SHIP mutations exhibit profound increases in megakaryocyte progenitors (MKP; Lin$^-$cKit$^+$CD41$^+$) and megakaryocytes (MK; Lin$^-$cKit$^-$CD41$^+$) in the hematopoietic compartment. However, despite increased MKP and MK numbers, platelet production is significantly lower in SHIP-deficient mice. These findings demonstrate that SHIP is a key regulator of signaling pathways that control megakaryocytopoiesis in vivo.

Mice that lack expression of a SHIP gene exhibit increased levels of both megakaryocyte progenitors and megakaryocytes in the bone marrow and spleen. In fact, megakaryocytes, the immediate precursor of platelets, are increased in the periphery of SHIP-deficient mice approximately 10 - to 100-fold. Therefore, methods that inhibit SHIP expression, its enzymatic activity, or its signaling functions could be used in human patients in vivo to temporarily increase megakaryocytes during periods when their platelets drop below numbers sufficient to promote normal blood clotting. In a similar way, SHIP expression or activity could be used to increase the yield of megakaryocytes and megakaryocyte progenitors in ex vivo expansion regimens that use human growth factors.

One embodiment of the invention is a method for increasing the yield of megakaryocytes or megakaryocyte progenitors in a patient, in vivo, comprising the steps of administering a therapeutically effective amount of a substance that inhibits SHIP function (a SHIP inhibitor) to the patient. The SHIP inhibiting substance can be, for example, one or more of the following: interfering RNA, antisense oligonucleotides, ribozymes, DNAzymes, nucleic acid modifiers, PNAs, non-standard nucleic acids, aptamers, decoys, oligonucleotide based gene regulation, or dominant/negative mutants.

Another embodiment relates to a method for increasing the yield of megakaryocytes or megakaryocyte progenitors in a sample in vitro (e.g., a sample obtained from a patient ex vivo), comprising providing a sample containing target cells and contacting the target cells in vitro with an efficacious amount of a substance that inhibits SHIP function. The SHIP inhibiting substance can be, for example, one or more of the following: interfering RNA, antisense oligonucleotides, ribozymes, DNAzymes, nucleic acid modifiers, PNAs, non-standard nucleic acids, aptamers, decoys, oligonucleotide-based gene regulation, and dominant/negative mutants. Target cells include megakaryocytes and/or megakaryocyte progenitors. The sample can be any composition containing megakaryocytes and/or megakaryocyte progenitors. For example, the sample can be a biological sample obtained from a patient (such as peripheral blood, bone marrow, spleen, or other tissue or fluid containing megakaryocytes and/or megakaryocyte progenitors), or a cell culture. Thus, the step of providing a sample containing target cells can comprise harvesting a sample from a patient.

Another embodiment of the invention relates to a method for improving haematopoietic recovery in a patient in need thereof, comprising administering a therapeutically effective amount of a substance that inhibits SHIP function to the patient. The SHIP inhibiting substance can be, for example, one or more of the following: interfering RNA, antisense oligonucleotides, ribozymes, DNAzymes, nucleic acid modifiers, PNAs, non-standard nucleic acids, aptamers, decoys, oligonucleotide-based gene regulation, and dominant/negative mutants. Target cells include megakaryocytes and/or megakaryocyte progenitors.

Another embodiment of the invention relates to a method for improving haematopoietic recovery in a patient in need thereof, ex vivo, comprising harvesting target cells from a patient, contacting the target cells with an efficacious amount of a substance that inhibits SHIP function, and delivering (e.g., re-infusing) the expanded target cells back into the patient. The target cells are chosen from among megakaryocytes and/or megakaryocyte progenitors.

BRIEF DESCRIPTION OF THE DRAWINGS

FIG. 1A shows results of flow cytometric analysis of bone marrow (BM), peripheral blood (PB) and spleen of SHIP$^{-/-}$ (−/−) and SHIP$^{\Delta IP/\Delta IP}$ (ΔIP/ΔIP) and their respective WT littermates. Shown is a representative flow cytometry plot of c-Kit vs. CD41 after gating on live cells and Lin-cells. MKP are in the upper right quadrant and MK in the lower right quadrant. Percentages for each population are indicated on the plot. FIGS. 1B-1, 1B-2, and 1B-3 show absolute numbers of MKP (Lin$^-$cKit$^+$CD41$^+$) in BM (sum for 2 femurs+2 tibias), intact spleen, and PB. FIGS. 1C-1, 1C-2, and 1C-3 show absolute numbers of MK (Lin$^-$cKit$^-$CD41$^+$) in BM (sum for 2 femurs+2 tibias), intact spleen, and PB. The bar graphs show the different SHIP-deficient models in black and their respective WT littermates in gray. (n=3 mice/genotype). Statistical significance was assessed using the two-tailed Student t-test, **p=0.0001, *p<0.0005, ++p<0.005, +p<0.05. FIGS. 1D and 1E show hematoxylin-eosin (H & E) staining of SHIP$^{\Delta IP/\Delta IP}$ and WT spleen section, and SHIP$^{-/-}$ and WT BM section, respectively. The images were photographed at 40× (spleen) and 63×(BM) magnification.

FIG. 2 shows the human SHIP cDNA sequence (GenBank accession no. NM_005541).

FIGS. 3A and 3B show mouse SHIP amino acid and cDNA sequences (GenBank accession no. NM_10566).

FIG. 4 shows the human SHIP cDNA sequence with the targets for siRNA sequence H1 (SEQ ID NO:16), siRNA sequence H2 (SEQ ID NO:17), shRNA 63332 (SEQ ID NO:18), and shRNA 63331 (SEQ ID NO:19) in boxes.

FIGS. 5A, 5B-1, 5B-2, and 5B-3 demonstrate a significant increase in the percentage of MKP cells in SHIP-ablated BM and spleen. MxCre$^+$ and MxCre$^-$ mice with foxed SHIP alleles were treated with polyIC 3 times prior to being analyzed. FIG. 5A shows representative FACS plots showing detection of and MK and MKP in the BM and spleen of MxCre$^+$ and MxCre$^-$ mice after treatment. FIG. 5B-1 shows the percentage of MKP in BM (top), spleen (Spl) (bottom) and of SHIP-ablated (black) and WT (grey) mice. FIG. 5B-2 shows the absolute number of MKP cells in BM (per femur and tibia pair). FIG. 5B-3 shows the percentage of MK found in the spleen. Data was acquired on a FACS Calibur with CellQuest software (BD Biosciences, San Jose, Calif.), and analyzed with FlowJo. Significance was established using the unpaired student t test (Prism 4). +++p<0.0005, ++p<0.005, and +p<0.05. (mean±SEM, n=3).

As shown in FIG. 7, H1 was more effective at silencing SHIP.

BRIEF DESCRIPTION OF THE SEQUENCES

Figure 1A:
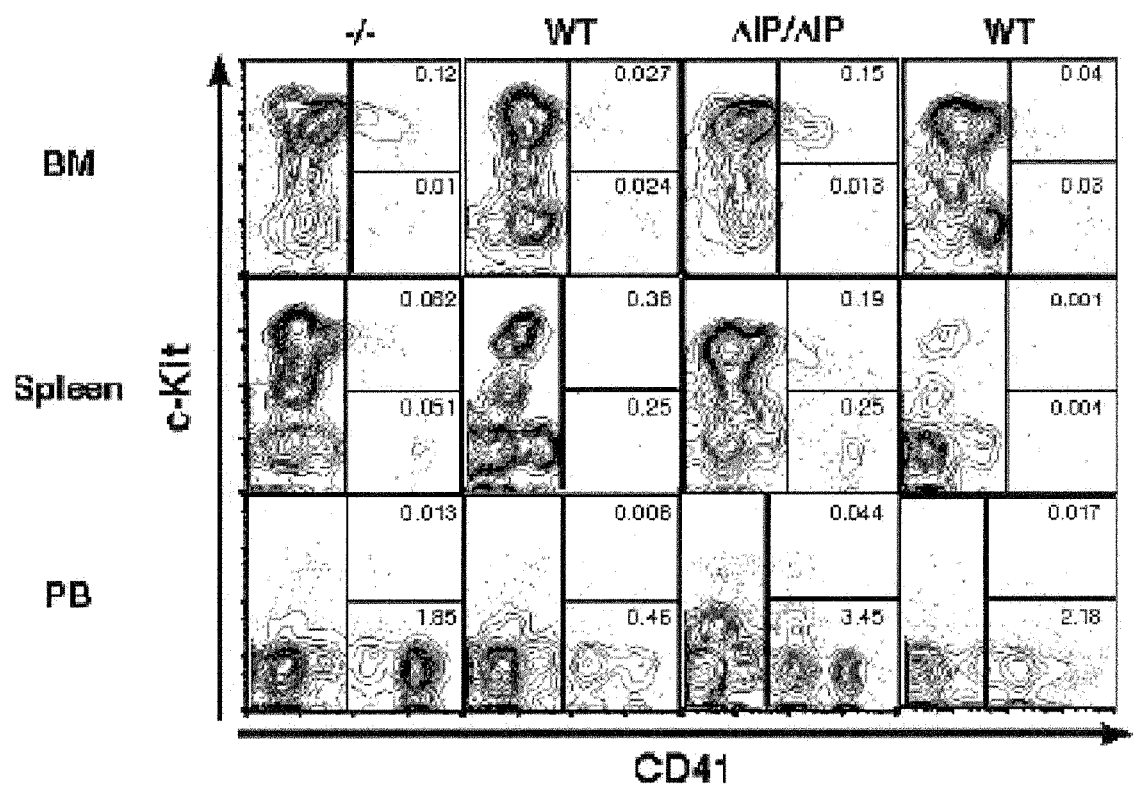
FIGS. 1A, 1B-1, 1B-2, 1B-3, 1C-1, 1C-2, 1C-3, 1D, and 1E show increased numbers of MKP and MK in SHIP-deficient mice.
Figures 1, 1B:
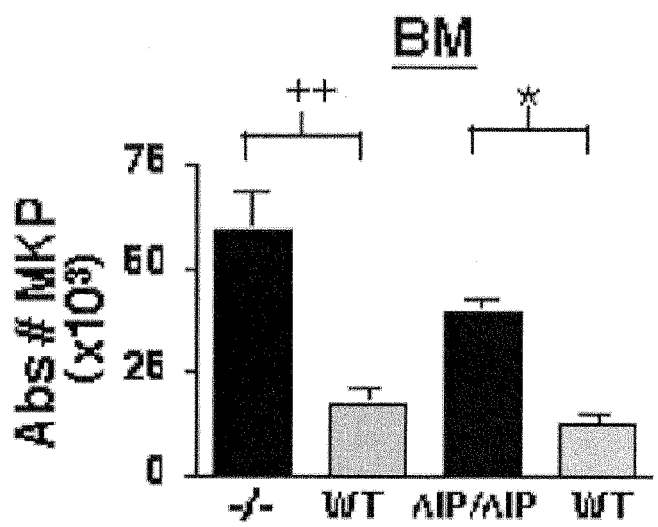
Figures 1, 1B, 2:
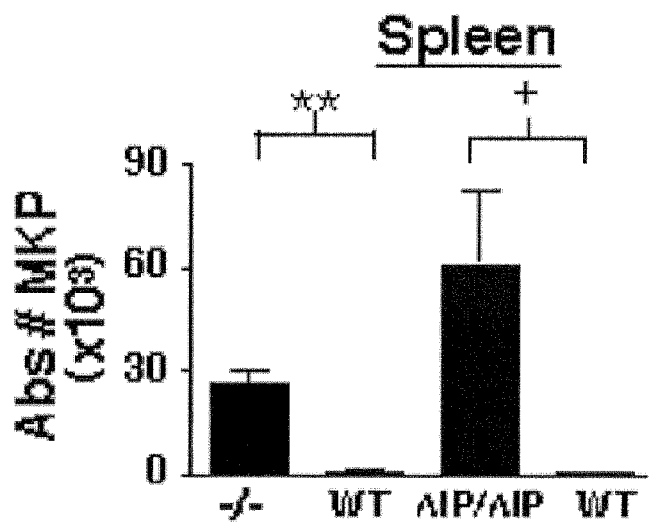

SEQ ID NO:1 is the human SHIP cDNA sequence (GenBank accession nos. NM_005541 and NM_001017915) (FIG. 2).

Figures 1, 1B, 2, 3:
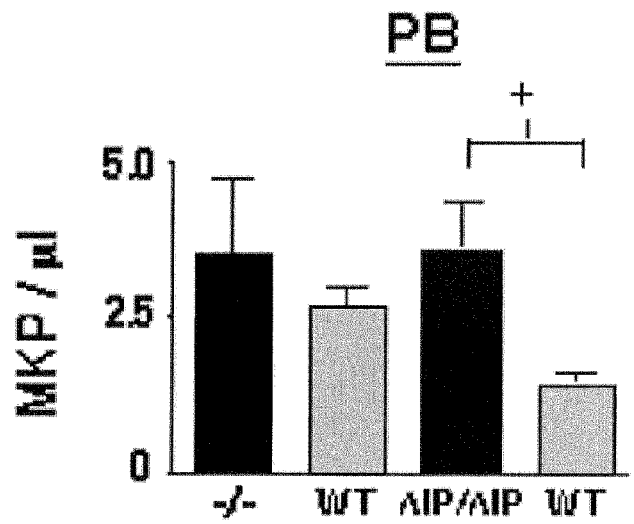

SEQ ID NO:2 is the mouse SHIP cDNA sequence (GenBank accession no. NM_10566) (FIG. 3).

SEQ ID NOs:3-15 are examples of target regions within the human SHIP open reading frame.

SEQ ID NOs:16-17 are siRNA sequences (designated H1 and H2, respectively) that have been identified as effective at SHIP knockdown in human NK cell lines.

SEQ ID NOs:18-19 are shRNA sequences (designated 63332 and 63331, respectively) targeting human SHIP, including the loop and termini portions of the shRNA.

SEQ ID NOs:20-21 are the target sequences within human SHIP for shRNA 6332 (SEQ ID NO:18) and shRNA 63331 (SEQ ID NO:19), respectively.

DETAILED DESCRIPTION OF THE INVENTION

As described in detail in the Examples, BM of SHIP-deficient mice exhibit increased numbers of megakaryocyte progenitors (MKP) (Lin$^-$,c-Kit$^+$,CD41$^+$), but decreased numbers of MK (Lin$^-$,c-Kit$^-$,CD41$^+$). In addition, the present inventors observed expanded numbers of both MKP and MK in SHIP-deficient spleens. Peripheral blood (PB) of SHIP-deficient mice also contains increased numbers of MK relative to WT controls. However, platelet levels in the PB of SHIP-deficient mice were not significantly altered relative to WT controls.

The invention is based on a method of modulating megakaryocytes and their progenitors, as a significant leap forward in the treatment of various human anemias. The present inventors reasoned that the identification of a novel gene involved in megakaryocyte production would lead to increased efficacy of current treatments. The clinical potential of such an approach is significant, as it allows for modulation of a gene-specific determinate of megakaryocyte production.

One embodiment of the invention is a method of increasing the yield of megakaryocytes in a patient, in vivo, comprising the steps of administering a therapeutically effective amount of a substance that inhibits SHIP function to the patient. The SHIP inhibiting substance can be, for example, one or more of the following: interfering RNA, antisense oligonucleotides, ribozymes, DNAzymes, nucleic acid modifiers, PNAs, non-standard nucleic acids, aptamers, decoys, oligonucleotide based gene regulation, or dominant/negative mutants.

Another embodiment relates to a method of increasing the yield of megakaryocytes in a sample in vitro (e.g., a sample obtained from a patient ex vivo), comprising providing a sample containing target cells and contacting the target cells in vitro with an efficacious amount of a substance that inhibits SHIP function. The SHIP inhibiting substance can be, for example, one or more of the following: interfering RNA, antisense oligonucleotides, ribozymes, DNAzymes, nucleic acid modifiers, PNAs, non-standard nucleic acids, aptamers, decoys, oligonucleotide-based gene regulation, and dominant/negative mutants. Target cells include megakaryocytes and/or megakaryocyte progenitors. The sample can be any composition containing megakaryocytes and/or megakaryocyte progenitors. For example, the sample can be a biological sample obtained from a patient (such as peripheral blood, bone marrow, spleen, or other tissue or fluid containing megakaryocytes and/or megakaryocyte progenitors), or a cell culture. Thus, the step of providing a sample containing target cells can comprise harvesting a sample from a patient. Optionally, the method of the invention further comprises detecting the presence of megakaryocytes or their progenitors in the sample before, during, and/or after administration of the SHIP inhibitor. Optionally, the method of the invention further comprises isolating the megakaryocytes or their progenitors from the sample. Isolation of the cells may carried out before, during, and/or after detection of the megakaryocytes or megakaryocyte progenitors within the sample.

Methods for detecting megakaryocytes and their progenitors are known in the art (see, for example, Nakorn T. N. et al., *Proc. Natl, Acad. Sci. USA,* 2003, 100:205-210; Bruno E. and R. Hoffman., *Semin. Hematol.,* 1998, 35(3):183-191; Ivanyi J. L. et al., *Act Histochem.,* 1993, 95(1):79-88; Vannucchi A. S. et al., *Blood,* 2000, 95:2559-2568; Boque C. et al., *J. Clinical Pathology,* 1989, 42:982-984; Long M. W. and C. H. Heffner, *Exp. Hematol.,* 1998, 16(1):62-70; Bruno E. et al., *Exp. Hematol.,* 1996, 24(4):552-558; Long M. W. et al., *J. Clin. Invest.,* 1998, 82(5):1779-1786; U.S. patent publication US 2005/0003471 A1, Wang et al., each of which are incorporated herein by reference in their entirety). For example, megakaryocytes may be detected based on cell surface markers (such as CD9, CD41, CD61, actin, FVIIIRAg) and optionally separated using flow cytometry.

Another embodiment of the invention relates to a method for improving haematopoietic recovery in a patient in need thereof, comprising administering a therapeutically effective amount of a substance that inhibits SHIP function to the patient. The SHIP inhibiting substance can be, for example, one or more of the following: interfering RNA, antisense oligonucleotides, ribozymes, DNAzymes, nucleic acid modifiers, PNAs, non-standard nucleic acids, aptamers, decoys, oligonucleotide-based gene regulation, and dominant/negative mutants. Target cells include megakaryocytes and/or megakaryocyte progenitors.

Another embodiment of the invention relates to a method for improving haematopoietic recovery in a patient in need thereof, ex vivo, comprising harvesting target cells from a patient, contacting the target cells with an efficacious amount of a substance that inhibits SHIP function, and delivering (e.g., re-infusing) the expanded target cells back into the patient. The target cells include megakaryocytes and/or megakaryocyte progenitors. Optionally, the method of the invention further comprises isolating the megakaryocytes or their progenitors from the sample before, during, and/or after administration of the SHIP inhibitor. Isolation of the cells may carried out before, during and/or after detection of the megakaryocytes or megakaryocyte progenitors within the sample.

As used herein, the term "SHIP" refers to hematopoietic-specific SH2-containing inositol-5-phosphatase-1, which catalyzes the removal of the 5' phosphate group from $PI_{(3,4,5)}P3$ (PIP3) and inositol 1,3,4,5-tetrakisphosphate (IP4). SHIP, which is also known in the scientific literature as SHIP-1, SHIP1, SHIPI, and SHIP-I was also the subject of Helgason, et al., *Genes Dev.,* 1998, 12(11):1610-1620; Huber et al., *Proc. Natl. Aca. Sci. USA,* 1998, 95(19):11330-11335; Liu et al., *Genes Dev.,* 1999, 13(7):789-791; Liu et al.; *J. Exp. Med.,* 1998, 188(7):1333-1342; Rohrschneider et al., *Genes & Development,* 2000, 14:505-520, U.S. Pat. No. 6,090,621 (Kavanaugh et al.), PCT publication WO 9710252A1 (Rohrschneider, L. R.), and PCT publication WO 9712039A2 (Krystal, G.). The nucleotide sequences of mouse SHIP and human SHIP, for example, have been publicly available for several years (GenBank Accession Numbers NM__10566 and NM__005541, respectively, on the National Center for Biotechnology Information (NCBI) database).

The terms "inhibitor of SHIP", "SHIP inhibitor", and "SHIP inhibiting substance" are used herein interchangeably to refer to any molecule that decreases the activity of SHIP (inositol phosphatase activity) or decreases the protein level of SHIP. Thus, a SHIP inhibitor can be a small molecule that decreases activity of SHIP, e.g., by interfering with interaction of the inositol phosphatase with another molecule, e.g., its substrate. The SHIP inhibitor can also be a small molecule that decreases expression of the gene encoding the inositol phosphatase. An inhibitor can also be an interfering RNA molecule, antisense oligonucleotide, a ribozyme, an antibody, or a dominant negative mutant of SHIP. Dominant negative mutants of SHIP have been developed (Gupta N. et al., *J. Exp. Med.,* 1997, 186(3):473-478; and Tridandapani S. et al., *J. Immunol.,* 2002, 169(8):4370-4378, which are each incorporated herein by reference in their entirety). A "direct inhibitor" of SHIP is an inhibitor that interacts with the SHIP enzyme, or substrate thereof, or with a nucleic acid encoding SHIP (e.g., the SHIP gene or its mRNA) or its regulatory sequences. An "indirect inhibitor" of SHIP is an inhibitor that interacts upstream or downstream of the SHIP enzyme in the regulatory pathway, and which does not interact with the enzyme or substrate thereof or with a nucleic acid encoding SHIP or its regulatory sequences.

The methods of the invention can further include a step of determining the amount or concentration of megakaryocytes or megakaryocyte progenitors in vitro (e.g., in a sample) or in vivo (e.g., in a mammal) before introduction of the SHIP inhibitor, after introduction of the SHIP inhibitor, or both. The terms "detecting", "detection", "analyzing", "analysis", and other grammatical variations thereof (e.g., "detecting megakaryocytes," etc.) refer to any quantitative, semi-quantitative, or qualitative method for determining an analyte in general, and a megakaryocyte or megakaryocyte progenitor in particular. For example, a method that merely detects the presence or absence of a megakaryocyte or its progenitor in a samples lies within the scope of the term, as do methods that provide data as to the amount or concentration of the cells in the sample.

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression.

The terms "operably-linked" or "operatively-linked" are used herein interchangeably to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a siRNA will typically have its own operably-linked promoter sequence.

The term "vector" is used to refer to any molecule (e.g., nucleic acid, plasmid, or virus) used to transfer coding information (e.g., a polynucleotide of the invention) to a host cell. The terms "expression vector" and "transcription vector" are used interchangeably to refer to a vector that is suitable for use in a host cell (e.g., a subject's cell) and contains nucleic acid sequences that direct and/or control the expression of exogenous nucleic acid sequences. Expression includes, but is not limited to, processes such as transcription, translation, and RNA splicing, if introns are present.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as SHIP.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., SHIP mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

As used herein, the tens "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

The term "dominant negative mutant" is art-recognized and refers to the mutant form of a wild-type protein that interferes with the function of the wild-type protein (e.g., by interacting with the wild-type protein). Thus, overexpression of the dominant negative mutant can be expected to interfere with the function of the wild-type version of the protein.

As used herein, the term "mismatch" refers to a basepair consisting of noncomplementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines, in an organism.

A gene "involved in" or "associated with" a disorder includes a gene, the normal or aberrant expression or function of which affects or causes a disease or disorder or at least one symptom of the disease or disorder. The methods of the invention are useful in decreasing expression of SHIP in megakaryocytes and their progenitors in vitro or in vivo, consequently increasing their proliferation. Thus, the methods of the invention are useful in the treatment of human or non-human animal subjects suffering from, or at risk of developing, disorders associated with impaired megakaryocyte production.

The methods of the invention may include further steps. In some embodiments, a subject with the relevant condition or disease (e.g., disorders associated with impaired megakaryocyte production) is identified or a patient at risk for the condition or disease is identified prior to administration of the SHIP inhibitor. A patient may be someone who has not been diagnosed with the disease or condition (diagnosis, prognosis, and/or staging) or someone diagnosed with the disease or condition (diagnosis, prognosis, monitoring, and/or staging), including someone treated for the disease or condition (prognosis, staging, and/or monitoring). Alternatively, the person may not have been diagnosed with the disease or condition but suspected of having the disease or condition based either on patient history or family history, or the exhibition or observation of characteristic symptoms.

As used herein, an "effective amount" of a SHIP inhibitor (such as an interfering RNA, an antisense oligonucleotide, or a ribozyme, which selectively interferes with expression of SHIP) is that amount effective to bring about the physiological changes desired in the cells to which the SHIP inhibitor is administered in vitro (e.g., ex vivo) or in vivo. The term "therapeutically effective amount" as used herein, means that amount of SHIP inhibitor alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated. Preferably, suppression of SHIP function (e.g., by reduction of SHIP expression) results in increased megakaryocytopoiesis.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Reduction (suppression) of expression results in a decrease of SHIP mRNA and/or protein. For example, in a given cell, the suppression of SHIP mRNA by administration of a SHIP inhibitor that reduces SHIP function by reducing SHIP expression (such as interfering RNA, antisense oligonucleotide, or ribozyme) results in a decrease in the quantity of SHIP mRNA relative to an untreated cell. Suppression may be partial. Preferred degrees of suppression are at least 50%, more preferably one of at least 60%, 70%, 80%, 85%, or 90%. A level of suppression between 90% and 100% is generally considered a "silencing" of expression. Where an increase in megakaryocytopoiesis is desired, the level of suppression is sufficient to increase megakaryocyte or megakaryocyte progenitor production.

SHIP gene expression can be determined before and/or after introduction of the SHIP inhibitor in vitro or in vivo. Reduction in SHIP gene expression can be detected at either the protein or mRNA level. Protein expression analysis can be performed by Western blotting, immunofluorescence, or flow cytometry and cell sorting (FACS). Reduction in SHIP gene expression can be detected at the mRNA level by real-time RT-PCR, microarray analysis, or Northern blotting, for example. Preferably, all expression data is compared with levels of a "house keeping" gene to normalize for variable amounts of RNA in different samples.

RNA Interference

RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, *Curr. Opin. Genet. Dev.:* 12, 225-232 (2002); Sharp, *Genes Dev.,* 15:485-490 (2001)). In mammalian cells, RNAi can be triggered by 21-nucleotide (nt) duplexes of small interfering RNA (siRNA) (Chiu et al., *Mol. Cell.* 10:549-561 (2002); Elbashir et al., *Nature* 411:494-498 (2001)), or by micro-RNAs (miRNA), functional small-hairpin RNA (shRNA), or other dsRNAs which can be expressed in vivo using DNA templates with RNA polymerase III promoters (Zeng et al., *Mol. Cell* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci. USA* 99(9):6047-6052 (2002); McManus et al., *RNA* 8:842-850 (2002); Sui et al., *Proc. Natl. Acad. Sci. USA* 99(6):5515-5520 (2002)), each of which are incorporated herein by reference in their entirety.

The scientific literature contains many reports of endogenous and exogenous gene expression silencing using siRNA, highlighting their therapeutic potential (Gupta, S. et al. *PNAS,* 2004, 101:1927-1932; Takaku, H. *Antivir Chem.*

Chemother., 2004, 15:57-65; Pardridge, W. M. *Expert Opin. Biol. Ther.*, 2004, 4:1103-1113; Zheng, B. J. *Antivir. Ther.*, 2004, 9:365-374; Shen, W. G. *Chin. Med. J. (Engl)*, 2004, 117:1084-1091; Fuchs, U. et al. *Curr. Mol. Med.*, 2004, 4:507-517; Wadhwa, R. et al. *Mutat. Res.*, 2004, 567:71-84; Ichim, T. E. et al. *Am. J. Transplant*, 2004, 4:1227-1236; Jana, S. et al. *Appl. Microbiol. Biotechnol.*, 2004, 65:649-657; Ryther, R. C. et al. *Gene Ther.*, 2005, 12:5-11; Chae, S-S. et al., *J. Clin. Invest.*, 2004, 114:1082-1089; Fougerolles, A. et al., *Methods Enzymol.*, 2005, 392:278-296), each of which is incorporated herein by reference in its entirety. Therapeutic silencing of endogenous genes by systemic administration of siRNAs has been described in the literature (Kim B. et al., *American Journal of Pathology*, 2004, 165:2177-2185; Soutschek J. et al., *Nature*, 2004, 432:173-178; Pardridge W. M., *Expert Opin. Biol. Ther.*, 2004, July, 4(7):1103-1113), each of which is incorporated herein by reference in its entirety.

Accordingly, the invention includes such interfering RNA molecules that are targeted to SHIP mRNA. The interfering RNA molecules are capable, when suitably introduced into or expressed within a cell that otherwise expresses SHIP mRNA, of suppressing expression of the SHIP gene by RNAi. The interfering RNA may be a double-stranded siRNA. As the skilled person will appreciate, and as explained further herein, an siRNA molecule may include a short 3' DNA sequence also. Alternatively, the nucleic acid may be a DNA (usually double-stranded DNA) which, when transcribed in a cell, yields an RNA having two complementary portions joined via a spacer, such that the RNA takes the form of a hairpin when the complementary portions hybridize with each other. In a mammalian cell, the hairpin structure may be cleaved from the molecule by the enzyme Dicer, to yield two distinct, but hybridized, RNA molecules.

In one embodiment, the invention provides an interfering RNA that is capable, when suitably introduced or expressed within a cell that normally expresses SHIP mRNA, suppresses its expression by RNAi, wherein the interfering RNA is generally targeted to the SHIP enzymatic domain (inositol 5'-phosphatase domain), within the human SHIP cDNA (SEQ ID NO:1). Examples of SHIP target sequences include GCCTGTTGTCATCCATTGA (SEQ ID NO:3), ATAAGTTGGTGATCTTGGT (SEQ ID NO:4), GCCACATCTGTACTGACAA (SEQ ID NO:5), AGACAGGCATTGCAAACAC (SEQ ID NO:6), ACATCACTCACCGCTTCAC (SEQ ID NO:7), TCTTAACTACCGTGTGGAT (SEQ ID NO:8), AATACGCCTACACCAAGCA (SEQ ID NO:9), GTACCAGCGACATCATGAC (SEQ ID NO:10), GCGACATCATGACGAGTGA (SEQ ID NO:11), AGGACAGATTGAGTTTCTC (SEQ ID NO:12), GGTGCTATGCCACATTGAA (SEQ ID NO:13), GTTTGGTGAGACTCTTCCA (SEQ ID NO:14), AGACGGAGCGTGATGAATC (SEQ ID NO:15), GCTTCCAGAAGAGCATCTTAT (SEQ ID NO:20), and GCCCATATCACCCAAGAAGTTT (SEQ ID NO:21). In a specific embodiment, the interfering RNA comprises a sequence selected from the group consisting of SEQ ID NO:16, SEQ ID NO:17, SEQ ID NO:18, and SEQ ID NO:19. Preferably, the interfering RNA sequence is within the range of about 19 to 23 nucleotides. For example, in those embodiments in which an shRNA is utilized, that portion of the shRNA targeting SHIP is preferably within the range of about 19 to 23 nucleotides.

It is expected that perfect identity/complementarity between the interfering RNA used in the method of the invention and the target sequence, although preferred, is not essential. Accordingly, the interfering RNA may include a single mismatch compared to the target sequence within the SHIP mRNA. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

siRNA Molecules

Short interfering RNAs (siRNAs) induce the sequence-specific suppression or silencing (i.e., reducing expression which may be to the extent of partial or complete inhibition) genes by the process of RNAi. Thus, siRNA is the intermediate effector molecule of the RNAi process. The interfering RNA that function as SHIP inhibitors include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the SHIP mRNA, and the other strand is identical or substantially identical to the first strand. The dsRNA molecules that function as SHIP inhibitors can be chemically synthesized, or can be transcribed in vitro from a DNA template, or in vivo from, e.g., shRNA. The dsRNA molecules can be designed using any method known in the art, for instance, by using the following protocol:

1. Using any method known in the art, compare the potential targets to the appropriate genome database (human, mouse, rat, etc.) and eliminate from consideration any target sequences with significant homology to other coding sequences. One such method for sequence homology searches is known as BLAST, which is available at the National Center for Biotechnology Information (NCBI) web site of the National Institutes of Health. Also available on the NCBI webs site is the HomoloGene database, which is a publicly available system for automated detection of homologs among the annotated genes of several completely sequenced eukaryotic genomes and is readily utilized by those of ordinary skill in the art.

2. Select one or more sequences that meet your criteria for evaluation. Further general information regarding the design and use of siRNA can be found in "The siRNA User Guide," available at the web site of the laboratory of Dr. Thomas Tuschl at Rockefeller University (Elbashir et al., *EMBO J.*, 2001, 20:6877-6888).

3. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Initially, basic criteria were defined for identification of efficient siRNA, such as GC content and position of the targeted sequence in the context of the mRNA (Elbashir S M. et al., *Methods*, 2002, 26:199-213). Further progress was achieved more recently, when the assembly of the RNAi enzyme complex was described as being dependent on thermodynamic characteristics of the siRNA (Khrvorova A. et al., *Cell*, 2003, 115:209-216; Schwarz D. S. et al., *Cell*, 2003, 115:199-208). The relative stability of both ends of the duplex was determined to have effects on the extent to which the individual strands enter the RNAi pathway. In addition, certain sequence motifs at defined positions of the siRNA were reported to influence its potency (Amarzguioui M. and H. Prydz, *Biochem. Biophys. Res. Commun.,* 2004, 316:1050-1058; Reynolds A. et al., *Nature Biotechnol.,* 2004, 22:326-330). On this basis, sophisticated algorithms have been developed to increase the success rate of siRNA design and are available to those skilled in the art (Amarzguioui M. and H. Prydz, 2004; Reynolds A. et al., 2004; and Ui-Tei K. et al., *Nucl. Acids Res.,* 2004, 32:936-948, each of which is incorporated herein in its entirety).

Other computational tools that may be used to select siRNAs of the present invention include the Whitehead siRNA selection Web Server from the bioinformatics group at the Whitehead Institute for Biomedical Research in Cambridge, Mass., and other disclosed in Yuan, B. et al. ("siRNA Selection Server: an automated siRNA oligonucleotide prediction server", *Nucleic Acids Research,* 2004, Vol. 32, W130-W134, Web Server issue) and Bonetta L. ("RNAi: Silencing never sounded better", *Nature Methods,* October, 2004, 1(1):79-86), each of which are incorporated by reference herein in their entirety.

The efficiencies of different siRNAs may differ significantly. However, strategies for rational design of effective interfering RNA exist (Gong D. and J. E. Ferrell Jr., TRENDS in Biotechnology, 2004, 22(9):451; Schubert S. et al., J. Mol. Biol., 2005, 348:883-893; Pancoska P. et al., Nucleic Acids Research, 2004, 32(4):1469-1479; Mittal V., *Nat. Rev. Genet.,* 2004, 5(5):355-365, each of which is incorporated herein by reference in its entirety).

Screening for the most efficient siRNAs using cell cultures may be carried out. Several in vitro screening methods based on the use of siRNA mixtures, which may contain a particular efficient siRNA (or several), have been developed. These include the preparation of siRNA mixtures using RNase III or Dicer enzymes to digest longer double-stranded RNAs, such as BLOCK-IT products (INVITROGEN, Carlsbad Calif.) (Yang D. et al., *Proc. Natl. Acad. Sci. USA,* 2002, 99:9942-9947; Myers J. W. et al., *Nat. Biotechnol.,* 2003, 21:324-328). The short RNAs produced as a result of these digestions have been found to be efficient in RNAi. Oligonucleotide arrays can also be used for the efficient preparation of defined mixtures of siRNAs for reducing the expression of exogenous and endogenous genes such as SHIP (Oleinikov A. V. et al., *Nucleic Acids Research,* 2005, 33(10):e92).

The SHIP inhibitors of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The SHIP inhibitors of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53(1-3):137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

The SHIP inhibitors of the present invention can also be labeled using any method known in the art; for instance, nucleic acids can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^3$H, $^{32}$P, or other appropriate isotope.

Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

There are a number of companies that will generate interfering RNAs for a specific gene. Thermo Electron Corporation (Waltham, Mass.) has launched a custom synthesis service for synthetic short interfering RNA (siRNA). Each strand is composed of 18-20 RNA bases and two DNA bases overhang on the 3' terminus. Dharmacon, Inc. (Lafayette, Colo.) provides siRNA duplexes using the 2'-ACE RNA synthesis technology. Qiagen (Valencia, Calif.) uses TOM-chemistry to offer siRNA with high individual coupling yields (Li, B. et al., *Nat. Med.,* 2005, 11(9), 944-951).

siRNA Delivery for Longer-Term Expression

Synthetic siRNAs can be delivered into cells by methods known in the art, including cationic liposome transfection (LIPOFECTAMINE 2000 reagent, for example) and electroporation, for example. However, these exogenous siRNA generally show short term persistence of the silencing effect (4 to 5 days in cultured cells), which may be beneficial in certain embodiments. To obtain longer suppression of SHIP expression and to facilitate delivery under certain circumstances, one or more siRNA duplexes, e.g., SHIP ds siRNA, can be expressed within cells from recombinant DNA constructs (McIntyre G. J. and G. C. Fanning, *BMC Biotechnology,* 2006, 6:1-8). Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence(s)

under the control of a T7 promoter also make functional siRNAs when co-transfected into the cells with a vector expressing T7 RNA polymerase (Jacque (2002), supra). A single construct may contain multiple sequences coding for siRNAs, such as multiple regions of SHIP mRNA, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase 111-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci.* USA 99(22):14236-40 (2002)). In adult mice, efficient delivery of siRNA can be accomplished by the "high-pressure" delivery technique, a rapid injection (within 5 seconds) of a large volume of siRNA containing solution into animal via the tail vein (Liu (1999), supra; McCaffrey (2002), supra; Lewis, *Nature Genetics* 32:107-108 (2002)). Nanoparticles, liposomes and other cationic lipid molecules can also be used to deliver siRNA into animals. It has been shown that siRNAs delivered systemically in a liposomal formulation can silence the disease target apolipoprotein B (ApoB) in non-human primates (Zimmermann T. S. et al., *Nature,* 2006, 441: 111-114). A gel-based agarose/liposome/siRNA formulation is also available (Jiamg M. et al., *Oligonucleotides,* 2004, Winter, 14(4):239-48).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the SHIP mRNA to be targeted by the siRNA generated from the engineered RNA precursor will be depleted from the cell or organism, leading to a decrease in the concentration of any translational product encoded by that mRNA in the cell or organism. The RNA precursors are typically nucleic acid molecules that individually encode either one strand of a dsRNA or encode the entire nucleotide sequence of an RNA hairpin loop structure.

Antisense

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the SHIP mRNA. Antisense nucleic acid sequences and delivery methods are well known in the art (Goodchild J., *Curr. Opin. Mol. Ther.,* 2004, April, 6(2):120-128; Clawson G. A. et al., *Gene Ther.,* 2004, September., 11(17):1331-1341), which are incorporated herein by reference in their entirety. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence within the SHIP mRNA. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire SHIP mRNA sequence, but can also be an oligonucleotide that is antisense to only a portion of the SHIP mRNA. For example, the antisense oligonucleotide can be complementary to a portion of the SHIP enzymatic domain (inositol 5'-phosphatase domain) or a portion of the amino-terminal src-homology domain (SH2).

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., systemically or locally by direct injection at a tissue site), or generated in situ such that they hybridize with or bind to cellular mRNA and/or genomic DNA encoding the SHIP to thereby inhibit expression of the SHIP gene. Alternatively, antisense nucleic acid molecules can be modified to target selected cells (such as megakaryocytes and/or megakaryotcyte progenitors) and then administered systemically. For systemic administration, antisense molecules can be modified such that they specifically bind to receptors or antigens (such as CD9, CD41, CD61, actin, or FVIIIRAg) expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.,* 215:327-330 (1987)).

SHIP expression can be inhibited by targeting nucleotide sequences complementary' to the regulatory region of the SHIP gene to form triple helical structures that prevent expression of SHIP in target cells. See generally, Helene, C. Anticancer Drug Des. 6:569-84 (1991); Helene, C. Ann. N.Y. Acad. Sci. 660:27-36 (1992); and Maher, Bioassays 14:807-15 (1992). The potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. Ribozymes and methods for their delivery are well known in the art (Hendry P. et al., BMC Chem. Biol., 2004, Dec., 4(1):1; Grassi G. et al., Curr. Pharm. Biotechnol., 2004, Aug., 5(4):369-386; Bagheri S. et al., Curr. Mol. Med., 2004, Aug., 4(5):489-506; Kashani-Sabet M., Expert Opin. Biol. Ther., 2004, Nov., 4(11):1749-1755), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for SHIP mRNA can include one or more sequences complementary to a nucleotide sequence within the SHIP mRNA, and a sequence having a known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in the mRNA encoded by a uORF of an extended, overlapping 5'-UTR AS mRNA species (see, e.g., Cech et al. U.S. Pat. No. 4,987,071; and Cech et al. U.S. Pat. No. 5,116, 742). Alternatively, SHIP mRNA can be used to select a catalytic RNA having a specific ribonuclease activity from a pool of RNA molecules (see, e.g., Bartel, D. and Szostak, J. W. Science 261:1411-1418 (1993)).

Nucleic Acid Targets

The nucleic acid targets of SHIP inhibitors that are polynucleotides (referred to herein as "polynucleotide SHIP inhibitors" or "nucleic acid SHIP inhibitors") such as the antisense, interfering RNA molecules, and ribozymes described herein, may be any portion of the SHIP gene or SHIP mRNA. In some embodiments, the nucleic acid target is the SHIP enzymatic domain (inositol 5'-phosphatase) or the amino-terminal src-homology domain (SH2). In other embodiments, the nucleic acid target is a translation initiation site, 3' untranslated region, or 5' untranslated region As indicated above, the nucleotide sequences of mouse SHIP and human SHIP have been publicly available for several years (GenBank Accession Numbers NM_10566 and NM_005541, respectively, on the NCBI database). Pair-wise alignment scoring of orthologues shows high levels of homology among SHIP sequences of humans, mice, and rats. Each sequence has the SHIP enzymatic domain (inositol 5'-phosphatase domain), and the degree of nucleotide homology between human, mouse, and rat is over 85%. Furthermore, mice and humans are believed to have the same five SHIP protein isoforms. In a preferred embodiment, the polynucleotide SHIP inhibitor (e.g., interfering RNA, antisense oligonucleotide, ribozyme) targets an mRNA sequence shared by all known hematopoietic SHIP isoforms in humans. Such target sequence can be readily determined by those skilled in the art due to the extensive amount of sequence overlap between the isoforms.

The target SHIP sequence can be within any orthologue of SHIP, such as sequences substantially identical to human, mouse, rat, or bovine, or a portion of any of the foregoing, including but not limited to GenBank Accession Numbers NM_005541 and NM_001017915 (human), NM_10566 (mouse), and U55192 (rat).

Table 1 lists thirteen target sequences predicted to have good specificity and knockdown potential against the human SHIP cDNA sequence.

TABLE 1

| Seq. Identifier | Target Sequence | Region | Start (nt) | GC Content |
|---|---|---|---|---|
| SEQ ID NO: 3 | GCCTGTTGTCATCCATTGA | ORF | 890 | 47.37% |
| SEQ ID NO: 4 | ATAAGTTGGTGATCTTGGT | ORF | 1145 | 36.84% |
| SEQ ID NO: 5 | GCCACATCTGTACTGACAA | ORF | 1589 | 47.37% |
| SEQ ID NO: 6 | AGACAGGCATTGCAAACAC | ORF | 1613 | 47.37% |
| SEQ ID NO: 7 | ACATCACTCACCGCTTCAC | ORF | 1802 | 52.63% |
| SEQ ID NO: 8 | TCTTAACTACCGTGTGGAT | ORF | 1842 | 42.11% |
| SEQ ID NO: 9 | AATACGCCTACACCAAGCA | ORF | 2039 | 47.37% |
| SEQ ID NO: 10 | GTACCAGCGACATCATGAC | ORF | 2156 | 52.63% |
| SEQ ID NO: 11 | GCGACATCATGACGAGTGA | ORF | 2162 | 52.63% |
| SEQ ID NO: 12 | AGGACAGATTGAGTTTCTC | ORF | 2265 | 42.11% |
| SEQ ID NO: 13 | GGTGCTATGCCACATTGAA | ORF | 2285 | 47.37% |
| SEQ ID NO: 14 | GTTTGGTGAGACTCTTCCA | ORF | 2418 | 47.37% |
| SEQ ID NO: 15 | AGACGGAGCGTGATGAATC | ORF | 2687 | 52.63% |

The term "orthologue" as used herein refers to a sequence which is substantially identical to a reference sequence. The tem "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* 48:444-453 (1970)) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. *J. Mol. Biol.* 215:403-10 (1990). BLAST nucleotide searches can be performed with the NBLAST program, score=100, word length=12, to obtain nucleotide sequences homologous to known SHIP nucleic acid sequences. BLAST protein searches can be performed with the XBLAST program, score=50, word length=3, to obtain amino acid sequences homologous to known polypeptide products of the SHIP gene. To obtain gapped alignments for comparison purposes, Gapped BLAST can be utilized as described in Altschul et al., *Nucleic Acids Res.* 25:3389-3402 (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., a human cDNA library, using a probe designed to identify sequences which are substantially identical to a reference sequence.

Pharmaceutical Compositions and Methods of Administration

The SHIP inhibitors of the subject invention (such as interfering RNA molecules, antisense molecules, and ribozymes) can be incorporated into pharmaceutical compositions. Such compositions typically include the SHIP inhibitor and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, $19^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the SHIP inhibitors can be delivered in the form of an aerosol spray from a pressurized container or dispenser which contains a suitable propellant, e.g., a gas such as carbon dioxide, or a nebulizer. Such inhalation methods and inhalant formulations include those described in U.S. Pat. No. 6,468,798.

Systemic administration of SHIP inhibitors can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

The SHIP inhibitors can also be administered by transfection or infection using methods known in the art, including but not limited to the methods described in McCaffrey et al., *Nature* 418(6893):38-39 (2002) (hydrodynamic transfection); Xia et al., *Nature Biotechnol.* 20(10):1006-10 (2002) (viral-mediated delivery); or Putnam, *Am. J. Health Syst. Pharm*, 53(2):151-160 (1996), erratum at Am. J. Health Syst. Pharm. 53(3):325 (1996).

SHIP inhibitors that are polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the polynucleotide SHIP inhibitors are prepared with carriers that will protect the polynucleotide against rapid elimination from, or degradation in, the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. Examples of such antigens presented by megakaryocytes and their progenitors include CD9, CD41, CD61, actin, and FVIIIRAg. These can be prepared according to methods known to those skilled in the art, for example, as described in U.S. Pat. No. 4,522,811. Strategies that inhibit members of the RNAse A family of enzymes or can otherwise protect polynucleotide SHIP inhibitors from these enzymes may be utilized. For example, U.S. Pat. No. 6,096,720 (Love et al.) describes oligonucleotides targeted to human raf mRNA, which are entrapped in sterically stabilized liposomes. In one embodiment, the oligonucleotide in Love et al. is a chimeric olignonucleotide containing a first region to enhance target affinity and a second region that is a substrate for RNase. siSHIELD RNAse inhibitor is designed to prevent degradation of siRNA by RNase (MP BIOMEDICALS, Irvine, Calif.). A strategy for the compaction of short oligonucleotides into well-defined condensates may also be used to deliver the polynucleotides of the subject invention (Sarkar T. et al., *Nucleic Acids Research*, 2005, 33(1):143-151), which is incorporated herein by reference in its entirety.

In particular, suitable techniques for cellular administration of the polynucleotide SHIP inhibitors, such as interfering RNA, in vitro or in vivo are disclosed in the following articles:

General Reviews:

Borkhardt, A. *Cancer Cell*, 2002, 2:167-8; Hannon, G. J. *Nature*, 2002, 418:244-51; McManus, M. T. and Sharp, P. A. *Nat Rev Genet.*, 2002, 3:737-47; Scherr, M. et al. *Curr Med. Chem.*, 2003, 10:245-56; Shuey, D. J. et al. *Drug Discov Today*, 2002, 7:1040-6; Gilmore, I. R. et al., *J. Drug Target.*, 2004, 12(6):315-340; Dykxhoorn, D. M. and Lieberman J., *Annu. Rev. Med.*, 2005, 56:401-423.

Systemic Delivery Using Liposomes:

Lewis, D. L. et al. *Nat Genet.*, 2002, 32:107-8; Paul, C. P. et al. *Nat Biotechnol.*, 2002, 20:505-8; Song, E. et al. *Nat Med.*, 2003, 9:347-51; Sorensen, D. R. et al. *J Mol Biol.*, 2003, 327:761-6.

Virus Mediated Transfer:

Abbas-Terki, T. et al. *Hum Gene Ther.*, 2002, 13:2197-201; Barton, G. M. and Medzhitov, R. *Proc Natl Acad Sci USA*, 2002, 99:14943-5; Devroe, E. and Silver, P. A. *BMC Biotechnol.*, 2002, 2:15; Lori, F. et al. *Am J Pharmacogenomics*, 2002, 2:245-52; Matta, H. et al. *Cancer Biol Ther.*, 2003, 2:206-10; Qin, X. F. et al. *Proc Natl Acad Sci USA*, 2003, 100:183-8; Scherr, M. et al. *Cell Cycle*, 2003, 2:251-7; Shen, C. et al. *FEBS Lett.*, 2003, 539:111-4; Lee S. K. et al *Blood*, 2005, 106(3):818-826, epub Apr. 14, 2005.

Peptide Delivery:

Morris, M. C. et al. *Curr Opin Biotechnol.*, 2000, 11:461-6; Simeoni, F. et al. *Nucleic Acids Res.*, 2003, 31:2717-24.

Song E. et al. describe antibody mediated in vivo delivery of siRNAs via cell-surface receptors (Song E. et al., *Nat. Biotechnol.*, 2005, 23(6):709-717, epub May 22, 2005). This cell-specific delivery technique can be used to target interfering RNA molecules to the cell-surface receptors on megakaryocytes and megakaryocyte progenitors.

Other technologies that may be suitable for delivery of polynucleotide SHIP inhibitors, such as interfering RNA, to the target cells are based on nanoparticles or nanoeapsules such as those described in U.S. Pat. Nos. 6,649,192B and 5,843,509B. Recent technologies that may be employed for selecting, delivering, and monitoring interfering RNA molecules include Raab, R. M. and Stephanopoulos, G. *Biotechnol. Bioeng.*, 2004, 88:121-132; Huppi, K. et al. *Mol. Cell*, 2005, 17:1-10; Spagnou, S. et al. *Biochemistry*, 2004, 43:13348-13356; Muratovska, A. and Eccles, M. R. *FEBS Lett.*, 2004, 558:63-68; Kumar, R. et al. *Genome Res.*, 2003, 13:2333-2340; Chen, A. A. et al. *Nucleic Acids Res.*, 2005, 33:e190; Dykxhoorn, D. M. et al. *Gene Ther.*, 2006, epub ahead of print; Rodriguez-Lebron, E. and Paulson, H. L. *Gene Ther.*, 2005, epub ahead of print; Pai, S. I. et al. *Gene Ther.*, 2005, epub ahead of print; Raoul, C. et al. *Gene Ther.*, 2005, epub ahead of print; Manfredsson, F. P. et al. *Gene Ther.*, 2005, epub ahead of print; Downward, J. *BMJ*, 2004, 328: 1245-1248.

A mixture of SHIP inhibitors, of the same type or different types, may be introduced into cells in vitro or in vivo. For example, a mixture or pool of polynucleotide SHIP inhibitors such as interfering RNA molecules (e.g., 2-4 interfering molecules or more) can be introduced into cells (Oleinikov A. V. et al., *Nucleic Acids Research*, 2005, 33(10):e92). Preferably, the interfering RNA molecules target different regions of the SHIP mRNA. Preferably, the interfering RNA molecules have been previously validated as individually functioning to reduce SHIP expression. The individual interfering RNAs of the mixture can be chemically synthesized (Elbashir S. M. et al., *Genes Dev.*, 2001, 15:188-200) or introduced as short DNA templates containing RNA polymerase promoter, which are transcribed within the cells in vitro or in vivo (Yu J. Y. et al., *Proc. Natl. Acad. Sci. USA*, 99:6047-6052).

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The SHIP inhibitor can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a SHIP inhibitor can include a single treatment or can include a series of treatments.

The polynucleotide SHIP inhibitors (e.g., interfering RNA, antisense oligonucleotide, or ribozyme) can be introduced (administered) into cells (such as mammalian cells) in vitro or in vivo using known techniques, as those described herein, to suppress gene expression. Similarly, genetic constructs (e.g., transcription vectors) containing DNA of the invention may be introduced into cells in vitro or in vivo using known techniques, as described herein, for transient or stable expression of RNA, to suppress gene expression. When administered to the cells in vivo, the polynucleotide SHIP inhibitors can be administered to a subject systemically (e.g., intravenously), for example, or administered locally at the site of the cells (such as the peripheral blood, bone marrow, or spleen).

The cells in which the polynucleotide SHIP inhibitors are introduced may be any cell, such as a megakaryocyte or megakaryocyte progenitor, containing SHIP mRNA. The cells can be primary cells, cultured cells, cells of cell lines, etc. In one embodiment, the cells are from bone marrow. In another embodiment, the cells are from the spleen. In another embodiment, the cells are from peripheral blood.

Mammalian species which benefit from the disclosed methods include, but are not limited to, primates, such as humans, apes, chimpanzees, orangutans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the terms "subject", "patient", and "individual" are used interchangeably and intended to include such human and non-human mammalian species. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one mammalian species to another mammalian species), relative to the subject.

The polynucleotide SHIP inhibitors of the invention can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad. Sci. USA* 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotide SHIP inhibitors can be small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296:550-553 (2002); Lee et al., (2002), supra; Miyagishi and Taira, *Nature Biotechnol.* 20:497-500 (2002); Paddison et al. (2002), supra; Paul (2002), supra; Sui (2002) supra; Yu et al. (2002), supra.

siRNAs targeting SHIP mRNA may be fused to other nucleotide molecules, or to polypeptides, in order to direct their delivery or to accomplish other functions. Thus, for example, fusion proteins comprising a siRNA oligonucleotide that is capable of specifically interfering with expression of SHIP may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6:1204, 1988), or the XPRESS epitope tag (INVITROGEN, Carlsbad, Calif.). The affinity sequence may be a hexa-histidine tag as supplied, for example, by a pBAD/H is (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

The present invention also relates to vectors and to constructs that include or encode polynucleotide SHIP inhibitors (e.g., siRNA), and in particular to "recombinant nucleic acid constructs" that include any nucleic acid such as a DNA polynucleotide segment that may be transcribed to yield SHIP-specific siRNA polynucleotides according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., *Nat. Biotechnol.* 20:497-500 (2002); Lee et al., *Nat. Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci. USA* 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for a SHIP mRNA sequence may be transcribed under the control of a single promoter such that the siRNA polynucleotide forms a hairpin molecule (Paul et al., supra). In such instance, the complementary strands of the siRNA specific sequences are separated by a spacer that comprises at least four nucleotides, but may comprise at least 5, 6, 7, 8, 9, 10, 11, 12, 14, 16, or 18 or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotide SHIP inhibitors can be expressed in mammalian cells, yeast, bacteria, or other cells under the control of appropriate promoters, providing ready systems for evaluation of siRNA polynucleotides that are capable of interfering with SHIP expression as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor, N.Y., (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold. Spring Harbor Laboratory, Plainview, N.Y.); and elsewhere.

The DNA sequence in the expression vector is operatively linked to at least one appropriate expression control sequence (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Examples of Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above.). A tissue-specific promoter allows preferential expression of the polynucleotide SHIP inhibitor in a given target tissue, thereby avoiding expression in other tissues. For example, to target genes specifically in the heart, a number of cardiac-specific regulatory elements can be used. An example of a cardiac-specific promoter is the ventricular form of MLC-2v promoter (see, Zhu et al., *Mol. Cell. Biol.* 13:4432-4444, 1993; Navankasattusas et al., *Mol. Cell Biol.* 12:1469-1479, 1992) or a variant thereof such as a 281 by fragment of the native MLC-2v promoter (nucleotides −264 to +17, GenBank Accession No. U26708). Examples of other cardiac-specific promoters include alpha myosin heavy chain (Minamino et al., *Circ. Res.* 88:587-592, 2001) and myosin light chain-2 (Franz et al., *Circ. Res.* 73:629-638, 1993). Endothelial cell gene promoters include endoglin and ICAM-2. See Velasco et al., *Gene Ther.* 8:897-904, 2001. Liver-specific promoters include the human phenylalanine hydroxylase (PAH) gene promoters (Bristeau et al., *Gene* 274:283-291, 2001), hB1F (Zhang et al., *Gene* 273:239-249, 2001), and the human C-reactive protein (CRP) gene promoter (Ruther et al., *Oncogene* 8:87-93, 1993). Promoters that are kidney-specific include CLCN5 (Tanaka et al., *Genomics* 58:281-292, 1999), renin (Sinn et al., *Physical Genomics* 3:25-31, 2000), androgen-regulated protein, sodium-phosphate cotransporter, renal cytochrome P-450, parathyroid hormone receptor and kidney-specific cadherin. See *Am. J. Physiol. Renal Physiol.* 279:F383-392, 2000. An example of a pancreas-specific promoter is the pancreas duodenum homeobox 1 (PDX-1) promoter (Samara et al., *Mol. Cell Biol.* 22:4702-4713, 2002). A number of brain-specific promoters may be useful in the invention and include the thy-1 antigen and gamma-enolase promoters (Vibert et al., *Eur. J. Biochem.* 181:33-39, 1989), the glial-specific glial fibrillary acidic protein (GFAP) gene promoter (Cortez et al., *J. Neurosci. Res.* 59:39-46, 2000), and the human FGF1 gene promoter (Chiu et al., *Oncogene* 19:6229-6239, 2000). The GATA family of transcription factors have promoters directing neuronal and thymocyte-specific expression (see Asnagli et al., *J. Immunol.* 168:4268-4271, 2002).

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo.

Various mammalian cell culture systems can also be employed to produce polynucleotide SHIP inhibitors from recombinant nucleic acid constructs of the present invention. The invention is therefore directed in part to a method of producing a polynucleotide, such as an siRNA, by culturing a host cell comprising a recombinant nucleic acid construct that comprises at least one promoter operably linked to a polynucleotide SHIP inhibitor. In certain embodiments, the promoter may be a regulated promoter as provided herein, for example a tetracycline-repressible promoter. In certain embodiments the recombinant expression construct is a recombinant viral expression construct as provided herein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

As used herein, the terms "administer", "introduce", "apply", "treat", "transplant", "implant", "deliver", and grammatical variations thereof, are used interchangeably to provide SHIP inhibitors to target cells in vitro (e.g., ex vivo) or in vivo, or provide genetically modified (engineered) cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

As used herein, the term "or" is inclusive of "both" (i.e., and/or). For example, as used herein, reference to megakaryocytes "or" megakaryocyte progenitors includes "either" or "and" (i.e., and/or). When the amount or concentration of megakaryocytes or megakaryocyte progenitors is to be determined, the amount or concentration of either or both cell types is intended.

The terms "comprising", "consisting of" and "consisting essentially of" are defined according to their standard meaning. The terms may be substituted for one another throughout the instant application in order to attach the specific meaning associated with each term.

In general, the target nucleic acid is DNA or RNA. However, inventive methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the sensitivity of the target cells to radiation therapy may be extracted by a variety of techniques such as that described by Sambrook, et al. (Molecular Cloning: A Laboratory Manual, Cold Spring Harbor, N.Y., 1989; incorporated in its entirety herein by reference).

Cells expressing the target nucleic acid isolated from a subject can be obtained in a biological specimen from the subject. The cells, or nucleic acid, can be isolated from tumor tissue, blood, plasma, serum, lymph, lymph nodes, spleen, bone marrow, or any other biological specimen containing the target nucleic acid. Tumor tissue, blood, plasma, serum, lymph, spleen, and bone marrow are obtained by various medical procedures known to those of skill in the art.

The inventive methods are useful for producing a clinical response to treatment of various human anemias, bone marrow transplants, or cell proliferative disorders. A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g., its cells do not invade surrounding tissues or metastasize to distant sites. The term "malignant" refers to a tumor that is metastatic, invades contiguous tissue or no longer under normal cellular growth control.

As used herein, "a clinical response" is the response of a subject to modulation of the gene of interest. Criteria for determining a response to therapy are widely accepted and enable comparisons of the efficacy alternative treatments (see Slapak and Kufe, Principles of Cancer Therapy, in Harrisons's Principles of Internal Medicine, $13^{th}$ edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

SHIP inhibitors (also referred to herein as "active compounds") can be incorporated into pharmaceutical compositions suitable for administration. Such compositions typically comprise the SHIP-inhibiting nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to target cells with monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Assays. The invention provides a method (also referred to herein as a "screening assay") for identifying SHIP inhibitors, i.e., candidate or test compounds or agents (e.g., peptides, peptidomimetics, small molecules or other drugs) that bind to the SHIP protein or have a stimulatory or inhibitory effect on, for example, the SHIP gene expression or SHIP gene activity. Such identified compounds may be useful for the modulation of drug resistance. In one embodiment, the invention provides assays for screening candidate or test compounds which bind to or modulate the activity of the target gene protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam (1997) Anti-cancer Drug Des. 12:145).

Examples of methods for the synthesis of molecular libraries can be found in the art, for example in: DeWitt et al. *Proc. Natl. Acad. Sci. USA*, 1993, 90:6909; Erb et al. *Proc. Natl. Acad. Sci. USA*, 1994, 91:11422; Zuckermann et al. *J. Med. Chem.*, 1994, 37:2678; Cho et al. *Science*, 1993, 261:1303; Carrell et al. *Angew. Chem. Int. Ed. Engl.*, 1994, 33:2059; Carell et al. *Angew. Chem. Int. Ed. Engl.*, 1994, 33:2061; and Gallop et al. *J. Med. Chem.*, 1994, 37:1233.

Libraries of compounds may be presented in solution (e.g., Houghten *Bio/Techniques*, 1992, 13:412-421), or on beads (Lam *Nature*, 1991, 354:82-84), chips (Fodor *Nature*, 1993, 364:555-556), bacteria (U.S. Pat. No. 5,223,409), spores (U.S. Pat. Nos. 5,571,698; 5,403,484; and 5,223,409), plasmids (Cull et al. *Proc. Natl. Acad. Sci. USA*, 1992, 89:1865-1869) or on phage (Scott and Smith *Science*, 1990, 249:386-390; Devlin *Science*, 1990, 249:404-406; Cwirla et al. *Proc. Natl. Acad. Sci.*, 1990, 87:6378-6382; and Felici *J. Mol: Biol.*, 1991, 222:301-310).

In one embodiment, an assay is a cell-based assay in which a cell which expresses the target gene protein, or a biologically active portion thereof, is contacted with a test compound and the ability of the test compound to bind to the target gene protein determined. The cell, for example, can be a yeast cell or a cell of mammalian origin. Determining the ability of the test compound to bind to the target gene protein can be accomplished, for example, by coupling the test compound with a radioisotope or enzymatic label such that binding of the test compound to the target gene protein or biologically active portion thereof can be determined by detecting the labeled compound in a complex. For example, test compounds can be labeled with $^{125}$I, $^{35}$C, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses the target gene protein, or a biologically active portion thereof, with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or a biologically active portion thereof as compared to the known compound.

In another embodiment, an assay is a cell-based assay comprising contacting a cell expressing the target gene protein, or a biologically active portion thereof, with a test compound and determining the ability of the test compound to modulate (e.g., stimulate or inhibit) the activity of the target gene protein or biologically active portion thereof. Determining the ability of the test compound to modulate the activity of the target gene or a biologically active portion thereof can be accomplished, for example, by determining the ability of the target gene protein to bind to or interact with the target gene target molecule. As used herein, a "target molecule" is a molecule with which the target gene protein binds or interacts in nature, for example, a molecule in the nucleus or cytoplasm of a cell which expresses the target gene protein. The target gene target molecule can be a non-target gene molecule or the target gene protein or polypeptide. The target, for example, can be a second intracellular protein which has catalytic activity, a protein which naturally binds to the target gene, or a protein which facilitates the association of DNA with the target gene.

Determining the ability of the target gene protein to bind to or interact with the target gene target molecule can be accomplished by one of the methods described above for determining direct binding. In a preferred embodiment, determining the ability of the target gene protein to bind to or interact with the target gene target molecule can be accomplished by determining the activity of the target molecule or detecting a cellular response, for example, cell survival or cell proliferation in the presence of a chemotherapeutic drug.

In yet another embodiment, an assay of the present invention is a cell-free assay comprising contacting the target gene protein or biologically active portion thereof with a test compound and determining the ability of the test compound to bind to the target gene protein or biologically active portion thereof. Binding of the test compound to the target gene protein can be determined either directly or indirectly as described above. In a preferred embodiment, the assay includes contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or biologically active portion thereof as compared to the known compound.

In another embodiment, an assay is a cell-free assay comprising contacting the target gene protein or biologically active portion thereof with a test compound and determining the ability of the test compound to modulate (e.g., stimulate or inhibit) the activity of the target gene protein or biologically active portion thereof. Determining the ability of the test compound to modulate the activity of the target gene can be accomplished, for example, by determining the ability of the target gene protein to bind to the target gene target molecule by one of the methods described above for determining direct binding. In an alternative embodiment, determining the ability of the test compound to modulate the activity of the target gene can be accomplished by determining the ability of the target gene protein further modulate the target gene target molecule. For example, the catalytic/enzymatic activity of the target molecule on an appropriate substrate can be determined as previously described.

In yet another embodiment, the cell-free assay comprises contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the target gene protein to preferentially bind to or modulate the activity of the target gene target molecule.

The cell-free assays of the present invention are amenable to use of both native and variant forms (e.g., peptide fragments and fusion proteins) of the target gene. In the case of cell-free assays comprising a hydrophobic form of the target gene, it may be desirable to utilize a solubilizing agent such that the hydrophobic form of the target gene is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the target gene or its target molecule to facilitate separation of complexed from uncomplexed forms of one or both of the proteins, as well as to accommodate automation of the assay. Binding of a test compound to the target gene, or interaction of the target gene with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/target gene fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or the target gene protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of the target gene binding or activity determined using standard techniques.

Other techniques for immobilizing proteins on matrices can also be used in the screening assays of the invention. For example, either the target gene or its target molecule can be immobilized utilizing conjugation of biotin and streptavidin. Biotinylated target gene or target molecules can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the target gene or target molecules but which do not interfere with binding of the target gene protein to its target molecule can be derivatized to the wells of the plate, and unbound target or the target gene trapped in the wells by antibody conjugation. Methods for detecting such complexes, in addition to those described above for the GST-immobilized complexes, include immunodetection of complexes using antibodies reactive with the target gene or target molecule, as well as enzyme-linked assays which rely on detecting an enzymatic activity associated with the target gene or target molecule.

In another embodiment, modulators of the target gene expression are identified in a method in which a cell is contacted with a candidate compound and the expression of the target gene (mRNA or protein, or the copy number of the target gene) in the cell is determined. The level of expression of the target gene in the presence of the candidate compound is compared to the level of expression of the target gene in the absence of the candidate compound. The candidate compound can then be identified as a modulator of the target gene expression based on this comparison. For example, when expression of the target gene mRNA or protein is greater (statistically significantly greater) in the presence of the candidate compound than in its absence, the candidate compound is identified as a stimulator of the target gene mRNA or protein expression. Alternatively, when expression of the target gene mRNA or protein is less (statistically significantly less) in the presence of the candidate compound than in its absence, the candidate compound is identified as an inhibitor of the target gene mRNA or protein expression. The level of the target gene mRNA or protein expression in the cells, or the number of the target gene copies per cell can be determined by methods described herein for detecting the target gene genomic DNA, mRNA, or protein.

Target gene proteins can be used as "bait proteins" in a two-hybrid assay or three hybrid assay (see, e.g., U.S. Pat. No. 5,283,317; Zervos et al. *Cell*, 1993, 72:223-232; Madura et al. *J. Biol. Chem.*, 1993, 268:12046-12054; Bartel et al. *Bio/Techniques*, 1993, 14:920-924; Iwabuchi et al. *Oncogene*, 1993, 8:1693-1696; and WO94/10300), to identify other proteins, which bind to or interact with the target gene ("target gene-binding proteins" or "target gene-bp") and modulate the target gene activity.

The two-hybrid system is based on the modular nature of most transcription factors, which consist of separable DNA-binding and activation domains. Briefly, the assay utilizes two different DNA constructs. In one construct, the gene that codes for the target gene is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming the target gene-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the target gene.

This invention further pertains to novel agents identified by the above-described screening assays and uses thereof for treatments as described herein.

Predictive Medicine. The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the target gene protein and/or nucleic acid expression as well as the target gene activity, in the context of a biological sample (e.g., blood, serum, cells, tissue) to thereby determine whether an individual is afflicted with a disease or disorder, or is at risk of developing a disorder, associated with aberrant target gene expression or activity (e.g., altered drug resistance). The invention also provides for prognostic (or predictive) assays for determining whether an individual is at risk of developing a disorder associated with the target gene protein, nucleic acid expression or activity (e.g., altered drug resistance). For example, mutations in the target gene can be assayed in a biological sample. Such assays can be used for prognostic or predictive purpose to thereby prophylactically treat an individual prior to the onset of a disorder characterized by or associated with the target gene protein, nucleic acid expression or activity. For example, because megakaryocyte production is inhibited where the target gene is expressed at a higher level in cells than normal, expression of the target gene can be used as an indicator of diminished megakaryocyte production.

Another aspect of the invention provides methods for determining the target gene protein, nucleic acid expression or the target gene activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Diagnostic Assays. The invention provides a method of assessing expression, especially undesirable expression, of a cellular target gene. Undesirable (e.g., excessive) expression may indicate the presence, persistence or reappearance of reduced megakaryocyte production in an individual's tissue (e.g. spleen or bone marrow). More generally, aberrant expression may indicate the occurrence of a deleterious or disease-associated phenotype contributed to by the target gene.

An exemplary method for detecting the presence or absence of the target gene in a biological sample involves obtaining a biological sample (preferably from a body site implicated in a possible diagnosis of diseased or malignant tissue) from a test subject and contacting the biological sample with a compound or an agent capable of detecting the target gene protein or nucleic acid (e.g., mRNA, genomic DNA) that encodes the target gene protein such that the presence of the target gene is detected in the biological sample. The presence and/or relative abundance of the target gene indicates aberrant or undesirable expression of a cellular the target gene, and correlates with the occurrence in situ of reduced megakaryocytes in the periphery.

A preferred agent for detecting the target gene mRNA or genomic DNA is a labeled nucleic acid probe capable of hybridizing to the target gene mRNA or genomic DNA. The nucleic acid probe can be, for example, a full-length the target gene nucleic acid, or a portion thereof, such as an oligonucleotide of at least 15, 30, 50, 100, 250 or 500 nucleotides in length and sufficient to specifically hybridize under stringent conditions to the target gene mRNA or genomic DNA. Other suitable probes for use in the diagnostic assays of the invention are described herein.

A preferred agent for detecting the target gene protein is an antibody capable of binding to the target gene protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect the target gene mRNA, protein, or genomic DNA in a biological sample in vitro as well as in vivo. For example, in vitro techniques for detection of the target gene mRNA include Northern hybridizations and in situ hybridizations. In vitro techniques for detection of the target gene protein include enzyme linked immunosorbent assays (ELISAs), Western blots, immunoprecipitations and immunofluorescence. In vitro techniques for detection of the target gene genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting the target gene protein, mRNA, or genomic DNA, such that the presence of the target gene protein, mRNA or genomic DNA is detected in the biological sample, and comparing the presence of the target gene protein, mRNA or genomic DNA in the control sample with the presence of the target gene protein, mRNA or genomic DNA in the test sample.

The invention also encompasses kits for detecting the presence of the target gene in a biological sample (a test sample). Such kits can be used to determine if a subject is suffering from or is at increased risk of developing a disorder associated with aberrant expression of the target gene (e.g., the presence of a drug resistance cancer). For example, the kit can comprise a labeled compound or agent capable of detecting the target gene protein or mRNA in a biological sample and means for determining the amount of the target gene in the sample (e.g., an anti-target gene antibody or an oligonucleotide probe which binds to DNA encoding the target gene). Kits may also include instruction for observing that the tested subject is suffering from or is at risk of developing a disorder associated with aberrant expression of the target gene if the amount of the target gene protein or mRNA is above or below a normal level.

For antibody-based kits, the kit may comprise, for example: (1) a first antibody (e.g., attached to a solid support) which binds to the target gene protein; and, optionally, (2) a second, different antibody which binds to the target gene protein or the first antibody and is conjugated to a detectable agent.

For oligonucleotide-based kits, the kit may comprise, for example: (1) a oligonucleotide, e.g., a detectably labelled oligonucleotide, which hybridizes to the target gene nucleic acid sequence or (2) a pair of primers useful for amplifying the target gene nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the target gene.

Pharmacogenomics. Agents, or modulators which have a stimulatory or inhibitory effect on the target gene activity (e.g., SHIP) as identified by a screening assay can be administered to individuals to treat (prophylactically or therapeutically) disorders (e.g., anemias) associated with aberrant target gene activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of the target gene protein, expression of the target gene nucleic acid, or mutation content of the target genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder, *Clin. Chem.*, 1997, 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

Thus, the activity of the target gene product (SHIP), expression of the target gene nucleic acid, or mutation content of the target genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with the target gene modulator, such as a modulator identified by one of the exemplary screening assays described herein.

Monitoring of Effects During Clinical Trials. Monitoring the influence of agents (e.g., drugs, compounds) on the expression or activity of the target gene (e.g., the ability to modulate the SHIP phenotype of a cell) can be applied not only in basic drug screening, but also in clinical trials. For example, the effectiveness of an agent determined by a screening assay to decrease the target gene expression, protein levels, or downregulate the target gene activity, can be monitored in clinical trails of subjects exhibiting increased target gene expression, protein levels, or upregulated target gene activity.

Alternatively, the effectiveness of an agent determined by a screening assay to increase the target gene expression, protein levels, or upregulate target gene activity (e.g., to decrease megakaryocyte production), can be monitored in clinical trials of compounds designed to increase the target gene expression, protein levels, or upregulate target gene activity. In such clinical trials, the expression or activity of the target gene and, preferably, other genes that have been implicated in, for example, a cellular proliferation disorder, can be used as a "read out" or markers of the drug resistance of a particular cell.

For example, and not by way of limitation, genes, including the target gene, that are modulated in cells by treatment with an agent (e.g., compound, drug or small molecule) which modulates the target gene activity (e.g., identified in a screening assay) can be identified. Thus, to study the effect of agents on cellular proliferation disorders, for example, in a clinical trial, cells can be isolated and RNA prepared and analyzed for the levels of expression of the target gene and other genes implicated in the disorder. The levels of gene expression (i.e., a gene expression pattern) can be quantified by Northern blot analysis or RT-PCR, or as is otherwise known in the art, or alternatively by measuring the amount of protein produced, by one of the methods as described herein, or by measuring the levels of activity of the target gene or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a preadministration sample from a subject prior to administration of the agent; (ii) detecting the level of expression of the target gene protein, mRNA, or genomic DNA in the preadministration sample; (iii) obtaining one or more post-administration samples from the subject; (iv) detecting the level of expression or activity of the target gene protein, mRNA, or genomic DNA in the post-administration samples; (v) comparing the level of expression or activity of the target gene protein, mRNA, or genomic DNA in the pre-administration sample with the target gene protein, mRNA, or genomic DNA in the post administration sample or samples; and (vi) altering the administration of the agent to the subject accordingly. For example, increased administration of the agent may be desirable to decrease the expression or activity of the target gene to lower levels than detected, i.e., to increase the effectiveness of the agent.

Methods of Treatment. The present invention provides for both prophylactic and therapeutic methods of treating a subject at risk of (or susceptible to) a disorder or having a disorder associated with aberrant target gene expression or activity. Alternatively, the target gene expression or activity may be normal (non-aberrant) but a decrease in target gene expression or activity would nonetheless have a beneficial effect on the subject. Such disorders include various human anemias and those in need of bone marrow transplants.

Prophylactic Methods. In one aspect, the invention provides a method for preventing in a subject, a disease or condition associated with an aberrant target gene expression or activity (e.g., the development of drug resistance), by administering to the subject an agent which modulates the target gene expression. Subjects at risk for a condition which is caused or contributed to by aberrant target gene expression or activity can be identified by, for example, any or a combination of diagnostic or prognostic assays as is known in the art. Administration of a prophylactic agent can occur prior to the manifestation of symptoms characteristic of target gene aberrancy, such that a disease or disorder is prevented or, alternatively, delayed in its progression. For example, administration of a prophylactic agent to a patient in need of a bone marrow transplant may prevent or delay the development of platelet production dropping below a critical threshold. Depending on the type of the target gene aberrancy, for example, the target gene agonist or the target gene antagonist agent can be used for treating the subject. The appropriate agent can be determined based on screening assays described herein.

Therapeutic Methods. Another aspect of the invention pertains to methods of modulating the target gene expression or activity for therapeutic purposes. For example, the effectiveness of a bone marrow transplant is "potentiated" (enhanced) by increasing megakaryocyte production. The modulation of expression of the target gene disclosed in the method of the invention involves contacting a cell with an agent that modulates one or more of the activities of the target gene protein activity associated with the cell. An agent that modulates the target gene protein activity can be an agent as described herein, such as a nucleic acid or a protein, a naturally-occurring cognate ligand of the target gene protein, a peptide, the target gene peptidomimetic, or other small molecule. In one embodiment, the agent stimulates one or more of the biological activities of the target gene protein. Examples of such stimulatory agents include active the target gene protein and a nucleic acid molecule encoding the target gene that has been introduced into the cell. In another embodiment, the agent inhibits one or more of the biological activities of the target gene protein. Examples of such inhibitory agents include antisense target gene nucleic acid molecules and anti-target gene antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of the target gene protein or nucleic acid molecule. In one embodiment, the method involves administering an agent, or combination of agents that modulates (e.g., upregulates or downregulates) the target gene expression or activity. In another embodiment, the method involves administering the target gene protein or nucleic acid molecule as therapy to compensate for reduced or aberrant target gene expression or activity.

For example, in one embodiment, the method involves administering a desired drug to an individual with a cell population expressing relatively high target gene levels, and coadministering an inhibitor of the target gene expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an the target gene antisense oligonucleotide in combination with one or more other antisense oligonucleotides) can be administered to the individual sufficiently in advance of administration of the drug to allow the antisense composition to permeate the individual's tissues, especially tissue comprising the transformed cells to be eradicated; to be internalized by transformed cells; and to disrupt the target gene expression and/or protein production.

Inhibition of the target gene activity is desirable in situations in which the target gene is abnormally upregulated and/or in which decreased target gene activity is likely to have a beneficial effect, e.g., increasing megakaryocyte production in the tissue of patient. Conversely, stimulation of the target gene activity is desirable in situations in which the target gene is abnormally downregulated and/or in which increased target gene activity is likely to have a beneficial effect, e.g., in decreasing megakaryocyte and megakaryocyte progenitor production.

Materials And Methods

Mice strains. SHIP$^{-/-}$ mice (F9 or F10 X C57BL6/J) produced in the inventors' laboratory have a deletion of the SHIP promoter and first exon (Wang, J. W. et al. *Science*, 2002, 295:2094-2097). A second SHIP-deficient mouse model, SHIP$^{\Delta IP/\Delta IP}$ (129SvJ) (Karlsson, M. C. et al. *J Exp Med.*, 2003, 198:333-340) in which the inositol phosphatase domain is deleted, was also analyzed (kindly provided by Dr. Jeffrey Ravetch, Rockefeller University, NY, USA). All studies described herein were conducted on six to eight week-old adult mice. Experiments were performed in compliance with institutional guidelines of the University of South Florida.

Cell isolation. Isolation of BM cells and splenocytes was as described (Wang, J. W. et al. *Science*, 2002, 295:2094-2097). Following red blood cell (RBC) lysis, the cells were re-suspended in staining medium (Wang, J. W. et al. *Science*, 2002, 295:2094-2097). PB was obtained from the retro-orbital sinus. For MKP analysis of PB, RBC were lysed in 1×RBC lysis buffer (EBIOSCIENCE, San Diego, Calif.) twice. Cells were then re-suspended for antibody staining.

Flow cytometry analysis and antibodies. Staining of MKP and MK was performed as per Hodohara et al. (Hodohara, K. et al. *Blood*, 2000, 95:769-775). All antibodies were from BD PHARMINGEN (San Diego, Calif.) except when mentioned otherwise. The cells were treated with anti-CD16/CD32 (2.4G2) to block Fc receptors and then stained with a lineage panel (PE), CD41-FITC(MWReg30), and cKit-APC(2B8). The Lineage panel was CD3e(17A2), CD4(GK1.5), CD8a (53-6.7), B220(RA3-6B2), Gr-1(RB6-8C5), Mac-1 (M1/70) (CALTAG, Burlingame, Calif.) and Ter119(TER-119). Dead cells were excluded using 7-AAD (BD PHARMINGEN, San Diego, Calif.). Analysis was done on a FACS Calibur and display of FACS data was performed using FlowJo 4.5.

Platelet analysis. Platelets were quantified using the Cell-Dyn 3700 hematology analyzer (ABBOTT DIAGNOSTIC, Dallas, Tex. USA).

It should be understood that the examples and embodiments described herein are for illustrative purposes only and that various modifications or changes in light thereof will be suggested to persons skilled in the art and are to be included within the spirit and purview of this application.

EXAMPLE 1

SHIP-deficient Mice have Increased Numbers of MKP and MK

BM, spleen, and PB from SHIP$^{-/-}$, SHIP$^{\Delta IP/\Delta IP}$, and WT mice were analyzed by flow cytometry to determine the size of the megakaryocyte progenitor (MKP) and megakaryocyte (MK) compartment in vivo (FIG. 1A), using an immunophenotype defined by Hodohara and colleagues (Hodohara, K. et al. *Blood*, 2000, 95:769-775), Lin$^-$cKit$^+$CD41$^+$, which contains the majority of CFU-Mk activity. In BM, an expansion of the MKP compartment in SHIP$^{-/-}$ and SHIP$^{\Delta IP/\Delta IP}$ mice was observed (FIG. 1B). SHIP$^{-/-}$ and SHIP$^{\Delta IP/\Delta IP}$ spleens also show higher percentages of MKP compared to WT littermates (data not shown). Thus, SHIP$^{-/-}$ and SHIP$^{\Delta IP/\Delta IP}$ BM show a mean 18.1-fold and 50-fold increase, respectively, in the absolute number of MKP relative to WT controls (FIG. 1B). PB contained very few MKP, 3 to 5 MKP/µl, and their numbers were not significantly increased in SHIP$^{-/-}$ mice when compared to WT. However, MKP numbers were slightly, but significantly higher, in SHIP$^{\Delta IP/\Delta IP}$ PB as compared to WT littermates (FIG. 1B).

Figures 1, 1C:
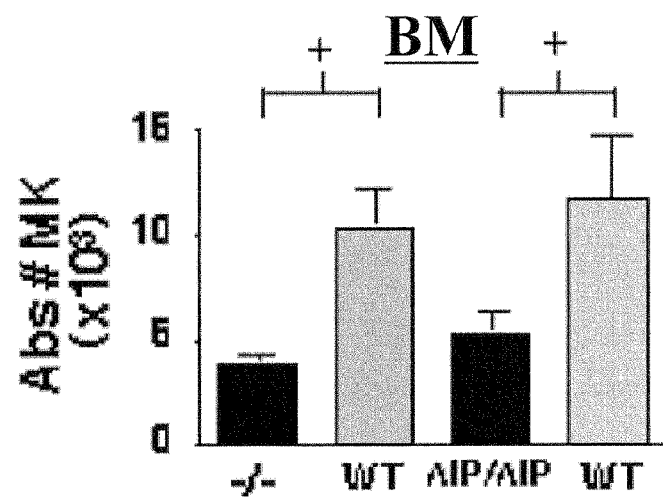
Figures 1, 1C, 2:
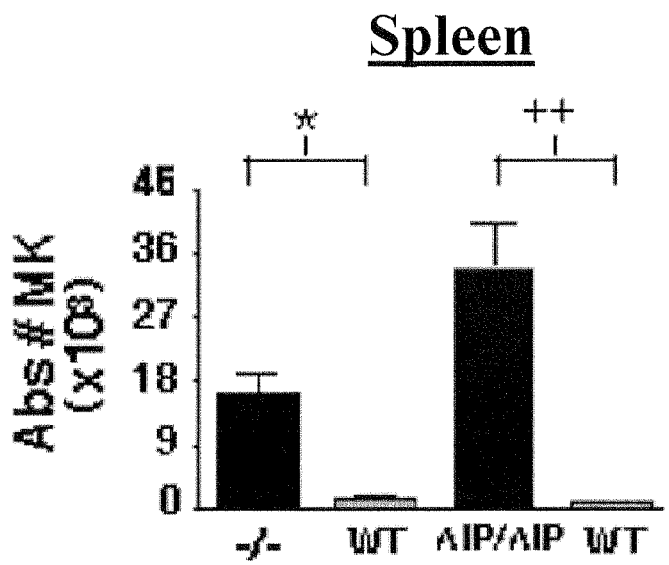
Figures 1, 1C, 2, 3:
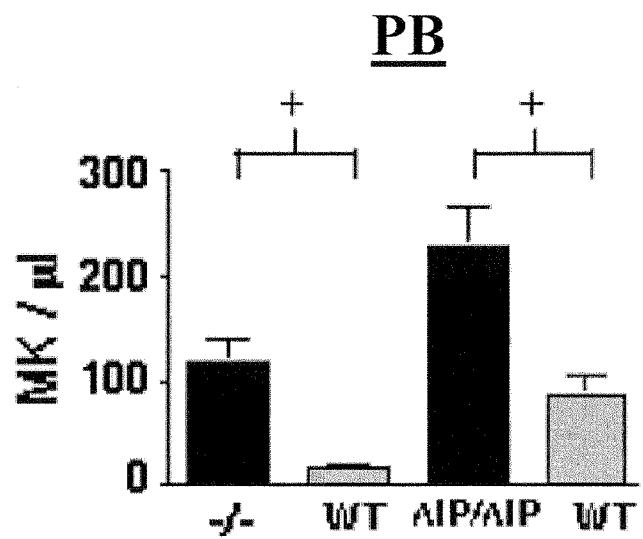

Assessing the MK compartment, it was observed that SHIP$^{-/-}$ and SHIP$^{\Delta IP/\Delta IP}$ BM contains significantly less MK compared to WT controls (FIG. 1C). However, in the spleen, there was a greater number of MK in SHIP$^{-/-}$ and SHIP$^{\Delta IP/\Delta IP}$ mice compared to their respective WT littermates (FIG. 1C). In SHIP$^{-/-}$ spleen there is a mean 10.9-fold increase in the absolute number of MK (FIG. 1C). Furthermore, in the PB of SHIP$^{-/-}$ mice there is a mean 7.7-fold increase in the absolute number of MK and the same trend was observed for SHIP$^{\Delta IP/\Delta IP}$ mice (FIG. 1C).

Figure 1D:
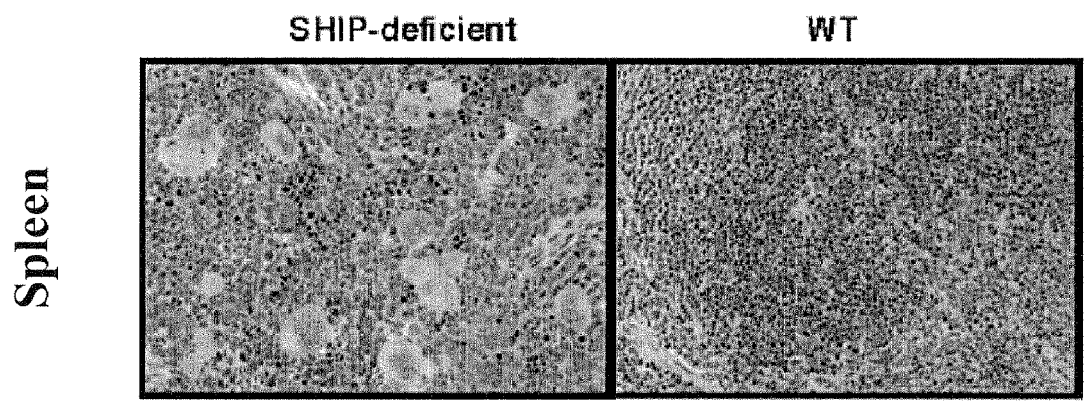
Figure 1E:
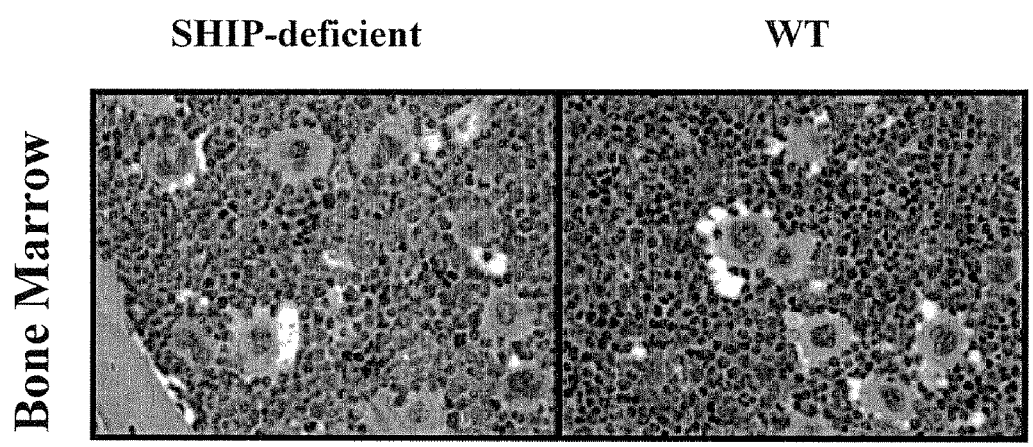

The increase in MK numbers found by flow cytometry in the SHIP-deficient spleens was corroborated by morphology, where the spleen of SHIP-deficient mice contained an increased number of MK (FIG. 1D). Furthermore, the BM histopathology revealed that MK in SHIP$^{-/-}$ BM have a hypolobulated micromegakaryocytic morphology when compared to WT BM, which contains mature hyperlobulated MK (FIG. 1E).

EXAMPLE 2

Platelet Levels Remain Unchanged in Ship-deficient Mice

Despite the profound expansion of the MKP and the MK compartment in SHIP$^{-/-}$ and SHIP$^{\Delta IP/\Delta IP}$ mice, they do not exhibit increased platelet levels relative to WT controls, when measured by hematolyzer or flow cytometry. Platelet levels limit megakaryocytopoiesis by sequestering TPO (Kaushansky, K. N Engl J Med., 1998, 339:746-754). Since platelet levels are not significantly increased in SHIP-deficient mice, it is possible that SHIP-deficiency increases the sensitivity of MK and MKP to steady-state TPO levels. Thus, proliferation and/or survival of MKP and MK is increased in SHIP mutant mice, leading to an expansion of the megakaryocytic compartment. Consistent with the present inventors' hypothesis, TPO stimulation of primary MK and c-mpl transfected Ba/F3 cells leads to SHIP phosphorylation and activation of downstream effectors of the cell cycle and survival (Geddis, A. E. et al. J Biol Chem., 2001, 276:34473-34479).

Table 2 shows the different SHIP-deficient models and their WI littermates (n>6 mice/genotype). Data was analyzed using an unpaired, two-tailed. Students' T-test.

TABLE 2

Platelet counts in SHIP-deficient mice.

| Mice genotype | Platelet levels (# × 10$^3$/µl) |
|---|---|
| SHIP$^{-/-}$ | 672.8 ± 43.4$^{++}$ |
| SHIP$^{+/-}$ | 848.9 ± 35.7 |
| SHIP$^{+/+}$ (C57Bl6) | 803.7 ± 31.5 |
| SHIP$^{\Delta IP/\Delta IP}$ | 455.4 ± 81.1$^{++}$ |

TABLE 2-continued

Platelet counts in SHIP-deficient mice.

| Mice genotype | Platelet levels (# × 10$^3$/µl) |
|---|---|
| SHIP$^{+/\Delta IP}$ | 652.3 ± 28.0 |
| SHIP$^{+/+}$ (129SvJ) | 647.9 ± 28.0 |

$^{++}$p < 0.05 compared to their respective WT and SHIP heterozygous littermates A decrease in the number of MK in the BM of SHIP-deficient mice and an increase in MK numbers in the PB and spleen were observed. This may be due to increased responsiveness of MK to SDF-1, which would cause trans-endothelial migration of MK from the BM to the circulation (Wang, J. F. et al. Blood, 1998, 92:756-764; Hamada, T. et al. J Exp Med., 1998, 188:539-548; Avecilla, S. T. et al., Nat Med., 2004, 10:64-71). Thus, SHIP may also control pathways that mediate MK migration in response to SDF-1, as it does in myeloid progenitors (Kim, C. H. et al. J Clin Invest., 1999, 104:1751-1759).

Despite an increase in the level of MKP and MK, the platelet counts were reduced in SHIP-deficient mice. It is well established that SHIP$^{-/-}$ mice suffer from splenomegaly, resulting from extramedullary hematopoieisis, where SHIP-deficient spleen are enlarged by 5-fold (Helgason et al., Genes Dev., 1998, 12:1610-20). Since splenomegaly has been associated with splenic platelet sequestration previously (Aster R H Br. J., Haematol., 1972, 22:259-63) (Naouri et al. Acta Haematol., 1993, 89:200-3), the present inventors hypothesize that SHIP-deficient spleens sequester platelets, leading to a reduction in circulating platelet numbers in the peripheral blood.

Thus, overall, these findings suggest that SHIP can be targeted in vivo to increase the pool of MKP and MK, and thus enable this compartment to replenish platelets more rapidly following myeloablative chemotherapy and radiation treatment, for example.

EXAMPLE 3

MKP and MK are Increased in BM and Spleen of SHIP-ablated Mice

Figure 5A:
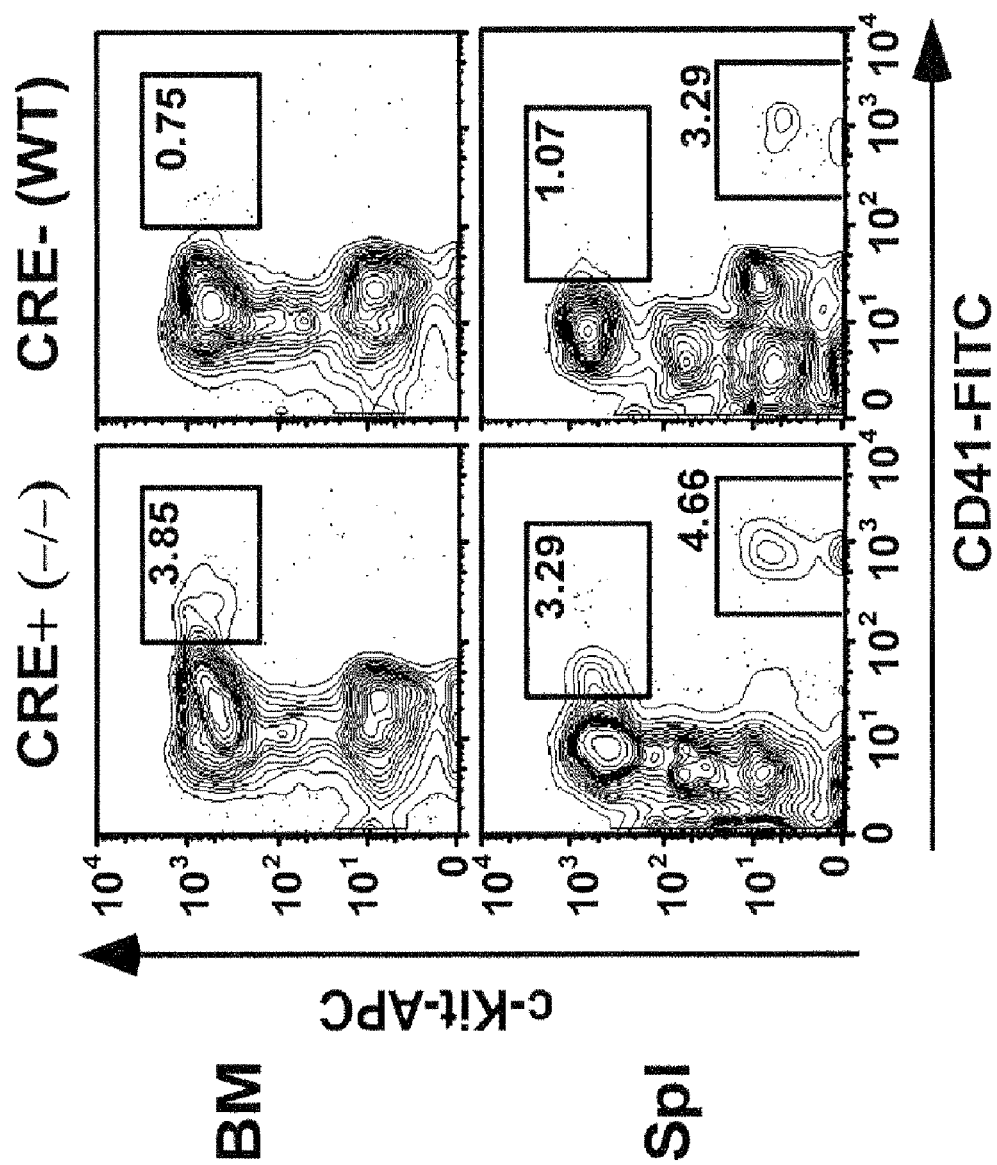

To observe if inhibition of SHIP during adulthood could also result in an increase in MKP production, the present inventors used the MxCre model (Wang et al. Science, 2002, 295:2094-2097). Briefly, the treatment of MxCRE+$^{fl/fl}$ mice with polyIC will lead to Cre recombinase expression through Type interferon-inducible Mx1 promoter, and deletion of the gene section between two loxP sites (Kuhn et al. Science, 1995, 259:1427-1429; Oberdoerffer et al. Nucleic Acids Res., 2003, 31:e140). In this case, the promoter and the first exon of the SHIP gene will be deleted resulting in the ablation of SHIP expression. As a control, MxCre-/SHIP$^{fl/fl}$ are treated with polyIC in the same manner than the MxCRE+$^{fl/fl}$ mice. Twenty-one days after the last polyIC treatment, mice were euthanized and the level of MKP was evaluated by flow cytometry (FIG. 5A). As observed in FIG. 5B-1, there was an increase in the percentage of MKP in the BM and spleen of SHIP-ablated mice as compared to MxCre- mice. Furthermore, it was observed that SHIP-ablated BM contains approximately 4 times more MKP than their MxCre- counterpart (FIG. 5B-2). As for the germline SHIP$^{-/-}$, an increase in the percentage of MK present in the spleen was also observed (shown in FIG. 5B-3). This result suggests that mice that undergo normal development can also exhibit increased MKP numbers once SHIP is deleted during adulthood. Thus, methods and agents that inhibit SHIP function could be used as a therapy in vitro (e.g., ex vivo) or in vivo to increase megakaryocytopoiesis in adult patients.

EXAMPLE 4

SHIP Knockdown Using Interfering RNA

Four potential interfering RNA sequences targeting human SHIP were obtained from Open Biosystems:

```
siRNA sequence H1:
                                          (SEQ ID NO: 16)
AAGGAAUUGCGUUUACACUUA siRNA sequence H2:
                                          (SEQ ID NO: 17)
AAAAUUGCGUUUACACUUACA shRNA sequence 63332:
                                          (SEQ ID NO: 18)
TGCTGTTGACAGTGAGCGAGGCTTCCAGAAGAGCATCTTATAGTGAAGC
CACAGATGTATAAGATGCTCTTCTGGAAGCCCTGCCTACTGCCTCGGA shRNA sequence 63331:
                                          (SEQ ID NO: 19)
TGCTGTTGACAGTGAGCGAGCCCATATCACCCAAGAAGTTTAGTGAAGC

CACAGATGTAAACTTCTTGGGTGATATGGGCGTGCCTACTGCCTCGGA
```

The underlined portion of shRNA 63332 (SEQ ID NO:18): GCTTCCAGAAGAGCATCTTAT (SEQ ID NO:20), and shRNA 63331 (SEQ ID NO:19): GCCCATATCACCCAA-GAAGTTT (SEQ ID NO:21), represent the target sequences in human SHIP. The other non-underlined portions are the loop and termini of the shRNA.

Figure 6:
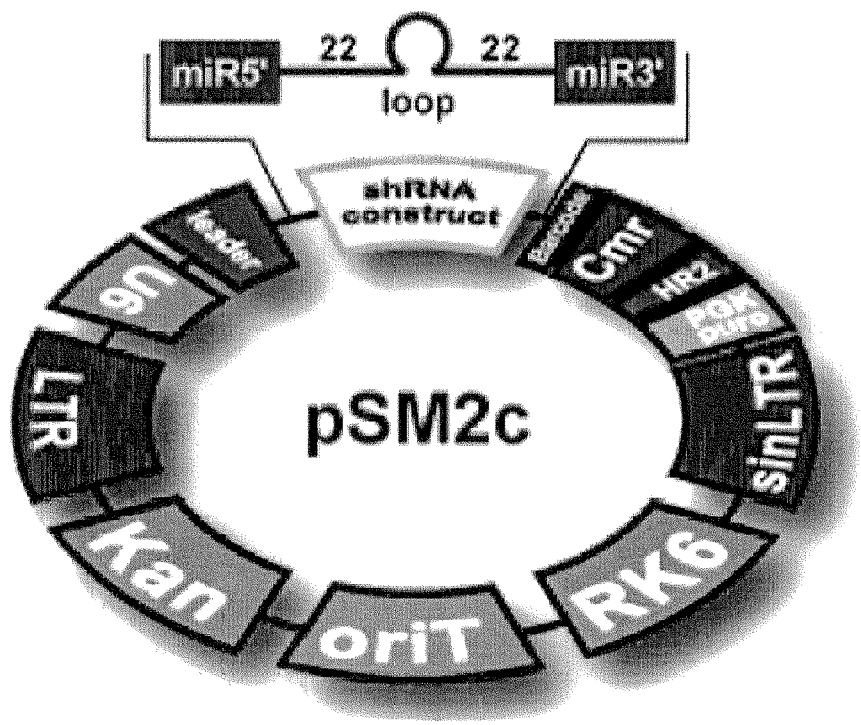
FIG. 6 is a general vector map representing shRNA 63332 and shRNA 63331.

FIG. 4 shows the human SHIP cDNA sequence with the targets for siRNA sequence H1 (SEQ ID NO:16), siRNA sequence H2 (SEQ ID NO:17), shRNA 63332 (SEQ ID NO:18), and shRNA 63331 (SEQ ID NO:19) in boxes. FIG. 6 is a general vector map representing shRNA 63332 and shRNA 63331.

Figure 7:
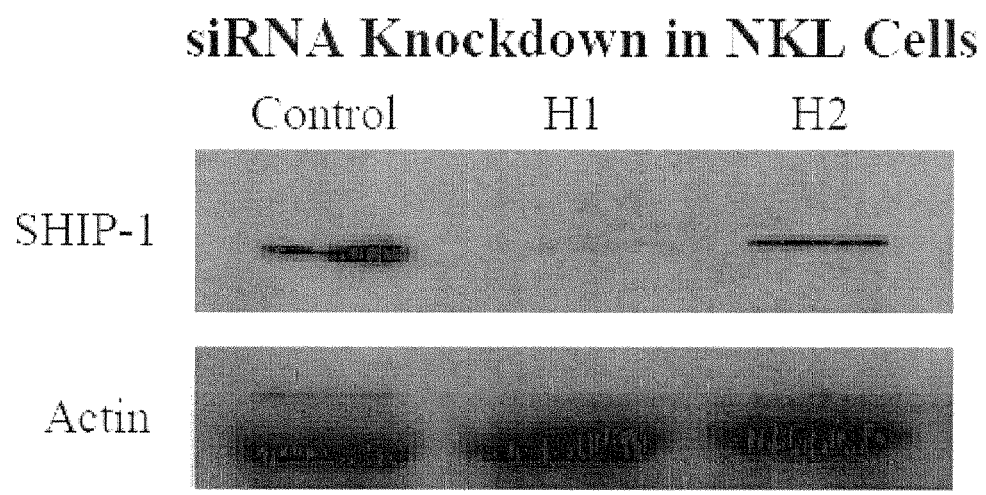
FIG. 7 is a Western blot demonstrating SHIP knockdown in NK cell lines using siRNA sequence H1 (SEQ ID NO:16) and siRNA sequence H2 (SEQ ID NO:17). Actin was used as the control.

H1 was predicted to have the best knockdown effectiveness by the siRNA design tool available on the DHARMACON website, using the default parameters. H1 and H2 siRNA were delivered to human NK cells in vitro using the nucleofection system (AMAXA, Maryland, USA). Twenty-four hours later, cells were lysed and a Western Blot was performed to determine the level of SHIP protein in the test cells following administration of the siRNAs. The β-actin protein level was also observed to ensure equal loading of the protein lysate. Results are shown in FIG. 7. Both H1 and H2 effectively reduced SHIP expression; however, H1 was more effective, which was consistent with the siRNA design tool.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

All patents, patent applications, provisional applications, and publications referred to or cited herein are incorporated by reference in their entirety, including all figures and tables, to the extent they are not inconsistent with the explicit teachings of this specification.

We claim:

1. A method for improving haematopoietic recovery in a patient in need thereof, comprising:
   harvesting megakaryocytes or megakaryocyte progenitors from a patient;
   contacting the megakaryocytes or megakaryocyte progenitors with an effective amount of an inhibitor of SH2-containing inositol-5-phosphatase (SHIP) function, thereby expanding the megakaryocytes or megakaryocyte progenitors, wherein the inhibitor of SHIP function is selected from the group consisting of interfering RNA, antisense oligonucleotide, ribozyme, DNAzyme, nucleic acid modifier, PNA, nonstandard nucleic acid, aptamer, decoy, and dominant/negative mutant; and
   reinfusing the expanded megakaryocytes or megakaryocyte progenitors into the patient.

2. The method of claim 1, wherein said method further comprises determining the amount or concentration of megakaryocytes or megakaryocyte progenitors in the patient before said harvesting, after said reinfusing, or both.

3. The method of claim 1, wherein the inhibitor of SHIP function is an interfering RNA targeted to SHIP mRNA.

4. The method of claim 3, wherein the interfering RNA is targeted to the SHIP enzymatic domain (inositol 5'-phosphatase domain).

5. The method of claim 3, wherein the interfering RNA is targeted to the amino-terminal src-homology domain (SH2).

6. The method of claim 1, wherein the patient is human.

7. The method of claim 1, wherein the inhibitor of SHIP function is an interfering RNA or antisense oligonucleotide, and wherein the interfering RNA or antisense oligonucleotide is targeted to SHIP mRNA.

8. The method of claim 1, wherein the inhibitor of SHIP function is an antisense oligonucleotide targeted to SHIP mRNA.

9. The method of claim 3, wherein the interfering RNA is a small interfering RNA (shRNA).

10. The method of claim 3, wherein the interfering RNA is a small hairpin RNA (siRNA).

11. The method of claim 7, wherein the patient is human.

12. The method of claim 6, wherein the human patient has an anemia.

13. The method of claim 6, wherein the human patient has undergone a bone marrow transplant.

* * * * *

UNITED STATES PATENT AND TRADEMARK OFFICE
CERTIFICATE OF CORRECTION

| | |
|---|---|
| PATENT NO. | : 8,008,273 B2 |
| APPLICATION NO. | : 12/819711 |
| DATED | : August 30, 2011 |
| INVENTOR(S) | : William G. Kerr, Caroline Desponts and Lia Elena Perez |

It is certified that error appears in the above-identified patent and that said Letters Patent is hereby corrected as shown below:

Column 9,
Line 9, "in a samples" should read --in a sample--.
Lines 38-39, "molecule" or deoxyribonucleic acid molecule" refers" should read
--molecule" or "deoxyribonucleic acid molecule" refers--.

Column 10,
Line 63, "the tens" should read --the term--.

Column 12,
Line 55, "polymerase Ill promoters" should read --polymerase III promoters--.

Column 17,
Line 13, "RNase lll-type" should read --RNase III-type--.

Column 19,
Line 2, "complementary' to" should read --complementary to--.

Column 20,
Lines 45-46, "The tem" should read --The term--.

Column 25,
Line 6, "nanoparticles or nanoeapsules" should read --nanoparticles or nanocapsules--.

Column 27,
Line 20, "siRNAs targeting" should read --SiRNAs targeting--.

Column 29,
Line 56, "a 281 by fragment" should read --a 281 bp fragment--.

Signed and Sealed this
Sixth Day of December, 2011

David J. Kappos
*Director of the United States Patent and Trademark Office*

Column 35,
Line 45, "or³H" should read --or ³H--.

Column 40,
Line 43, "which hinds to DNA" should read --which binds to DNA--.
Line 56, "detectably labelled" should read --detectably labeled--.

Column 45,
Line 56, "WI littermates" should read --WT littermates--.

Column 82,
Line 37, "RNA (shRNA)" should read --RNA (siRNA)--.
Line 39, "RNA (siRNA)" should read --RNA (shRNA)--.